(12) United States Patent
Blumberg et al.

(10) Patent No.: US 6,649,611 B2
(45) Date of Patent: Nov. 18, 2003

(54) PIPERAZINE DERIVATIVES

(75) Inventors: Laura C. Blumberg, Waterford, CT (US); Matthew F. Brown, Pawcatuck, CT (US); Ronald P. Gladue, Stonington, CT (US); Molly A. McGlynn, New London, CT (US); Christopher S. Poss, North Stonington, CT (US)

(73) Assignee: Pfizer, Inc., New York, NY (US)

( * ) Notice: Subject to any disclaimer, the term of this patent is extended or adjusted under 35 U.S.C. 154(b) by 0 days.

(21) Appl. No.: 09/821,322

(22) Filed: Mar. 29, 2001

(65) Prior Publication Data

US 2002/0107255 A1 Aug. 8, 2002

Related U.S. Application Data

(60) Provisional application No. 60/193,789, filed on Mar. 31, 2000.

(51) Int. Cl.$^7$ .................. A61K 31/495; A61K 31/496; C07D 295/182; C07D 241/04; C07D 405/12

(52) U.S. Cl. ................ 514/235.8; 514/252.11; 514/253.01; 514/254.05; 514/254.1; 514/255.01; 544/121; 544/357; 544/360; 544/372; 544/374; 544/370; 544/379; 544/391

(58) Field of Search ................... 544/391, 121, 544/357, 360, 370, 372, 374, 379; 514/255.01, 235.8, 252.11, 253.01, 254.05, 254.1

(56) References Cited

U.S. PATENT DOCUMENTS 6,207,665 B1    3/2001    Bauman et al. ............. 514/235

FOREIGN PATENT DOCUMENTS

DE    WO9856771    12/1998

*Primary Examiner*—Emily Bernhardt
(74) *Attorney, Agent, or Firm*—Peter C. Richardson; Gregg C. Benson; Lisa A. Samuels

(57) ABSTRACT

A compound of the formula

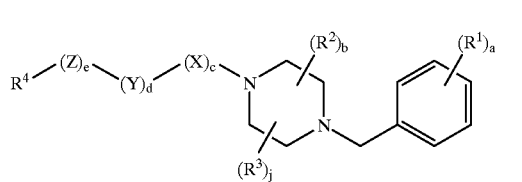

or the pharmaceutically acceptable salt thereof; wherein a, b, c, d, e, j, $R^1$, $R^2$, $R^3$, and $R^4$ are as defined herein and are useful to treat inflammation and other immune disorders.

6 Claims, No Drawings

PIPERAZINE DERIVATIVES

BACKGROUND OF THE INVENTION

The present invention relates to novel piperazine derivatives, methods of use and pharmaceutical compositions containing them.

The compounds of the invention are potent and selective inhibitors of chemokine binding to its receptor CCR1 found on inflammatory and immunomodulatory cells (preferably leukocytes and lymphocytes). The CCR1 receptor is also sometimes referred to as the CC-CKR1 receptor. These compounds also inhibit MIP-1α (and the related chemokines shown to interact with CCR1 (e.g., RANTES and MCP-3)) induced chemotaxis of THP-1 cells and human leukocytes and are potentially useful for the treatment or prevention of autoimmune diseases (such as rheumatoid arthritis, type I diabetes (recent onset), lupus, inflammatory bowel disease, optic neuritis, psoriasis, multiple sclerosis, polymyalgia rheumatica, uveitis, and vasculitis), acute and chronic inflammatory conditions (such as osteoarthritis, adult Respiratory Distress Syndrome, Respiratory Distress Syndrome of infancy, ischemia reperfusion injury, and glomerulonephritis), allergic conditions (such as asthma and atopic dermatitis), infection associated with inflammation (such as viral inflammation (including influenza and hepatitis) and Guillian-Barre), chronic bronchitis, xenotransplantation, transplantation tissue rejection (chronic and acute), organ transplant rejection (chronic and acute), atherosclerosis, restenosis, HIV infectivity (co-receptor usage), and granulomatous diseases (including sarcoidosis, leprosy and tuberculosis) and sequelae associated with certain cancers such as multiple myeloma. Compounds in this series may also limit the production of cytokines at inflammatory sites, including but not limited to TNF and IL-1, as a consequence of decreasing cell infiltration, providing benefit for diseases linked to TNF and IL-1, including congestive heart failure, pulmonary emphysema or dyspnea associated therewith, emphysema; HIV-1, HIV-2, HIV-3; cytomegalovirus (CMV), adenoviruses, Herpes viruses (Herpes zoster and Herpes simplex). They may also provide benefit for the sequelae associated with infection where such infection induces production of detrimental inflammatory cytokines such as TNF e.g, fungal meningitis, joint tissue damage, hyperplasia, pannus formation and bone resorption, psoriatic arthritis, hepatic failure, bacterial meningitis, Kawasaki syndrome, myocardial infarction, acute liver failure, lyme disease, septic shock, cancer, trauma, and malaria.

MIP-1α and RANTES are soluble chemotactic peptides (chemokines) which are produced by inflammatory cells, in particular CD8+ lymphocytes, polymorphonuclear leukocytes (PMNs) and macrophages, *J. Biol. Chem.,* 270 (30) 29671–29675 (1995). These chemokines act by inducing the migration and activation of key inflammatory and immunomodulatory cells. Elevated levels of chemokines have been found in the synovial fluid of rheumatoid arthritis patients, chronic and acute rejecting tissue from transplant patients and in the nasal secretions of allergic rhinitis patients following allergen exposure (Teran, et al., *J. Immunol.,* 1806–1812 (1996), and Kuna et al., *J. Allergy Clin. Immunol.* 321 (1994)). Antibodies which interfere with the chemokine/receptor interaction by neutralizing MIP1α or gene disruption have provided direct evidence for the role of MIP-1α and RANTES in disease by limiting the recruitment of monocytes and CD8+ lymphocytes (Smith et al., *J. Immunol,* 153, 4704 (1994) and Cook et al., *Science,* 269, 1583 (1995)). Together this data demonstrates that CCR1 receptor antagonists would be an effective treatment of several immune based diseases. The compounds described within are potent and selective antagonists of the CCR1 receptor.

SUMMARY OF THE INVENTION

The present invention also relates to a compound of the formula

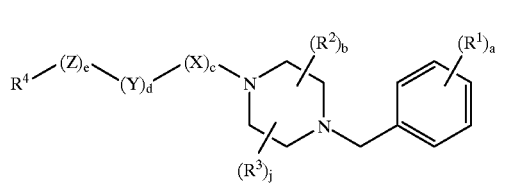

or the pharmaceutically acceptable salt thereof; wherein
a is 1, 2, 3, 4 or 5;
b is 0, 1, 2, 3 or 4;
c is 0 or 1;
d is 1, 2, 3, 4 or 5;
e is 0 or 1;
j is 1, 2, 3, or 4;
X is C(O), C(S) or $CH_2$;
Y is $CH_2$, or if e is 0, Y is $CHR^8$ wherein $R^8$ is hydrogen, $(C_6-C_{10})$aryl or $NR^9R^{10}$;
Z is oxygen, $NR^9$ or $CR^{11}R^{12}$;
each $R^1$ is independently selected from hydrogen, hydroxy, hydroxysulfonyl, halo, $(C_1-C_6)$alkyl, mercapto, mercapto$(C_1-C_6)$alkyl, $(C_1-C_6)$alkylthio, $(C_1-C_6)$alkylsulfinyl, $(C_1-C_6)$alkylsufonyl, $(C_1-C_6)$alkylthio$(C_1-C_6)$alkyl, $(C_1-C_6)$alkylsulfinyl$(C_1-C_6)$alkyl, $(C_1-C_6)$alkylsulfonyl$(C_1-C_6)$alkyl, $(C_1-C_6)$alkoxy, $(C_6-C_{10})$aryloxy, halo$(C_1-C_6)$alkyl, trifluoromethyl, formyl, formyl$(C_1-C_6)$alkyl, nitro, nitroso, cyano, $(C_6-C_{10})$aryl$(C_1-C_6)$alkoxy, halo$(C_1-C_6)$alkoxy, trifluoromethoxy, $(C_3-C_7)$cycloalkyl, $(C_3-C_7)$cycloalkyl$(C_1-C_6)$alkyl, hydroxy$(C_3-C_7)$cycloalkyl$(C_1-C_6)$alkyl, $(C_3-C_7)$cycloalkylamino, $(C_3-C_7)$cycloalkylamino$(C_1-C_6)$alkyl, $((C_3-C_7)$cycloalkyl$)((C_1-C_6)$alkyl$)$amino, $((C_3-C_7)$cycloalkyl$(C_1-C_6)$alkyl$)$amino$(C_1-C_6)$alkyl, cyano$(C_1-C_6)$alkyl, $(C_2-C_7)$alkenyl, $(C_2-C_7)$alkynyl, $(C_6-C_{10})$aryl, $(C_6-C_{10})$aryl$(C_1-C_6)$alkyl, $(C_6-C_{10})$aryl$(C_2-C_6)$alkenyl, hydroxy$(C_1-C_6)$alkyl, hydroxy$(C_6-C_{10})$aryl $(C_1-C_6)$alkyl, hydroxy$(C_1-C_6)$alkylthio$(C_1-C_6)$alkyl, hydroxy$(C_2-C_6)$alkenyl, hydroxy$(C_2-C_6)$alkynyl, $(C_1-C_6)$alkoxy$(C_1-C_6)$alkyl, $(C_1-C_6)$alkoxy$(C_6-C_{10})$aryl$(C_1-C_6)$alkyl, $(C_6-C_{10})$aryloxy$(C_1-C_6)$alkyl, $(C_6-C_{10})$aryl$(C_1-C_6)$alkoxy$(C_1-C_6)$alkyl, amino, $(C_1-C_6)$alkylamino, $((C_1-C_6)$alkyl$)_2$amino, $(C_6-C_{10})$arylamino, $(C_6-C_{10})$aryl$(C_1-C_6)$alkylamino, amino$(C_1-C_6)$alkyl, $(C_1-C_6)$alkylamino$(C_1-C_6)$alkyl, $((C_1-C_6)$alkyl$)_2$amino$(C_1-C_6)$alkyl, hydroxy$(C_1-C_6)$alkylamino$(C_1-C_6)$alkyl, $(C_6-C_{10})$acylamino$(C_1-C_6)$alkyl, $(C_6-C_{10})$aryl $(C_1-C_6)$alkylamino$(C_1-C_6)$alkyl, $(C_1-C_6)$alkylcarbonylamino, $((C_1-C_6)$alkylcarbonyl$)$ $((C_1-C_6)$alkyl$)$amino, $(C_1-C_6)$alkylcarbonylamino $(C_1-C_6)$alkyl, $((C_1-C_6)$alkylcarbonyl$)((C_1-C_6)$alkyl$)$ amino$(C_1-C_6)$alkyl, $(C_1-C_6)$alkoxycarbonylamino, $(C_1-C_6)$alkoxycarbonyl$)(C_1-C_6)$alkylamino, $(C_1-C_6)$ alkoxycarbonylamino$(C_1-C_6)$alkyl, $(C_1-C_6)$ alkoxycarbonyl$)((C_1-C_6)$alkyl$)$amino$(C_1-C_6)$alkyl, , $(C_1-C_6)$alkoxycarbonyl, $(C_6-C_{10})$aryl$(C_1-C_6)$ alkoxycarbonyl, $(C_1-C_6)$alkylcarbonyl, $(C_1-C_6)$ alkylcarbonyl($C_1$–$C_6$)alkyl, ($C_6$–$C_{10}$)arylcarbonyl, ($C_6$–$C_{10}$)arylcarbonyl($C_1$–$C_6$)alkyl, ($C_6$–$C_{10}$)aryl($C_1$–$C_6$)alkylcarbonyl, ($C_6$–$C_{10}$)aryl($C_1$–$C_6$)alkycarbonyl($C_1$–$C_6$)alkyl, carboxy($C_1$–$C_6$)alkyl, ($C_1$–$C_6$)alkoxycarbonyl($C_1$–$C_6$)alkyl, ($C_6$–$C_{10}$)aryl($C_1$–$C_6$)alkoxycarbonyl($C_1$–$C_6$)alkyl, ($C_1$–$C_6$)alkoxy($C_1$–$C_6$)alkylcarbonyloxy($C_1$–$C_6$)alkyl, aminocarbonyl, ($C_1$–$C_6$)alkylaminocarbonyl, (($C_1$–$C_6$)alkyl)$_2$aminocarbonyl, ($C_6$–$C_{10}$)arylaminocarbonyl, ($C_6$–$C_{10}$)aryl($C_1$–$C_6$)alkylaminocarbonyl, aminocarbonyl($C_1$–$C_6$)alkyl, ($C_1$–$C_6$)alkylaminocarbonyl($C_1$–$C_6$)alkyl, (($C_1$–$C_6$)alkyl)$_2$aminocarbonyl($C_1$–$C_6$)alkyl, ($C_6$–$C_{10}$)arylaminocarbonyl($C_1$–$C_6$)alkyl, ($C_1$–$C_6$)alkylaminocarbonyl($C_1$–$C_6$)alkyl, amidino, guanidino, ureido, ($C_1$–$C_6$)alkylureido, (($C_1$–$C_6$)alkyl)$_2$ureido, ureido($C_1$–$C_6$)alkyl, ($C_1$–$C_6$)alkylureido($C_1$–$C_6$)alkyl, (($C_1$–$C_6$)alkyl)$_2$ureido($C_1$–$C_6$)alkyl, ($C_2$–$C_9$)heterocycloalkyl, ($C_2$–$C_9$)heteroaryl, ($C_2$–$C_9$)heterocycloalkyl($C_1$–$C_6$)alkyl and ($C_2$–$C_9$)heteroaryl($C_1$–$C_6$)alkyl;

each $R^2$ and $R^3$ are independently selected from oxo, halo, ($C_1$–$C_6$)alkyl, ($C_3$–$C_8$)cycloalkyl, ($C_3$–$C_8$)cycloalkyl($C_1$–$C_6$)alkyl, ($C_3$–$C_8$)cycloalkylamino($C_1$–$C_6$)alkyl, ($C_3$–$C_8$)cycloalkyl($C_1$–$C_6$)alkylamino($C_1$–$C_6$)alkyl, halo($C_1$–$C_6$)alkyl, ($C_2$–$C_6$)alkenyl, ($C_2$–$C_6$)alkynyl, ($C_6$–$C_{10}$)aryl, ($C_6$–$C_{10}$)aryl($C_1$–$C_6$)alkyl, ($C_6$–$C_{10}$)aryl($C_2$–$C_6$)alkenyl, H—C(O)—, H—C(O)—($C_1$–$C_6$)alkyl, hydroxy($C_1$–$C_6$)alkyl, hydroxy($C_2$–$C_6$)alkenyl, hydroxy($C_2$–$C_6$)alkynyl, hydroxy($C_6$–$C_{10}$)aryl($C_1$–$C_6$)alkyl, hydroxy($C_3$–$C_8$)cycloalkyl($C_1$–$C_6$)alkyl, thio($C_1$–$C_6$)alkyl, cyano($C_1$–$C_6$)alkyl, halo($C_1$–$C_6$)alkylcarbonylamino($C_1$–$C_6$)alkyl, ($C^1$–$C_6$)alkoxy($C_6$–$C_{10}$)aryl($C_1$–$C_6$)alkyl, ($C_1$–$C_6$)alkoxy($C_1$–$C_6$)alkyl, ($C_6$–$C_{10}$)aryloxy($C_1$–$C_6$)alkyl, ($C_6$–$C_{10}$)aryl($C_1$–$C_6$)alkoxy($C_1$–$C_6$)alkyl, ($C_1$–$C_6$)alkylthio($C_1$–$C_6$)alkyl, ($C_1$–$C_6$)alkylsulfinyl($C_1$–$C_6$)alkyl, ($C_1$–$C_6$)alkylsulfonyl($C_1$–$C_6$)alkyl, hydroxy($C_1$–$C_6$)alkylthio($C_1$–$C_6$)alkyl, amino($C_1$–$C_6$)alkyl, ($C_1$–$C_6$)alkylamino($C_1$–$C_6$)alkyl, (($C_1$–$C_6$)alkyl)$_2$amino($C_1$–$C_6$)alkyl, ($C_6$–$C_{10}$)arylamino($C_1$–$C_6$)alkyl, ($C_6$–$C_{10}$)aryl($C_1$–$C_6$)alkylamino($C_1$–$C_6$)alkyl, ($C_1$–$C_6$)alkylcarbonylamino($C_1$–$C_6$)alkyl, azido($C_1$–$C_6$)alkyl, aminocarbonylamino($C_1$–$C_6$)alkyl, ($C_1$–$C_6$)alkylaminocarbonylamino($C_1$–$C_6$)alkyl, (($C_1$–$C_6$)alkyl)$_2$aminocarbonylamino($C_1$–$C_6$)alkyl, ($C_1$–$C_6$)alkoxycarbonyl ($C_1$–$C_6$)alkylaminocarbonylamino($C_1$–$C_6$)alkyl, ($C^1$–$C_6$)alkoxycarbonylamino($C_1$–$C_6$)alkyl, hydroxy($C_1$–$C_6$)alkylamino($C_1$–$C_6$)alkyl, ($C_6$–$C_{10}$)aryloxy($C_1$–$C_6$)alkylcarbonyloxy($C_1$–$C_6$)alkyl, ($C_1$–$C_6$)alkoxy($C_1$–$C_6$)alkylcarbonyloxy($C_1$–$C_6$)alkyl, ($C_6$–$C_{10}$)aryl($C_1$–$C_6$)alkoxy($C_1$–$C_6$)alkylcarbonyloxy($C_1$–$C_6$)alkyl, ($C_1$–$C_6$)alkylcarbonyl($C_1$–$C_6$)alkylcarbonyl($C_1$–$C_6$)alkyl, carboxy, ($C_1$–$C_6$)alkoxycarbonyl, ($C_6$–$C_{10}$)aryl($C_1$–$C_6$)alkoxycarbonyl, ($C_6$–$C_{10}$)aryl($C_1$–$C_6$)alkylcarbonyl, aminocarbonyl, ($C_1$–$C_6$)alkylaminocarbonyl, (($C_1$–$C_6$)alkyl)$_2$aminocarbonyl, ($C_6$–$C_{10}$)arylaminocarbonyl, ($C_6$–$C_{10}$)aryl($C_1$–$C_6$)alkylaminocarbonyl, carboxy($C_1$–$C_6$)alkyl, ($C_1$–$C_6$)alkoxycarbonyl($C_1$–$C_6$)alkyl, ($C_6$–$C_{10}$)aryl($C_1$–$C_6$)alkoxycarbonyl($C_1$–$C_6$)alkyl, aminocarbonyl($C_1$–$C_6$)alkyl, ($C_1$–$C_6$)alkylaminocarbonyl($C_1$–$C_6$)alkyl, (($C_1$–$C_6$)alkyl)$_2$aminocarbonyl($C_1$–$C_6$)alkyl, ($C_6$–$C_{10}$)arylaminocarbonyl($C_1$–$C_6$)alkyl, ($C_6$–$C_{10}$)aryl($C_1$–$C_6$)alkylaminocarbonyl($C_1$–$C_6$)alkyl, ($C_6$–$C_{10}$)arylsulfonyl, ($C_2$–$C_9$)heterocycloalkyl, ($C_2$–$C_9$)heteroaryl, ($C_2$–$C_9$)heterocycloalkyl($C_1$–$C_6$)alkyl, ($C_2$–$C_9$)heteroaryl($C_1$–$C_6$)alkyl or $R^{14}R^{15}N$($C_1$–$C_6$)alkyl wherein $R^{14}$ and $R^{15}$ are each independently ($C_1$–$C_6$)alkyl or ($C_1$–$C_6$)alkylcarbonyl;

$R^4$ is $(R^5)_f(R^6)_g$($C_6$–$C_{10}$)aryl, $(R^5)_f(R^6)_g$($C_3$–$C_{10}$)cycloalkyl, $(R^5)_f(R^7)_h$($C_2$–$C_9$)heteroaryl, or $(R^5)_f(R^7)_h$($C_2$–$C_9$)heterocycloalkyl, wherein f is 1, 2, 3 or 4;

g and h are each independently 0, 1, 2 or 3;

$R^5$ is one to three groups independently selected from ($C_2$–$C_9$)heterocycloalkylcarbonyl, ($C_2$–$C_9$)heteroarylcarbonyl, ($C_2$–$C_9$)heteroaryl($C_1$–$C_6$)alkylaminocarbonyl, ($C_2$–$C_9$)heterocycloalkyl($C_1$–$C_6$)alkylaminocarbonyl, ($C_1$–$C_6$)alkylsulfonylamino($C_1$–$C_6$)alkylaminocarbonyl, ureido($C_1$–$C_6$)alkylaminocarbonyl, ($C_1$–$C_6$)alkylureido($C_1$–$C_6$)alkylaminocarbonyl, (($C_1$–$C_6$)alkyl)$_2$ureido($C_1$–$C_6$)alkylaminocarbonyl, halo($C_1$–$C_6$)alkylaminocarbonyl, aminosulfonyl($C_1$–$C_6$)alkylaminocarbonyl, ($C_1$–$C_6$)alkylaminosulfonyl($C_1$–$C_6$)alkylaminocarbonyl, ($C_1$–$C_6$)alkylsulfonylamino($C_1$–$C_6$)alkylcarbonylamino, cyanoguanidino($C_1$–$C_6$)alkylcarbonylamino, ($C_1$–$C_6$)alkylcyanoguanidino($C_1$–$C_6$)alkylcarbonylamino, (($C_1$–$C_6$)alkyl)$_2$cyanoguanidino($C_1$–$C_6$)alkylcarbonylamino, aminocarbonyl($C_1$–$C_6$)alkylcarbonylamino, ($C_2$–$C_9$)heteroaryl($C_1$–$C_6$)alkylcarbonylamino, ($C_2$–$C_9$)heterocycloalkyl($C_1$–$C_6$)alkylcarbonylamino, aminosulfonyl($C_1$–$C_6$)alkylcarbonylamino, hydroxy($C_1$–$C_6$)alkylureido, amino($C_1$–$C_6$)alkylureido, ($C_1$–$C_6$)alkylamino($C_1$–$C_6$)alkylureido, (($C_1$–$C_6$)alkyl)$_2$amino($C_1$–$C_6$)alkylureido, ($C_2$–$C_9$)heterocycloalkyl($C_1$–$C_6$)alkylureido, ($C_2$–$C_9$)heteroaryl($C_1$–$C_6$)alkylureido, aminosulfonyl($C_1$–$C_6$)alkylureido, aminocarbonyl($C_1$–$C_6$)alkylureido, ($C_1$–$C_6$)alkylaminocarbonyl($C_1$–$C_6$)alkylureido, (($C_1$–$C_6$)alkyl)$_2$aminocarbonyl($C_1$–$C_6$)alkylureido, acetylamino($C_1$–$C_6$)alkylureido, (acetyl)(($C_1$–$C_6$)alkyl)amino($C_1$–$C_6$)alkylureido, halo($C_1$–$C_6$)alkylsulfonylamino, amino($C_1$–$C_6$)alkylsulfonylamino, ($C_1$–$C_6$)alkylamino($C_1$–$C_6$)alkylsulfonylamino, (($C_1$–$C_6$)alkyl)$_2$amino($C_1$–$C_6$)alkylsulfonylamino, acetylamino($C_1$–$C_6$)alkylsulfonylamino, (acetyl)(($C_1$–$C_6$)alkyl)amino($C_1$–$C_6$)alkylsulfonylamino, ureido($C_1$–$C_6$)alkylsulfonylamino, ($C_1$–$C_6$)alkylureido($C_1$–$C_6$)alkylsulfonylamino, (($C_1$–$C_6$)alkyl)$_2$ureido($C_1$–$C_6$)alkylsulfonylamino, ($C_1$–$C_6$)alkylsulfonylamino($C_1$–$C_6$)alkylsulfonylamino, cyanoguanidino($C_1$–$C_6$)alkylsulfonylamino, ($C_1$–$C_6$)alkylcyanoguanidino($C_1$–$C_6$)alkylsulfonylamino, (($C_1$–$C_6$)alkyl)$_2$cyanoguanidino($C_1$–$C_6$)alkylsulfonylamino, aminocarbonyl($C_1$–$C_6$)alkylsulfonylamino, ($C_1$–$C_6$)alkoxycarbonylamino($C_1$–$C_6$)alkylsulfonylamino, aminosulfonylamino, ($C_1$–$C_6$)alkylaminosulfonylamino, (($C_1$–$C_6$)alkyl)$_2$aminosulfonylamino, aminocarbonyl($C_1$–$C_6$)alkylamino($C_1$–$C_6$)alkylsulfonylamino, ($C_2$–$C_9$)heterocycloalkyloxycarbonylamino($C_1$–$C_6$)alkylsulfonylamino, ($C_2$–$C_9$)heteroaryloxycarbonylamino($C_1$–$C_6$)alkylsulfonylamino, cyanoguanidino, ($C_1$–$C_6$)alkylcyanoguanidino, (($C_1$–$C_6$)alkyl)$_2$cyanoguanidino, ($C_2$–$C_9$)heterocycloalkylcyanoguanidino, ($C_2$–$C_9$)heteroarylcyanoguanidino, ($C_2$–$C_9$)heterocycloalkyl($C_1$–$C_6$)alkylcyanoguanidino, ($C_2$–$C_9$)heteroaryl($C_1$–$C_6$)alkylcyanoguanidino, amino($C_1$–$C_6$)alkylcyanoguanidino, ($C_1$–$C_6$)alkylamino($C_1$–$C_6$)alkylcyanoguanidino, (($C_1$–$C_6$)alkyl)$_2$amino($C_1$–$C_6$)alkylcyanoguanidino, aminocarbonyl($C_1$–$C_6$)alkylcyanoguanidino, ($C_1$–$C_6$)alkylaminocarbonyl($C_1$–$C_6$)alkylcyanoguanidino, (($C_1$–$C_6$)alkyl)$_2$aminocarbonyl($C_1$–$C_6$)alkylcyanoguanidino, aminocarbonyl($C_1$–$C_6$)alkylamino, ($C_1$–$C_6$)

alkylsulfonylamino($C_1$–$C_6$)alkylamino, ($C_1$–$C_6$) alkoxycarbonylamino($C_1$–$C_6$)alkylamino, aminosulfonyl($C_1$–$C_6$)alkylamino, ($C_2$–$C_9$)heteroaryl ($C_1$–$C_6$)alkylamino, acetylamino($C_1$–$C_6$)alkylamino, (acetyl)(($C_1$–$C_6$)alkyl)amino($C_1$–$C_6$)alkylamino, ($C_1$–$C_6$)alkoxycarbonyl($C_1$–$C_6$)alkylamino($C_1$–$C_6$) alkyl, cyano($C_1$–$C_6$)alkylaminoalkyl, aminocarbonyl ($C_1$–$C_6$)alkylamino($C_1$–$C_6$)alkyl, acetylamino($C_1$–$C_6$) alkylamino($C_1$–$C_6$)alkyl, (acetyl)(($C_1$–$C_6$)alkyl)amino ($C_1$–$C_6$)alkylamino($C_1$–$C_6$)alkyl, ($C_1$–$C_6$) alkoxycarbonylamino($C_1$–$C_6$)alkylamino($C_1$–$C_6$) alkyl, ($C_2$–$C_9$)heterocycloalkyloxycarbonylamino ($C_1$–$C_6$)alkylamino($C_1$–$C_6$)alkyl, ($C_2$–$C_9$) heteroaryloxycarbonylamino($C_1$–$C_6$)alkylamino ($C_1$–$C_6$)alkyl, cyanoguanidino($C_1$–$C_6$)alkylamino ($C_1$–$C_6$)alkyl, ($C_1$–$C_6$)alkylcyanoguanidino($C_1$–$C_6$) alkylamino($C_1$–$C_6$)alkyl, (($C_1$–$C_6$)alkyl)$_2$ cyanoguanidino($C_1$–$C_6$)alkylamino($C_1$–$C_6$)alkyl, ($C_1$–$C_6$)alkylsulfonylamino($C_1$–$C_6$)alkylamino ($C_1$–$C_6$)alkyl, ureido($C_1$–$C_6$)alkylamino($C_1$–$C_6$)alkyl, ($C_1$–$C_6$)alkylureido($C_1$–$C_6$)alkylamino($C_1$–$C_6$)alkyl, (($C_1$–$C_6$)alkyl)$_2$ureido($C_1$–$C_6$)alkylamino($C_1$–$C_6$) alkyl, aminocarbonyloxy($C_1$–$C_6$)alkylamino($C_1$–$C_6$) alkyl, aminocarbonyl($C_1$–$C_6$)alkylcarbonylamino ($C_1$–$C_6$)alkyl, ($C_1$–$C_6$)alkylaminocarbonyl($C_1$–$C_6$) alkylcarbonylamino($C_1$–$C_6$)alkyl, (($C_1$–$C_6$)alkyl)$_2$ aminocarbonyl($C_1$–$C_6$)alkylcarbonylamino($C_1$–$C_6$) alkyl, aminosulfonyl($C_1$–$C_6$)alkylcarbonylamino ($C_1$–$C_6$)alkyl, ($C_2$–$C_9$) heterocycloalkyloxycarbonylamino($C_1$–$C_6$)alkyl, cyanoguanidino($C_1$–$C_6$)alkylcarbonylamino($C_1$–$C_6$) alkyl, cyano($C_1$–$C_6$)alkylcarbonylamino($C_1$–$C_6$)alkyl, amino($C_1$–$C_6$)alkylaminocarbonylamino($C_1$–$C_6$)alkyl, ($C_1$–$C_6$)alkylamino($C_1$–$C_6$)alkylaminocarbonylamino ($C_1$–$C_6$)alkyl, (($C_1$–$C_6$)alkyl)$_2$amino($C_1$–$C_6$) alkylaminocarbonylamino($C_1$–$C_6$)alkyl, hydroxy ($C_1$–$C_6$)alkylaminocarbonylamino($C_1$–$C_6$)alkyl, aminocarbonyl($C_1$–$C_6$)alkylaminocarbonylamino ($C_1$–$C_6$)alkyl, ($C_1$–$C_6$)alkylcarbonylamino($C_1$–$C_6$) alkylaminocarbonylamino($C_1$–$C_6$)alkyl, ($C_1$–$C_6$) alkylsulfonylamino($C_1$–$C_6$)alkylaminocarbonylamino ($C_1$–$C_6$)alkyl, ($C_1$–$C_6$)alkoxycarbonylamino($C_1$–$C_6$) alkylaminocarbonylamino($C_1$–$C_6$)alkyl, ($C_2$–$C_9$) heterocycloalkyloxycarbonylamino($C_1$–$C_6$) alkylaminocarbonylamino($C_1$–$C_6$)alkyl, ($C_2$–$C_9$) heteroaryloxycarbonylamino($C_1$–$C_6$) alkylaminocarbonylamino($C_1$–$C_6$)alkyl, ($C_2$–$C_9$) heterocycloalkyl($C_1$–$C_6$)alkylaminocarbonylamino ($C_1$–$C_6$)alkyl, ($C_2$–$C_9$)heteroaryl($C_1$–$C_6$) alkylaminocarbonylamino($C_1$–$C_6$)alkyl, ureido ($C_1$–$C_6$)alkylureido($C_1$–$C_6$)alkyl, ($C_1$–$C_6$)alkylureido ($C_1$–$C_6$)alkylureido($C_1$–$C_6$)alkyl, (($C_1$–$C_6$)alkyl)$_2$ ureido($C_1$–$C_6$)alkylureido($C_1$–$C_6$)alkyl, cyanoguanidino($C_1$–$C_6$)alkylureido($C_1$–$C_6$)alkyl, halo ($C_1$–$C_6$)alkylsulfonylamino($C_1$–$C_6$)alkyl, amino ($C_1$–$C_6$)alkylsulfonylamino($C_1$–$C_6$)alkyl, ($C_1$–$C_6$) alkylamino($C_1$–$C_6$)alkylsulfonylamino($C_1$–$C_6$)alkyl, (($C_1$–$C_6$)alkyl)$_2$amino($C_1$–$C_6$)alkylsulfonylamino ($C_1$–$C_6$)alkyl, acetylamino($C_1$–$C_6$)alkylsulfonylamino ($C_1$–$C_6$)alkyl, (acetyl)(($C_1$–$C_6$)alkyl)amino($C_1$–$C_6$) alkylsulfonylamino($C_1$–$C_6$)alkyl, ureido($C_1$–$C_6$) alkylsulfonylamino($C_1$–$C_6$)alkyl, ($C_1$–$C_6$)alkylureido ($C_1$–$C_6$)alkylsulfonylamino($C_1$–$C_6$)alkyl, (($C_1$–$C_6$) alkyl)$_2$ureido($C_1$–$C_6$)alkylsulfonylamino($C_1$–$C_6$)alkyl, ($C_1$–$C_6$)alkylsulfonylamino($C_1$–$C_6$) alkylsulfonylamino($C_1$–$C_6$)alkyl, cyanoguanidino ($C_1$–$C_6$)alkylsulfonylamino($C_1$–$C_6$)alkyl, ($C_1$–$C_6$) alkylcyanoguanidino($C_1$–$C_6$)alkylsulfonylamino ($C_1$–$C_6$)alkyl, (($C_1$–$C_6$)alkyl)$_2$(cyanoguanidino) ($C_1$–$C_6$)alkylsulfonylamino($C_1$–$C_6$)alkyl, aminocarbonyl($C_1$–$C_6$)alkylsulfonylamino($C_1$–$C_6$) alkyl, ($C_1$–$C_6$)alkoxycarbonylamino($C_1$–$C_6$) alkylsulfonylamino($C_1$–$C_6$)alkyl, ($C_2$–$C_9$) heterocycloalkyloxycarbonylamino($C_1$–$C_6$) alkylsulfonylamino($C_1$–$C_6$)alkyl, ($C_2$–$C_9$) heteroaryloxycarbonylamino($C_1$–$C_6$) alkylsulfonylamino($C_1$–$C_6$)alkyl, aminosulfonylamino ($C_1$–$C_6$)alkyl, ($C_1$–$C_6$)alkylaminosulfonylamino ($C_1$–$C_6$)alkyl, (($C_1$–$C_6$)alkyl)$_2$aminosulfonylamino ($C_1$–$C_6$)alkyl, cyanoguanidino($C_1$–$C_6$)alkyl, ($C_1$–$C_6$) alkyl(cyanoguanidino)($C_1$–$C_6$)alkyl, (($C_1$–$C_6$)alkyl)$_2$ (cyanoguanidino)($C_1$–$C_6$)alkyl, ($C_2$–$C_9$) heterocycloalkyl($C_1$–$C_6$)alkyl (cyanoguanidino)($C_1$–$C_6$)alkyl, ($C_2$–$C_9$) heterocycloalkyl(cyanoguanidino)amino, ($C_2$–$C_9$) heteroaryl(cyanoguanidino)($C_1$–$C_6$)alkyl, ($C_2$–$C_9$) heteroaryl($C_1$–$C_6$)alkyl(cyanoguanidino)($C_1$–$C_6$)alkyl, amino($C_1$–$C_6$)alkyl(cyanoguanidino)($C_1$–$C_6$)alkyl, ($C_1$–$C_6$)alkylamino($C_1$–$C_6$)alkyl(cyanoguanidino) ($C_1$–$C_6$)alkyl, (($C_1$–$C_6$)alkyl)$_2$amino($C_1$–$C_6$)alkyl (cyanoguanidino)($C_1$–$C_6$)alkyl, aminocarbonyl ($C_1$–$C_6$)alkyl(cyanoguanidino)($C_1$–$C_6$)alkyl, ($C_1$–$C_6$) alkylaminocarbonyl($C_1$–$C_6$)alkyl(cyanoguanidino) ($C_1$–$C_6$)alkyl, (($C_1$–$C_6$)alkyl)$_2$aminocarbonyl($C_1$–$C_6$) alkyl(cyanoguanidino)($C_1$–$C_6$)alkyl, aminosulfonyl, ($C_1$–$C_6$)alkylaminosulfonyl, (($C_1$–$C_6$)alkyl)$_2$ aminosulfonyl, ($C_2$–$C_9$)heterocycloalkylsulfonyl, amino($C_1$–$C_6$)alkylaminosulfonyl, ($C_1$–$C_6$)alkylamino ($C_1$–$C_6$)alkylaminosulfonyl, (($C_1$–$C_6$)alkyl)$_2$amino ($C_1$–$C_6$)alkylaminosulfonyl, ($C_2$–$C_9$) heteroarylaminosulfonyl, hydroxy($C_1$–$C_6$) alkylaminosulfonyl, ($C_1$–$C_6$)alkoxy($C_1$–$C_6$) alkylaminosulfonyl, ureido($C_1$–$C_6$) alkylaminosulfonyl, ($C_1$–$C_6$)alkylureido($C_1$–$C_6$) alkylaminosulfonyl, (($C_1$–$C_6$)alkyl)$_2$ureido($C_1$–$C_6$) alkylaminosulfonyl, ($C_1$–$C_6$)alkylsulfonylamino ($C_1$–$C_6$)alkylaminosulfonyl, ($C_1$–$C_6$) alkoxycarbonylamino($C_1$–$C_6$)alkylaminosulfonyl, ($C_2$–$C_9$)heterocycloalkyloxycarbonylamino($C_1$–$C_6$) alkylaminosulfonyl, ($C_2$–$C_9$) heteroaryloxycarbonylamino($C_1$–$C_6$) alkylaminosulfonyl, aminocarbonyl($C_1$–$C_6$) alkylaminosulfonyl, cyanoguanidino($C_1$–$C_6$) alkylaminosulfonyl, ($C_2$–$C_9$)heteroaryl($C_1$–$C_6$) alkylaminosulfonyl, ($C_2$–$C_9$) heterocycloalkylaminosulfonyl, $R^6$ is one to three groups independently selected from hydrogen, hydroxy, hydroxysulfonyl, halo, ($C_1$–$C_6$)alkyl, mercapto, mercapto($C_1$–$C_6$)alkyl, ($C_1$–$C_6$)alkylthio, ($C_1$–$C_6$)alkylsulfinyl, ($C_1$–$C_6$)alkylsulfonyl, ($C_6$–$C_{10}$) arylsulfonyl, ($C_1$–$C_6$)alkylthio($C_1$–$C_6$)alkyl, ($C_1$–$C_6$) alkylsulfinyl($C_1$–$C_6$)alkyl, ($C_1$–$C_6$)alkylsulfonyl ($C_1$–$C_6$)alkyl, ($C_1$–$C_6$)alkoxy, hydroxy($C_1$–$C_6$)alkoxy, ($C_6$–$C_{10}$)aryloxy, halo($C_1$–$C_6$)alkyl, trifluoro($C_1$–$C_6$) alkyl, formyl, formyl($C_1$–$C_6$)alkyl, nitro, nitroso, cyano, ($C_6$–$C_{10}$)aryl($C_1$–$C_6$)alkoxy, halo($C_1$–$C_6$) alkoxy, trifluoro($C_1$–$C_6$)alkoxy, amino($C_1$–$C_6$)alkoxy, ($C_3$–$C_{10}$)cycloalkyl, ($C_3$–$C_{10}$)cycloalkyl($C_1$–$C_6$)alkyl, hydroxy($C_3$–$C_{10}$)cycloalkyl($C_1$–$C_6$)alkyl, ($C_3$–$C_{10}$) cycloalkylamino, ($C_3$–$C_{10}$)cycloalkylamino($C_1$–$C_6$) alkyl, cyano($C_1$–$C_6$)alkyl, ($C_2$–$C_6$)alkenyl, ($C_2$–$C_6$) alkynyl, ($C_6$–$C_{10}$)aryl, ($C_6$–$C_{10}$)aryl($C_1$–$C_6$)alkyl, ($C_6$–$C_{10}$)aryl($C_2$–$C_6$)alkenyl, hydroxy($C_1$–$C_6$)alkyl, (hydroxy) ($C_6$–$C_{10}$)aryl($C_1$–$C_6$)alkyl, (($C_1$–$C_6$) alkylamino)($C_6$–$C_{10}$)aryl($C_1$–$C_6$)alkyl, hydroxy ($C_1$–$C_6$)alkylthio($C_1$–$C_6$)alkyl, hydroxy($C_2$–$C_6$) alkenyl, hydroxy($C_2$–$C_6$)alkenyl, hydroxy($C_2$–$C_6$) alkynyl, ($C_1$–$C_6$)alkoxy($C_1$–$C_6$)alkyl, ($C_1$–$C_6$)alkoxy ($C_6$–$C_{10}$)aryl($C_1$–$C_6$)alkyl, aryloxy($C_1$–$C_6$)alkyl, ($C_6$–$C_{10}$)aryl($C_1$–$C_6$)alkoxy($C_1$–$C_6$)alkyl, amino, ($C_1$–$C_6$)alkylamino, (($C_1$–$C_6$)alkyl)$_2$amino, ($C_6$–$C_{10}$)

arylamino, $(C_6-C_{10})$aryl$(C_1-C_6)$alkylamino, amino$(C_1-C_6)$alkylamino, $(C_2-C_9)$heterocycloalkylamino, $(C_2-C_9)$heteroarylamino, $(C_3-C_{10})$cycloalkyl$(C_1-C_6)$alkyl)amino, $(C_1-C_6)$alkylcarbonylamino, $(C_1-C_6)$alkoxycarbonylamino, $(C_2-C_6)$alkenylcarbonylamino, $(C_3-C_{10})$cycloalkylcarbonylamino, $(C_6-C_{10})$arylcarbonylamino, $(C_2-C_9)$heterocycloalkylcarbonylamino, halo$(C_1-C_6)$alkylcarbonylamino, $(C_1-C_6)$alkoxy$(C_1-C_6)$alkylcarbonylamino, $(C_1-C_6)$alkoxycarbonyl$(C_1-C_6)$alkylcarbonylamino, $((C_1-C_6)$alkylcarbonyl$)((C_1-C_6)$alkyl)amino, $((C_1-C_6)$alkoxycarbonyl$)((C_1-C_6)$alkyl)amino, $(C_1-C_6)$alkylsulfonylamino, amino$(C_1-C_6)$alkyl, $(C_1-C_6)$alkylamino$(C_1-C_6)$alkyl, $((C_1-C_6)$alkyl$)_2$amino$(C_1-C_6)$alkyl, hydroxy$(C_1-C_6)$alkylamino$(C_1-C_6)$alkyl, $(C_6-C_{10})$arylamino$(C_1-C_6)$alkyl, $(C_6-C_{10})$aryl$(C_1-C_6)$alkylamino$(C_1-C_6)$alkyl, $(C_1-C_6)$alkylcarbonylamino$(C_1-C_6)$alkyl, $(C_6-C_{10})$arylcarbonylamino$(C_1-C_6)$alkyl, $((C_1-C_6)$alkylcarbonyl$)((C_1-C_6)$alkyl)amino$(C_1-C_6)$alkyl, $C_3-C_{10})$cycloalkyl$(C_1-C_6)$alkyl)amino$(C_1-C_6)$alkyl, $(C_1-C_6)$alkoxycarbonylamino$(C_1-C_6)$alkyl, $(C_1-C_6)$alkoxycarbonyl$(C_1-C_6)$alkylcarbonylamino$(C_1-C_6)$alkyl, $((C_1-C_6)$alkoxycarbonyl$)((C_1-C_6)$alkyl)amino$(C_1-C_6)$alkyl, $(C_1-C_6)$alkylsulfonylamino$(C_1-C_6)$alkyl, $((C_1-C_6)$alkylsulfonyl$)((C_1-C_6)$alkyl)amino$(C_1-C_6)$alkyl, $(C_6-C_{10})$arylsulfonylamino$(C_1-C_6)$alkyl, $((C_6-C_{10})$arylsulfonyl$)((C_1-C_6)$alkyl)amino$(C_1-C_6)$alkyl, $(C_2-C_9)$heterocycloalkylamino$(C_1-C_6)$alkyl, $(C_2-C_9)$heteroarylamino$(C_1-C_6)$alkyl, $(C_1-C_6)$alkoxycarbonyl, $(C_6-C_{10})$aryl$(C_1-C_6)$alkoxycarbonyl, $(C_1-C_6)$alkylcarbonyl, $(C_6-C_{10})$arylcarbonyl, $(C_6-C_{10})$aryl$(C_1-C_6)$alkylcarbonyl, hydroxy$(C_1-C_6)$alkoxycarbonyl, $(C_1-C_6)$alkoxycarbonyl$(C_1-C_6)$alkyl, $(C_6-C_{10})$aryl$(C_1-C_6)$alkoxycarbonyl$(C_1-C_6)$alkyl, $(C_1-C_6)$alkoxy$(C_1-C_6)$alkylcarbonyloxy$(C_1-C_6)$alkyl, $((C_1-C_6)$alkyl$)_2$aminocarbonyloxy$(C_1-C_6)$alkyl, $(C_1-C_6)$alkylcarbonyl$(C_1-C_6)$alkyl, $(C_6-C_{10})$arylcarbonyl$(C_1-C_6)$alkyl, $(C_6-C_{10})$aryl$(C_1-C_6)$alkylcarbonyl$(C_1-C_6)$alkyl, aminocarbonyl, $(C_1-C_6)$alkylaminocarbonyl, $((C_1-C_6)$alkyl$)_2$aminocarbonyl, $(C_6-C_{10})$arylaminocarbony), $(C_6-C_{10})$aryl$(C_1-C_6)$alkylaminocarbonyl, (aminocarbonyl$(C_1-C_6)$alkylaminocarbonyl, $((C_1-C_6)$alkylaminocarbonyl$(C_1-C_6)$alkylaminocarbonyl, $((C_1-C_6)$alkoxycarbonyl$(C_1-C_6)$alkylaminocarbonyl, (amino$(C_1-C_6)$alkyl)aminocarbonyl, (hydroxy$(C_1-C_6)$alkylaminocarbonyl, aminocarbonyl$(C_1-C_6)$alkyl, $(C_1-C_6)$alkylaminocarbonyl$(C_1-C_6)$alkyl, $((C_1-C_6)$alkyl$)_2$aminocarbonyl$(C_1-C_6)$alkyl, $(C_6-C_{10})$arylaminocarbonyl$(C_1-C_6)$alkyl, $(C_6-C_{10})$aryl$(C_1-C_6)$alkylaminocarbonyl$(C_1-C_6)$alkyl, amidino, hydroxyamidino, guanidino, ureido, $(C_1-C_6)$alkylureido, $(C_6-C_{10})$arylureido, $((C_6-C_{10})$aryl$)_2$ureido, $(C_6-C_{10})$aryl$(C_1-C_6)$alkylureido, halo$(C_1-C_6)$alkylureido, $((C_1-C_6)$alkyl$)((C_6-C_{10})$aryl)ureido, $((C_1-C_6)$alkyl$)_2$ureido, halo$(C_1-C_6)$alkylcarbonylureido, ureido$(C_1-C_6)$alkyl, $(C_1-C_6)$alkylureido$(C_1-C_6)$alkyl, $((C_1-C_6)$alkyl$)_2$ureido$(C_1-C_6)$alkyl, $(C_6-C_{10})$arylureido$(C_1-C_6)$alkyl, $((C_6-C_{10})$aryl$)_2$ureido$(C_1-C_6)$alkyl, $(C_6-C_{10})$aryl$(C_1-C_6)$alkylureido$(C_1-C_6)$alkyl, halo$(C_1-C_6)$alkylureido$(C_1-C_6)$alkyl, (halo$(C_1-C_6)$alkyl$)((C_1-C_6)$alkyl)ureido$(C_1-C_6)$alkyl, $((C_1-C_6)$alkoxycarbonyl$(C_1-C_6)$alkyl)ureido$(C_1-C_6)$alkyl, glycinamido, $(C_1-C_6)$alkylglycinamido, aminocarbonylglycinamido, $(C_1-C_6)$alkoxycarbonylglycinamido, (aminocarbonyl$)((C_1-C_6)$alkyl)glycinamido, $((C_1-C_6)$alkoxycarbonyl$(C_1-C_6)$alkylcarbonyl$)((C_1-C_6)$alkyl)glycinamido, $((C_1-C_6)$alkoxycarbonylamino$(C_1-C_6)$alkylcarbonyl)glycinamido, $(C_6-C_{10})$arylcarbonylglycinamido, $((C_6-C_{10})$arylcarbonyl$)((C_1-C_6)$alkyl)glycinamido, $((C_6-C_{10})$aryl$(C_1-C_6)$alkylaminocarbonyl)glycinamido, $(C_6-C_{10})$aryl$(C_1-C_6)$alkylaminocarbonyl$)((C_1-C_6)$alkyl)glycinamido, $(C_6-C_{10})$arylaminocarbonylglycinamido, $((C_6-C_{10})$arylaminocarbonyl$)((C_1-C_6)$alkyl)glycinamido, glycinamido$(C_1-C_6)$alkyl, alaninamido, $(C_1-C_6)$alkylalaninamido, alaninamido$(C_1-C_6)$alkyl, $(C_2-C_9)$heteroaryl, $(C_2-C_9)$heterocycloalkyl, $(C_2-C_9)$heteroaryl$(C_1-C_6)$alkyl and $(C_2-C_9)$heterocycloalkyl$(C_1-C_6)$alkyl;

$R^7$ is one to three groups independently selected from hydrogen, hydroxy, halo, $(C_1-C_6)$alkyl, $(C_1-C_6)$alkylsulfonyl, $(C_6-C_{10})$arylsulfonyl, $(C_1-C_6)$alkoxy, hydroxy$(C_1-C_6)$alkoxy, halo$(C_1-C_6)$alkyl, formyl, nitro, cyano, halo$(C_1-C_6)$alkoxy, $(C_2-C_6)$alkenyl, $(C_2-C_6)$alkynyl, $(C_6-C_{10})$aryl, $(C_6-C_{10})$aryl$(C_1-C_6)$alkyl, amino, $(C_1-C_6)$alkylamino, $((C_1-C_6)$alkyl$)_2$amino, $(C_6-C_{10})$arylamino, $(C_6-C_{10})$aryl$(C_1-C_6)$alkylamino, $(C_1-C_6)$alkylcarbonylamino, $(C_1-C_6)$alkoxycarbonylamino, $(C_2-C_6)$alkenylcarbonylamino, cycloalkylcarbonylamino, $(C_6-C_{10})$arylcarbonylamino, halo$(C_1-C_6)$alkylcarbonylamino, $(C_1-C_6)$alkoxy$(C_1-C_6)$alkylcarbonylamino, $(C_1-C_6)$alkoxycarbonyl$(C_1-C_6)$alkylcarbonylamino, $((C_1-C_6)$alkylcarbonyl$)((C_1-C_6)$alkyl)amino, $((C_1-C_6)$alkoxycarbonyl$)((C_1-C_6)$alkyl)amino, $(C_1-C_6)$alkylsulfonylamino, amino$(C_1-C_6)$alkyl, $(C_1-C_6)$alkylamino$(C_1-C_6)$alkyl, $((C_1-C_6)$alkyl$)_2$amino$(C_1-C_6)$alkyl, $(C_1-C_6)$alkylcarbonylamino$(C_1-C_6)$alkyl, $(C_6-C_{10})$arylcarbonylamino$(C_1-C_6)$alkyl, $((C_1-C_6)$alkylcarbonyl$)((C_1-C_6)$alkyl)amino$(C_1-C_6)$alkyl, $(C_1-C_6)$alkoxycarbonylamino$(C_1-C_6)$alkyl, $(C_1-C_6)$alkoxycarbonyl, $(C_6-C_{10})$aryl$(C_1-C_6)$alkoxycarbonyl, $(C_1-C_6)$alkylcarbonyl, $(C_6-C_{10})$arylcarbonyl, $(C_6-C_{10})$aryl$(C_1-C_6)$alkylcarbonyl, aminocarbonyl, $(C_1-C_6)$alkylaminocarbonyl, $((C_1-C_6)$alkyl$)_2$aminocarbonyl, $(C_6-C_{10})$arylaminocarbonyl, aminocarbonyl$(C_1-C_6)$alkyl, $(C_1-C_6)$alkylaminocarbonyl$(C_1-C_6)$alkyl, $((C_1-C_6)$alkyl$)_2$aminocarbonyl$(C_1-C_6)$alkyl, $(C_6-C_{10})$arylaminocarbonyl$(C_1-C_6)$alkyl, guanidino, ureido, $(C_1-C_6)$alkylureido, ureido$(C_1-C_6)$alkyl, $(C_1-C_6)$alkylureido$(C_1-C_6)$alkyl, and glycinamido;

$R^9$ and $R^{10}$ are each independently selected from the group consisting of hydrogen, $(C_1-C_6)$alkyl, $(C_6-C_{10})$aryl, $(C_6-C_{10})$aryl$(C_1-C_6)$alkyl, $(C_1-C_6)$alkylcarbonyl, $(C_1-C_6)$alkylcarbonyl$(C_1-C_6)$alkyl, $(C_6-C_{10})$aryl$(C_1-C_6)$alkylcarbonyl, $(C_6-C_{10})$aryl$(C_1-C_6)$alkylcarbonyl$(C_1-C_6)$alkyl, aminocarbonyl, $(C_1-C_6)$alkylaminocarbonyl, $((C_1-C_6)$alkyl$)_2$aminocarbonyl and $(C_1-C_6)$alkoxycarbonyl; and $R^{11}$ and $R^{12}$ are each independently selected from the group consisting of hydrogen, $(C_1-C_6)$alkyl, $(C_6-C_{10})$aryl, $(C_6-C_{10})$aryl$(C_1-C_6)$alkyl, hydroxy, $(C_1-C_6)$alkoxy, hydroxy$(C_1-C_6)$alkyl, $(C_1-C_6)$alkoxy$(C_1-C_6)$alkyl, amino, $(C_1-C_6)$alkylamino, $((C_1-C_6)$alkyl$)_2$amino, $(C_1-C_6)$alkylcarbonylamino, $(C_3-C_8)$cycloalkylcarbonylamino, $(C_3-C_8)$cycloalkyl$(C_1-C_6)$alkylcarbonylamino, $(C_1-C_6)$alkoxycarbonylamino, $(C_1-C_6)$alkylsulfonylamino, $(C_6-C_{10})$arylcarbonylamino, $(C_1-C_6)$alkoxycarbonyl$(C_1-C_6)$alkylcarbonylamino, $(C_6-C_{10})$aryl$(C_1-C_6)$alkylcarbonylamino, $((C_6-C_{10})$aryl$(C_1-C_6)$alkylcarbonyl$)((C_1-C_6)$alkyl)amino, $(C_1-C_6)$alkylcarbonylamino$(C_1-C_6)$alkyl, $(C_3-C_8)$cycloalkylcarbonylamino$(C_1-C_6)$alkyl, $(C_1-C_6)$alkoxycarbonylamino$(C_1-C_6)$alkyl, $(C_2-C_9)$heterocycloalkylcarbonylamino$(C_1-C_6)$alkyl, $(C_6-C_{10})$aryl$(C_1-C_6)$alkylcarbonylamino$(C_1-C_6)$ alkyl, $(C_2-C_9)$heteroarylcarbonylamino$(C_1-C_6)$alkyl, $(C_6-C_{10})$arylsulfonylamino, $(C_1-C_6)$alkylsulfonylamino$(C_1-C_6)$alkyl, aminocarbonylamino, $(C_1-C_6)$alkylaminocarbonylamino, halo$(C_1-C_6)$alkylaminocarbonylamino, $((C_1-C_6)$alkyl$)_2$aminocarbonylamino, aminocarbonylamino$(C_1-C_6)$alkyl, $(C_1-C_6)$alkylaminocarbonylamino$(C_1-C_6)$alkyl, $((C_1-C_6)$alkyl$)_2$aminocarbonylamino$(C_1-C_6)$alkyl, halo$(C_1-C_6)$alkylaminocarbonylamino$(C_1-C_6)$alkyl, amino$(C_1-C_6)$alkyl, $(C_1-C_6)$alkylamino$(C_1-C_6)$alkyl, $((C_1-C_6)$alkyl$)_2$amino$(C_1-C_6)$alkyl, carboxy$(C_1-C_6)$alkyl, $(C_1-C_6)$alkoxycarbonyl$(C_1-C_6)$alkyl, aminocarbonyl$(C_1-C_6)$alkyl and $(C_1-C_6)$alkylaminocarbonyl$(C_1-C_6)$alkyl.

Preferred compounds of formula I include those wherein $R^1$ is hydrogen, halo, cyano, nitro, trifluoromethyl, trifluoromethoxy, $(C_1-C_6)$alkyl, hydroxy or $(C_1-C_6)$alkylcarbonyloxy.

Other preferred compounds of formula I include those wherein $R^2$ and $R^3$ are each independently selected from $(C_1-C_6)$alkyl, $(C_3-C_8)$cycloalkyl, amino$(C_1-C_6)$alkyl, amino$(C_3-C_8)$cycloalkyl, $(C_1-C_6)$alkylamino$(C_1-C_6)$alkyl, $(C_1-C_6)$alkylamino$(C_3-C_8)$cycloalkyl, hydroxy$(C_1-C_6)$alkyl, $(C_1-C_6)$alkoxycarbonylamino$(C_1-C_6)$alkyl, ureido$(C_1-C_6)$alkyl, $(C_1-C_6)$alkylureido$(C_1-C_6)$alkyl, $(C_2-C_9)$heteroaryl$(C_1-C_6)$alkyl or $(C_2-C_9)$heterocycloalkyl$(C_1-C_6)$alkyl.

Other preferred compounds of formula I include those wherein c is 1; X is C(O), d is 1; Y is $CH_2$; e is 1; and Z is oxygen.

Other preferred compounds of formula I include those wherein c is 1; X is C(O); d is 2; Y is ethylene; and e is 0.

Other preferred compounds of formula I include those wherein c is 1; X is C(O); d is 1; Y is $CH_2$; e is 1; and Z is $NR^9$ wherein $R^9$ is hydrogen or $(C_1-C_6)$alkyl.

Other preferred compounds of formula I include those wherein c is 1; X is $CH_2$; d is 1; Y is $CH_2$; e is 1; and Z is oxygen.

Other preferred compounds of formula I include those wherein c is 1; X is $CH_2$; d is 2; Y is ethylene; and e is 0.

Other preferred compounds of formula I include those wherein c is 1; X is $CH_2$; d is 1; Y is $CH_2$; e is 1, and Z is $NR^9$ wherein $R^9$ is hydrogen or $(C_1-C_6)$alkyl.

Other preferred compounds of formula I include those wherein c is 1; X is C(O); d is 1; Y is $CHR^8$ wherein $R^8$ is $NR^9R^{10}$; $R^9$ and $R^{10}$ are each independently hydrogen, $(C_1-C_6)$alkyl or $(C_1-C_6)$alkylcarbonyl; e is 1; and Z is oxygen.

Other preferred compounds of formula I include those wherein c is 1; X is C(O); d is 1; Y is $CHR^8$ wherein $R^8$ is $NR^9R^{10}$; $R^9$ and $R^{10}$ are each independently hydrogen, $(C_1-C_6)$alkyl or $(C_1-C_6)$alkylcarbonyl; e is 1; and Z is $CR^{11}R^{12}$ wherein $R^{11}$ and $R^{12}$ are hydrogen.

Other preferred compounds of formula I include those wherein c is 1; X is C(O); d is 1; Y is $CHR^8$ wherein $R^8$ is $NR^9R^{10}$; $R^9$ and $R^{10}$ are each independently hydrogen, $(C_1-C_6)$alkyl or $(C_1-C_6)$alkylcarbonyl; e is 1; and Z is $NR^9$ wherein $R^9$ is hydrogen or $(C_1-C_6)$alkyl.

Other preferred compounds of formula I include those wherein c is 1; X is $CH_2$; d is 1; Y is $CHR^8$ wherein $R^8$ is $NR^9R^{10}$; $R^9$ and $R^{10}$ are each independently hydrogen, $(C_1-C_6)$alkyl or $(C_1-C_6)$alkylcarbonyl; e is 1; and Z is oxygen.

Other preferred compounds of formula I include those wherein c is 1; X is $CH_2$; d is 1; Y is $CHR^8$ wherein $R^8$ is $NR^9R^{10}$; $R^9$ and $R^{10}$ are each independently hydrogen, $(C_1-C_6)$alkyl or $(C_1-C_6)$alkylcarbonyl; e is 1; and Z is $CR^{11}R^{12}$ wherein $R^{11}$ and $R^{12}$ are hydrogen.

Other preferred compounds of formula I include those wherein c is 1; X is $CH_2$; d is 1; Y is $CHR^8$ wherein $R^8$ is $NR^9R^{10}$; $R^9$ and $R^{10}$ are each independently hydrogen, $(C_1-C_6)$alkyl or $(C_1-C_6)$alkylcarbonyl; e is 1; and Z is $NR^9$ wherein $R^9$ is hydrogen or $(C_1-C_6)$alkyl.

Other preferred compounds of formula I include those wherein $R^4$ is $(R^5)_f(R^6)_g(C_6-C_{10})$aryl or $(R^5)_f(R^7)_h(C_2-C_9)$heteroaryl wherein f, g and h are independently 1 or 2.

Other preferred compounds of formula I include those wherein $R^5$ is $(C_2-C_9)$heterocycloalkylcarbonyl, $(C_2-C_9)$heteroarylcarbonyl, $(C_2-C_9)$heteroaryl$(C_1-C_6)$alkylaminocarbonyl, $(C_2-C_9)$heterocycloalkyl$(C_1-C_6)$alkylaminocarbonyl, $(C_1-C_6)$alkylsulfonylamino$(C_1-C_6)$alkylaminocarbonyl, ureido$(C_1-C_6)$alkylaminocarbonyl, $(C_1-C_6)$alkylureido$(C_1-C_6)$alkylaminocarbonyl, $((C_1-C_6)$alkyl$)_2$ureido$(C_1-C_6)$alkylaminocarbonyl, aminosulfonyl$(C_1-C_6)$alkylaminocarbonyl or $(C_1-C_6)$alkylaminosulfonyl$(C_1-C_6)$alkylaminocarbonyl.

Other preferred compounds of formula I include those wherein $R^5$ is $(C_1-C_6)$alkylsulfonylamino$(C_1-C_6)$alkylcarbonylamino, cyanoguanidino$(C_1-C_6)$alkylcarbonylamino, $(C_1-C_6)$alkylcyanoguanidino$(C_1-C_6)$alkylcarbonylamino, $((C_1-C_6)$alkyl$)_2$cyanoguanidino $(C_1-C_6)$alkylcarbonylamino, aminocarbonyl$(C_1-C_6)$alkylcarbonylamino, $(C_2-C_9)$heteroaryl$(C_1-C_6)$alkylcarbonylamino, $(C_2-C_9)$heterocycloalkyl$(C_1-C_6)$alkylcarbonylamino, or aminosulfonyl$(C_1-C_6)$alkylcarbonylamino.

Other preferred compounds of formula I include those wherein $R^5$ is amino$(C_1-C_6)$alkylureido, $(C_1-C_6)$alkylamino$(C_1-C_6)$alkylureido, $((C_1-C_6)$alkyl$)_2$amino$(C_1-C_6)$alkylureido, $(C_2-C_9)$heterocycloalkyl$(C_1-C_6)$alkylureido, $(C_2-C_9)$heteroaryl$(C_1-C_6)$alkylureido, aminosulfonyl$(C_1-C_6)$alkylureido, aminocarbonyl$(C_1-C_6)$alkylureido, $(C_1-C_6)$alkylaminocarbonyl$(C_1-C_6)$alkylureido, $((C_1-C_6)$alkyl$)_2$aminocarbonyl$(C_1-C_6)$alkylureido, acetylamino$(C_1-C_6)$alkylureido, (acetyl)$((C_1-C_6)$alkyl)amino$(C_1-C_6)$alkylureido.

Other preferred compounds of formula I include those wherein $R^5$ is amino$(C_1-C_6)$alkylsulfonylamino, $(C_1-C_6)$alkylamino$(C_1-C_6)$alkylsulfonylamino, $((C_1-C_6)$alkyl$)_2$amino$(C_1-C_6)$alkylsulfonylamino, acetylamino$(C_1-C_6)$alkylsulfonylamino, (acetyl)$((C_1-C_6)$alkyl)amino$(C_1-C_6)$alkylsulfonylamino, ureido$(C_1-C_6)$alkylsulfonylamino, $(C_1-C_6)$alkylureido$(C_1-C_6)$alkylsulfonylamino, $((C_1-C_6)$alkyl$)_2$ureido$(C_1-C_6)$alkylsulfonylamino, $(C_1-C_6)$alkylsulfonylamino$(C_1-C_6)$alkylsulfonylamino, cyanoguanidino$(C_1-C_6)$alkylsulfonylamino, $(C_1-C_6)$alkylcyanoguanidino$(C_1-C_6)$alkylsulfonylamino, $((C_1-C_6)$alkyl$)_2$cyanoguanidino$(C_1-C_6)$alkylsulfonylamino, aminocarbonyl$(C_1-C_6)$alkylsulfonylamino, $(C_1-C_6)$alkoxycarbonylamino$(C_1-C_6)$alkylsulfonylamino, aminosulfonylamino, $(C_1-C_6)$alkylaminosulfonylamino, $((C_1-C_6)$alkyl$)_2$aminosulfonylamino, aminocarbonyl$(C_1-C_6)$alkylamino$(C_1-C_6)$alkylsulfonylamino, $(C_2-C_9)$heterocycloalkyloxycarbonylamino$(C_1-C_6)$alkylsulfonylamino or $(C_2-C_9)$heteroaryloxycarbonylamino$(C_1-C_6)$alkylsulfonylamino.

Other preferred compounds of formula I include those wherein $R^5$ is cyanoguanidino, $(C_1-C_6)$alkylcyanoguanidino, $((C_1-C_6)$alkyl$)_2$cyanoguanidino, $(C_2-C_9)$heterocycloalkylcyanoguanidino, $(C_2-C_9)$heteroarylcyanoguanidino, $(C_2-C_9)$heterocycloalkyl$(C_1-C_6)$alkylcyanoguanidino, $(C_2-C_9)$heteroaryl$(C_1-C_6)$alkylcyanoguanidino, amino$(C_1-C_6)$alkylcyanoguanidino, $(C_1-C_6)$alkylamino$(C_1-C_6)$alkylcyanoguanidino, $((C_1-C_6)$alkyl$)_2$amino$(C_1-C_6)$alkylcyanoguanidino, aminocarbonyl$(C_1-C_6)$alkylcyanoguanidino, $(C_1-C_6)$alkylaminocarbonyl$(C_1-C_6)$alkylcyanoguanidino or $((C_1-C_6)$alkyl$)_2$aminocarbonyl$(C_1-C_6)$alkylcyanoguanidino.

Other preferred compounds of formula I include those wherein $R^5$ is aminocarbonyl$(C_1-C_6)$alkylamino, $(C_1-C_6)$alkylsulfonylamino$(C_1-C_6)$alkylamino, $(C_1-C_6)$ alkoxycarbonylamino($C_1$–$C_6$)alkylamino, aminosulfonyl ($C_1$–$C_6$)alkylamino, ($C_2$–$C_9$)heteroaryl($C_1$–$C_6$)alkylamino, acetylamino($C_1$–$C_6$)alkylamino or (acetyl)(($C_1$–$C_6$)alkyl)amino($C_1$–$C_6$)alkylamino.

Other preferred compounds of formula I include those wherein $R^5$ is cyano($C_1$–$C_6$)alkylaminoalkyl or aminocarbonyl($C_1$–$C_6$)alkylamino($C_1$–$C_6$)alkyl.

Other preferred compounds of formula I include those wherein $R^5$ is acetylamino($C_1$–$C_6$)alkylamino($C_1$–$C_6$)alkyl, (acetyl)(($C_1$–$C_6$)alkyl)amino($C_1$–$C_6$)alkylamino($C_1$–$C_6$)alkyl, ($C_1$–$C_6$)alkoxycarbonylamino($C_1$–$C_6$)alkylamino ($C_1$–$C_6$)alkyl, ($C_2$–$C_9$)heterocycloalkyloxycarbonylamino ($C_1$–$C_6$)alkylamino($C_1$–$C_6$)alkyl, ($C_2$–$C_9$)heteroaryloxycarbonylamino($C_1$–$C_6$)alkylamino($C_1$–$C_6$)alkyl, cyanoguanidino($C_1$–$C_6$)alkylamino($C_1$–$C_6$)alkyl, ($C_1$–$C_6$)alkylcyanoguanidino($C_1$–$C_6$)alkylamino($C_1$–$C_6$)alkyl, (($C_1$–$C_6$)alkyl)$_2$cyanoguanidino($C_1$–$C_6$)alkylamino ($C_1$–$C_6$)alkyl, ($C_1$–$C_6$)alkylsulfonylamino($C_1$–$C_6$)alkylamino($C_1$–$C_6$)alkyl, ureido($C_1$–$C_6$)alkylamino($C_1$–$C_6$)alkyl, ($C_1$–$C_6$)alkylureido($C_1$–$C_6$)alkylamino($C_1$–$C_6$)alkyl, (($C_1$–$C_6$)alkyl)$_2$ureido($C_1$–$C_6$)alkylamino($C_1$–$C_6$)alkyl or aminocarbonyloxy($C_1$–$C_6$)alkylamino($C_1$–$C_6$)alkyl.

Other preferred compounds of formula I include those wherein $R^5$ is acetylamino($C_1$–$C_6$)alkylcarbonylamino ($C_1$–$C_6$)alkyl, (acetyl)(($C_1$–$C_6$)alkyl)amino($C_1$–$C_6$)alkylcarbonylamino($C_1$–$C_6$)alkyl, aminocarbonyl($C_1$–$C_6$)alkylcarbonylamino($C_1$–$C_6$)alkyl, ($C_1$–$C_6$)alkylaminocarbonyl($C_1$–$C_6$)alkylcarbonylamino($C_1$–$C_6$)alkyl, (($C_1$–$C_6$)alkyl)$_2$aminocarbonyl($C_1$–$C_6$)alkylcarbonylamino($C_1$–$C_6$)alkyl, aminosulfonyl($C_1$–$C_6$)alkylcarbonylamino($C_1$–$C_6$)alkyl, ($C_2$–$C_9$)heterocycloalkyloxycarbonylamino($C_1$–$C_6$)alkyl, cyanoguanidino($C_1$–$C_6$)alkylcarbonylamino($C_1$–$C_6$)alkyl or cyano($C_1$–$C_6$)alkylcarbonylamino($C_1$–$C_6$)alkyl.

Other preferred compounds of formula I include those wherein $R^5$ is amino($C_1$–$C_6$)alkylaminocarbonylamino ($C_1$–$C_6$)alkyl, ($C_1$–$C_6$)alkylamino($C_1$–$C_6$)alkylaminocarbonyl amino($C_1$–$C_6$)alkyl, (($C_1$–$C_6$)alkyl)$_2$amino($C_1$–$C_6$)alkylaminocarbonylamino($C_1$–$C_6$)alkyl, aminocarbonyl($C_1$–$C_6$)alkylaminocarbonylamino($C_1$–$C_6$)alkyl, ($C_1$–$C_6$) alkylcarbonylamino($C_1$–$C_6$)alkylaminocarbonylamino($C_1$–$C_6$)alkyl, ($C_1$–$C_6$)alkylsulfonylamino($C_1$–$C_6$)alkylaminocarbonylamino ($C_1$–$C_6$)alkyl, ($C_1$–$C_6$)alkoxycarbonyl amino($C_1$–$C_6$)alkylaminocarbonylamino($C_1$–$C_6$)alkyl, ($C_2$–$C_9$)heterocycloalkyloxycarbonyl amino($C_1$–$C_6$)alkylaminocarbonylamino($C_1$–$C_6$)alkyl, ($C_2$–$C_9$)heteroaryloxycarbonylamino($C_1$–$C_6$)alkylaminocarbonylamino($C_1$–$C_6$)alkyl, ($C_2$–$C_9$)heterocycloalkyl($C_1$–$C_6$)alkylaminocarbonylamino($C_1$–$C_6$)alkyl, ($C_2$–$C_9$)heteroaryl($C_1$–$C_6$)alkylaminocarbonylamino($C_1$–$C_6$)alkyl, ureido($C_1$–$C_6$)alkylureido($C_1$–$C_6$)alkyl, ($C_1$–$C_6$)alkylureido($C_1$–$C_6$)alkylureido($C_1$–$C_6$)alkyl, (($C_1$–$C_6$)alkyl)$_2$ureido($C_1$–$C_6$)alkylureido($C_1$–$C_6$)alkyl or cyanoguanidino($C_1$–$C_6$)alkylureido($C_1$–$C_6$)alkyl.

Other preferred compounds of formula I include those wherein $R^5$ is amino($C_1$–$C_6$)alkylsulfonylamino($C_1$–$C_6$)alkyl, ($C_1$–$C_6$)alkylamino($C_1$–$C_6$)alkylsulfonylamino ($C_1$–$C_6$)alkyl, (($C_1$–$C_6$)alkyl)$_2$amino($C_1$–$C_6$)alkylsulfonylamino($C_1$–$C_6$)alkyl, acetylamino($C_1$–$C_6$)alkylsulfonylamino($C_1$–$C_6$)alkyl, (acetyl)(($C_1$–$C_6$)alkyl)amino($C_1$–$C_6$)alkylsulfonylamino($C_1$–$C_6$)alkyl, ureido ($C_1$–$C_6$)alkylsulfonylamino($C_1$–$C_6$)alkyl, ($C_1$–$C_6$)alkylureido($C_1$–$C_6$)alkylsulfonylamino($C_1$–$C_6$)alkyl, (($C_1$–$C_6$)alkyl)$_2$ureido($C_1$–$C_6$)alkylsulfonylamino($C_1$–$C_6$)alkyl, ($C_1$–$C_6$)alkylsulfonylamino($C_1$–$C_6$)alkylsulfonylamino($C_1$–$C_6$)alkyl, cyanoguanidino($C_1$–$C_6$)alkylsulfonylamino($C_1$–$C_6$)alkyl, ($C_1$–$C_6$)alkyl(cyanoguanidino)($C_1$–$C_6$)alkylsulfonylamino($C_1$–$C_6$)alkyl, (($C_1$–$C_6$)alkyl)$_2$(cyanoguanidino)($C_1$–$C_6$)alkylsulfonylamino($C_1$–$C_6$)alkyl, aminocarbonyl($C_1$–$C_6$)alkylsulfonylamino($C_1$–$C_6$)alkyl, ($C_1$–$C_6$)alkoxycarbonylamino($C_1$–$C_6$)alkylsulfonylamino($C_1$–$C_6$)alkyl, ($C_2$–$C_9$)heterocycloalkyloxycarbonylamino($C_1$–$C_6$)alkylsulfonylamino($C_1$–$C_6$)alkyl, ($C_2$–$C_9$)heteroaryloxycarbonylamino($C_1$–$C_6$)alkylsulfonylamino($C_1$–$C_6$)alkyl, aminosulfonylamino($C_1$–$C_6$)alkyl, ($C_1$–$C_6$)alkylaminosulfonylamino($C_1$–$C_6$)alkyl or (($C_1$–$C_6$)alkyl)$_2$aminosulfonylamino($C_1$–$C_6$)alkyl.

Other preferred compounds of formula I include those wherein $R^5$ is cyanoguanidino($C_1$–$C_6$)alkyl, ($C_1$–$C_6$)alkyl(cyanoguanidino)($C_1$–$C_6$)alkyl, (($C_1$–$C_6$)alkyl)$_2$(cyanoguanidino)($C_1$–$C_6$)alkyl, ($C_2$–$C_9$)heterocycloalkyl(cyanoguanidino)($C_1$–$C_6$)alkyl, ($C_2$–$C_9$)heteroaryl(cyanoguanidino)($C_1$–$C_6$)alkyl, ($C_2$–$C_9$)heterocycloalkyl($C_1$–$C_6$)alkyl(cyanoguanidino)($C_1$–$C_6$)alkyl, ($C_2$–$C_9$)heteroaryl($C_1$–$C_6$)alkyl(cyanoguanidino)($C_1$–$C_6$)alkyl, amino($C_1$–$C_6$)alkyl(cyanoguanidino)($C_1$–$C_6$)alkyl, ($C_1$–$C_6$)alkylamino($C_1$–$C_6$)alkyl(cyanoguanidino)($C_1$–$C_6$)alkyl, (($C_1$–$C_6$)alkyl)$_2$amino($C_1$–$C_6$)alkyl(cyanoguanidino)($C_1$–$C_6$)alkyl, aminocarbonyl($C_1$–$C_6$)alkyl(cyanoguanidino)($C_1$–$C_6$)alkyl, ($C_1$–$C_6$)alkylaminocarbonyl($C_1$–$C_6$)alkyl(cyanoguanidino)($C_1$–$C_6$)alkyl or (($C_1$–$C_6$)alkyl)$_2$aminocarbonyl($C_1$–$C_6$)alkyl(cyanoguanidino)($C_1$–$C_6$)alkyl.

Other preferred compounds of formula I include those wherein $R^5$ is ($C_2$–$C_9$)heterocycloalkylsulfonyl, amino($C_1$–$C_6$)alkylaminosulfonyl, ($C_1$–$C_6$)alkylamino($C_1$–$C_6$)alkylaminosulfonyl, (($C_1$–$C_6$)alkyl)$_2$amino($C_1$–$C_6$)alkylaminosulfonyl, ($C_2$–$C_9$)heteroarylaminosulfonyl, ureido($C_1$–$C_6$)alkylaminosulfonyl, ($C_1$–$C_6$)alkylureido($C_1$–$C_6$)alkylaminosulfonyl, (($C_1$–$C_6$)alkyl)$_2$ureido($C_1$–$C_6$)alkylaminosulfonyl, ($C_1$–$C_6$)alkylsulfonylamino($C_1$–$C_6$)alkylaminosulfonyl, ($C_1$–$C_6$)alkoxycarbonylamino($C_1$–$C_6$)alkylaminosulfonyl, ($C_2$–$C_9$)heterocycloalkyloxycarbonylamino($C_1$–$C_6$)alkylaminosulfonyl, ($C_2$–$C_9$)heteroaryloxycarbonylamino($C_1$–$C_6$)alkylaminosulfonyl, aminocarbonyl($C_1$–$C_6$)alkylaminosulfonyl, cyanoguanidino($C_1$–$C_6$)alkylaminosulfonyl, ($C_2$–$C_9$)heteroaryl($C_1$–$C_6$)alkylaminosulfonyl, ($C_2$–$C_9$)heterocycloalkylaminosulfonyl, Other preferred compounds of formula I include those wherein $R^5$ is halo($C_1$–$C_6$)alkylaminocarbonyl, hydroxy($C_1$–$C_6$)alkylureido, halo($C_1$–$C_6$)alkylsulfonylamino, ($C_1$–$C_6$)alkoxycarbonyl($C_1$–$C_6$)alkylamino($C_1$–$C_6$)alkyl, hydroxy($C_1$–$C_6$)alkylaminocarbonylamino($C_1$–$C_6$)alkyl, halo($C_1$–$C_6$)alkylsulfonylamino($C_1$–$C_6$)alkyl, aminosulfonyl, ($C_1$–$C_6$)alkylaminosulfonyl, (($C_1$–$C_6$)alkyl)$_2$aminosulfonyl, hydroxy($C_1$–$C_6$)alkylaminosulfonyl, and ($C_1$–$C_6$)alkoxy($C_1$–$C_6$)alkylaminosulfonyl.

Other preferred compounds of formula I include those wherein $R^6$ and $R^7$ are each independently halo, halo($C_1$–$C_6$)alkyl, ($C_1$–$C_6$)alkyl, ($C_1$–$C_6$)alkoxy, trifluoromethyl, trifluoromethoxy, hydroxy, aminocarbonyl, cyano, ureido, ($C_1$–$C_6$)alkylsulfonylamino, ($C_1$–$C_6$)alkoxycarbonylamino or glycinamino.

The present invention also relates to the pharmaceutically acceptable acid addition salts of compounds of the formula I. The acids which are used to prepare the pharmaceutically acceptable acid addition salts of the aforementioned base compounds of this invention are those which form non-toxic acid addition salts, i.e., salts containing pharmacologically acceptable anions, such as the hydrochloride, hydrobromide, hydroiodide, nitrate, sulfate, bisulfate, phosphate, acid phosphate, acetate, lactate, citrate, acid citrate, tartrate, bitartrate, succinate, maleate, fumarate, gluconate, saccharate, benzoate, methanesulfonate, ethanesulfonate, benzenesulfonate, p-toluenesulfonate and pamoate [i.e., 1,1'-methylene-bis-(2-hydroxy-3-naphthoate)]salts.

The invention also relates to base addition salts of formula I. The chemical bases that may be used as reagents to prepare pharmaceutically acceptable base salts of those compounds of formula I that are acidic in nature are those that form non-toxic base salts with such compounds. Such non-toxic base salts include, but are not limited to those derived from such pharmacologically acceptable cations such as alkali metal cations (e.g., potassium and sodium) and alkaline earth metal cations (e.g., calcium and magnesium), ammonium or water-soluble amine addition salts such as N-methylglucamine-(meglumine), and the lower alkanolammonium and other base salts of pharmaceutically acceptable organic amines.

The compounds of this invention may contain olefin-like double bonds. When such bonds are present, the compounds of the invention exist as cis and trans configurations and as mixtures thereof.

The present invention also relates to compounds of formula I wherein any of the hydrogens may optionally be replaced by deuterium.

Unless otherwise indicated, the alkyl, alkenyl and alkynyl groups referred to herein, as well as the alkyl moieties of other groups referred to herein (e.g., alkoxy), may be linear or branched, and they may also be cyclic (e.g., cyclopropyl, cyclobutyl, cyclopentyl, cyclohexyl or cycloheptyl) or be linear or branched and contain cyclic moieties. Unless otherwise indicated, halogen includes fluorine, chlorine, bromine, and iodine.

$(C_3-C_{10})$Cycloalkyl when used herein refers to cycloalkyl groups containing zero to two levels of unsaturation such as cyclopropyl, cyclobutyl, cyclopentyl, cyclopentenyl, cyclohexyl, cyclohexenyl, 1,3-cyclohexadiene, cycloheptyl, cycloheptenyl, bicyclo[3.2.1]octane, norbornanyl etc.

$(C_2-C_9)$Heterocycloalkyl when used herein refers to pyrrolidinyl, tetrahydrofuranyl, dihydrofuranyl, tetrahydropyranyl, pyranyl, thiopyranyl, aziridinyl, oxiranyl, methylenedioxyl, chromenyl, barbituryl, isoxazolidinyl, 1,3-oxazolidin-3-yl, isothiazolidinyl, 1,3-thiazolidin-3-yl, 1,2-pyrazolidin-2-yl, 1,3-pyrazolidin-1-yl, piperidinyl, thiomorpholinyl, 1,2-tetrahydrothiazin-2-yl, 1,3-tetrahydrothiazin-3-yl, tetrahydrothiadiazinyl, morpholinyl, 1,2-tetrahydrodiazin-2-yl, 1,3-tetrahydrodiazin-1-yl, tetrahydroazepinyl, piperazinyl, or chromanyl.

$(C_2-C_9)$Heteroaryl when used herein refers to furyl, thienyl, thiazolyl, pyrazolyl, isothiazolyl, oxazolyl, isoxazolyl, pyrrolyl, triazolyl, tetrazolyl, imidazolyl, 1,3,5-oxadiazolyl, 1,2,4-oxadiazolyl, 1,2,3-oxadiazolyl, 1,3,5-thiadiazolyl, 1,2,3-thiadiazolyl, 1,2,4-thiadiazolyl, pyridyl, pyrimidyl, pyrazinyl, pyridazinyl, 1,2,4-triazinyl, 1,2,3-triazinyl, 1,3,5-triazinyl, pyrazolo[3,4-b]pyridinyl, cinnolinyl, pteridinyl, purinyl, 6,7-dihydro-5H-[1]pyrindinyl, benzo[b]thiophenyl, 5,6,7,8-tetrahydroquinolin-3-yl, benzoxazolyl, benzothiazolyl, benzisothiazolyl, benzisoxazolyl, benzimidazolyl, thianaphthenyl, isothianaphthenyl, benzofuranyl, isobenzofuranyl, isoindolyl, indolyl, indolizinyl, indazolyl, isoquinolyl, quinolyl, phthalazinyl, quinoxalinyl, quinazolinyl, or benzoxazinyl.

Aryl when used herein refers to phenyl or naphthyl.

The term "ureido", as used herein, refers to an "aminocarbonyl-amino" moiety.

The term "acetyl", as used herein, refers to an "alkylcarbonyl" moiety wherein alkyl is defined as above.

The term "cyanoguanidino", as used herein, refers to a functional group having the following formula

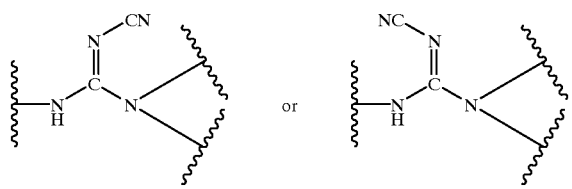

The term "$(C_2-C_9)$heterocycloalkyl(C=N—CN)amino", as used herein refers to a functional group having the following formula

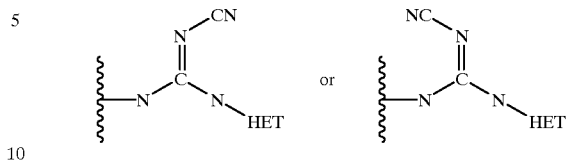

wherein "HET" refers to a $(C_2-C_9)$heterocyloalkyl or $(C_2-C_9)$heteroaryl group and the nitrogen of said group is the place of attachment.

The term "mercapto", as used herein, refers to a "HS-" moeity.

The compounds of this invention include all conformational isomers (e.g., cis and trans isomers) and all optical isomers of compounds of the formula I (e.g., enantiomers and diastereomers), as well as racemic, diastereomeric and other mixtures of such isomers.

The present invention also relates to a pharmaceutical composition for treating or preventing a disorder or condition selected from autoimmune diseases, rheumatoid arthritis, recent onset type I diabetes, lupus, inflammatory bowel disease, optic neuritis, psoriasis, multiple sclerosis, polymyalgia rheumatica, uveitis, vasculitis, acute and chronic inflammatory conditions, osteoarthritis, adult Respiratory Distress Syndrome, Respiratory Distress Syndrome of infancy, ischemia reperfusion injury, glomerulonephritis, allergic conditions, asthma, atopic dermatitis, infection associated with inflammation, viral inflammation, influenza, hepatitis, Guillian-Barre, chronic bronchitis, xenotransplantation, chronic and acute transplantation tissue rejection, chronic and acute organ transplant rejection, atherosclerosis, restenosis, HIV infectivity, granulomatous diseases, sarcoidosis, leprosy and tuberculosis and sequelae associated with certain cancers such as multiple myeloma. Compounds in this series may also limit the production of cytokines at inflammatory sites, including but not limited to TNF and IL-1, as a consequence of decreasing cell infiltration, providing benefit for diseases linked to TNF and IL-1, including congestive heart failure, pulmonary emphysema or dyspnea associated therewith, emphysema; HIV-1, HIV-2, HIV-3; cytomegalovirus (CMV), adenoviruses, Herpes viruses (Herpes zoster and Herpes simplex). They may also provide benefit for the sequelae associated with infection where such infection induces production of detrimental inflammatory cytokines such as TNF e.g, fungal meningitis, joint tissue damage, hyperplasia, pannus formation and bone resorption, psoriatic arthritis, hepatic failure, bacterial meningitis, Kawasaki syndrome, myocardial infarction, acute liver failure, lyme disease, septic shock, cancer, trauma, and malaria in a mammal, preferably a human, comprising an amount of a compound of the formula I or a pharmaceutically acceptable salt thereof effective in treating or preventing such disorder or condition and a pharmaceutically acceptable carrier.

The present invention also relates to a pharmaceutical composition for treating or preventing a disorder or condition that can be treated or prevented by inhibiting chemokine binding to the receptor CCR1 in a mammal, preferably a human, comprising an amount of a compound of the formula I, or a pharmaceutically acceptable salt thereof, effective in treating or preventing such disorder or condition and a pharmaceutically acceptable carrier Examples of such disorders and conditions are those enumerated in the preceding paragraph.

The present invention also relates to a method for treating or preventing a disorder or condition selected from autoimmune diseases, rheumatoid arthritis, recent onset type I diabetes, lupus, inflammatory bowel disease, optic neuritis, psoriasis, multiple sclerosis, polymyalgia rheumatica, uveitis, vasculitis, acute and chronic inflammatory conditions, osteoarthritis, adult Respiratory Distress Syndrome, Respiratory Distress Syndrome of infancy, ischemia reperfusion injury, glomerulonephritis, allergic conditions, asthma, atopic dermatitis, infection associated with inflammation, viral inflammation, influenza, hepatitis, Guillian-Barre, chronic bronchitis, xeno-transplantation, chronic and acute transplantation tissue rejection, chronic and acute organ transplant rejection, atherosclerosis, restenosis, HIV infectivity, granulomatous diseases, sarcoidosis, leprosy and tuberculosis and sequelae associated with certain cancers such as multiple myeloma. Compounds in this series may also limit the production of cytokines at inflammatory sites, including but not limited to TNF and IL-1, as a consequence of decreasing cell infiltration, providing benefit for diseases linked to TNF and IL-1, including congestive heart failure, pulmonary emphysema or dyspnea associated therewith, emphysema; HIV-1, HIV-2, HIV-3; cytomegalovirus (CMV), adenoviruses, Herpes viruses (Herpes zoster and Herpes simplex). They may also provide benefit for the sequelae associated with infection where such infection induces production of detrimental inflammatory cytokines such as TNF e.g, fungal meningitis, joint tissue damage, hyperplasia, pannus formation and bone resorption, psoriatic arthritis, hepatic failure, bacterial meningitis, Kawasaki syndrome, myocardial infarction, acute liver failure, lyme disease, septic shock, cancer, trauma, and malaria in a mammal, preferably a human, comprising administering to a mammal in need of such treatment or prevention an amount of a compound of the formula I, or a pharmaceutically acceptable salt thereof, that is effective in treating or preventing such disorder or condition.

The present invention also relates to a method for treating or preventing a disorder or condition that can be treated or prevented by antagonizing the CCR1 receptor in a mammal, preferably a human, comprising administering to a mammal in need of such treatment or prevention an amount of a compound of the formula I, or a pharmaceutically acceptable salt thereof, that is effective in treating or preventing such disorder or condition.

The present invention also relates to a pharmaceutical composition for treating or preventing a disorder or condition selected from autoimmune diseases, rheumatoid arthritis, recent onset type I diabetes, lupus, inflammatory bowel disease, optic neuritis, psoriasis, multiple sclerosis, polymyalgia rheumatica, uveitis, vasculitis, acute and chronic inflammatory conditions, osteoarthritis, adult Respiratory Distress Syndrome, Respiratory Distress Syndrome of infancy, ischemia reperfusion injury, glomerulonephritis, allergic conditions, asthma, atopic dermatitis, infection associated with inflammation, viral inflammation, influenza, hepatitis, Guillian-Barre, chronic bronchitis, xeno-transplantation, chronic and acute transplantation tissue rejection, chronic and acute organ transplant rejection, atherosclerosis, restenosis, HIV infectivity, granulomatous diseases, sarcoidosis, leprosy and tuberculosis and sequelae associated with certain cancers such as multiple myeloma. Compounds in this series may also limit the production of cytokines at inflammatory sites, including but not limited to TNF and IL-1, as a consequence of decreasing cell infiltration, providing benefit for diseases linked to TNF and IL-1, including congestive heart failure, pulmonary emphysema or dyspnea associated therewith, emphysema; HIV-1, HIV-2, HIV-3; cytomegalovirus (CMV), adenoviruses, Herpes viruses (Herpes zoster and Herpes simplex). They may also provide benefit for the sequelae associated with infection where such infection induces production of detrimental inflammatory cytokines such as TNF e.g, fungal meningitis, joint tissue damage, hyperplasia, pannus formation and bone resorption, psoriatic arthritis, hepatic failure, bacterial meningitis, Kawasaki syndrome, myocardial infarction, acute liver failure, lyme disease, septic shock, cancer, trauma, and malaria in a mammal, preferably a human, comprising a CCR1 receptor antagonizing effective amount of a compound of the formula I, or a pharmaceutically acceptable salt thereof, and a pharmaceutically acceptable carrier.

The present invention also relates to a pharmaceutical composition for treating or preventing a disorder or condition that can be treated or prevented by antagonizing the CCR1 receptor in a mammal, preferably a human, comprising a CCR1 receptor antagonizing effective amount of a compound of the formula I, or a pharmaceutically acceptable salt thereof, and a pharmaceutically acceptable carrier.

The present invention also relates to a method for treating or preventing a disorder or condition selected from autoimmune diseases, rheumatoid arthritis, recent onset type I diabetes, lupus, inflammatory bowel disease, optic neuritis, psoriasis, multiple sclerosis, polymyalgia rheumatica, uveitis, vasculitis, acute and chronic inflammatory conditions, osteoarthritis, adult Respiratory Distress Syndrome, Respiratory Distress Syndrome of infancy, ischemia reperfusion injury, glomerulonephritis, allergic conditions, asthma, atopic dermatitis, infection associated with inflammation, viral inflammation, influenza, hepatitis, Guillian-Barre, chronic bronchitis, xeno-transplantation, chronic and acute transplantation tissue rejection, chronic and acute organ transplant rejection, atherosclerosis, restenosis, HIV infectivity, granulomatous diseases, sarcoidosis, leprosy and tuberculosis and sequelae associated with certain cancers such as multiple myeloma. Compounds in this series may also limit the production of cytokines at inflammatory sites, including but not limited to TNF and IL-1, as a consequence of decreasing cell infiltration, providing benefit for diseases linked to TNF and IL-1, including congestive heart failure, pulmonary emphysema or dyspnea associated therewith, emphysema; HIV-1, HIV-2, HIV-3; cytomegalovirus (CMV), adenoviruses, Herpes viruses (Herpes zoster and Herpes simplex). They may also provide benefit for the sequelae associated with infection where such infection induces production of detrimental inflammatory cytokines such as TNF e.g, fungal meningitis, joint tissue damage, hyperplasia, pannus formation and bone resorption, psoriatic arthritis, hepatic failure, bacterial meningitis, Kawasaki syndrome, myocardial infarction, acute liver failure, lyme disease, septic shock, cancer, trauma, and malaria in a mammal, preferably a human, comprising administering to a mammal in need of such treatment or prevention a CCR1 receptor antagonizing effective amount of a compound of formula I, or a pharmaceutically acceptable salt thereof.

DETAILED DESCRIPTION OF THE INVENTION

The following reaction Schemes illustrate the preparation of the compounds of the present invention. Unless otherwise indicated a, b, c, d, e, j, $R^1$, $R^2$, $R^3$ and $R^4$ in the reaction Schemes and the discussion that follow are defined as above.

$R^{16}$ and $R^{17}$ together with the nitrogen to which they are attached is selected from the group consisting of amino, amino($C_1$–$C_6$)alkylcarbonylamino, ($C_1$–$C_6$)alkylamino ($C_1$–$C_6$)alkylcarbonylamino (($C_1$–$C_6$)alkyl)$_2$amino($C_1$–$C_6$) alkylcarbonylamino, acetylamino($C_1$–$C_6$) alkylcarbonylamino, (acetyl)(($C_1$–$C_6$)alkyl)amino($C_1$–$C_6$) alkylcarbonylamino, ($C_1$–$C_6$)alkylsulfonylamino($C_1$–$C_6$) alkylcarbonylamino, cyanoguanidino($C_1$–$C_6$) alkylcarbonylamino, ($C_1$–$C_6$)alkylcyanoguanidino($C_1$–$C_6$) alkylcarbonylamino, (($C_1$–$C_6$)alkyl)$_2$cyanoguanidino ($C_1$–$C_6$)alkylcarbonylamino, aminocarbonyl($C_1$–$C_6$)

alkylcarbonylamino, aminocarbonylamino($C_1$–$C_6$) alkylcarbonylamino, ($C_1$–$C_6$)alkylaminocarbonylamino ($C_1$–$C_6$)alkylcarbonylamino (($C_1$–$C_6$)alkyl)$_2$ aminocarbonylamino($C_1$–$C_6$)alkylcarbonylamino, ($C_2$–$C_9$) heteroaryl($C_1$–$C_6$)alkylcarbonylamino, ($C_2$–$C_9$) heterocycloalkyl($C_1$–$C_6$)alkylcarbonylamino, aminosulfonyl($C_1$–$C_6$)alkylcarbonylamino, hydroxy ($C_1$–$C_6$)alkylureido, (amino($C_1$–$C_6$)alkylureido, ($C_1$–$C_6$)alkylamino($C_1$–$C_6$)alkylureido, (($C_1$–$C_6$)alkyl)$_2$amino ($C_1$–$C_6$)alkylureido, ($C_2$–$C_9$)heterocycloalkyl($C_1$–$C_6$) alkylureido, ($C_2$–$C_9$)heteroaryl($C_1$–$C_6$)alkylureido, aminosulfonyl($C_1$–$C_6$)alkylureido, aminocarbonyl($C_1$–$C_6$) alkylureido, ($C_1$–$C_6$)alkylaminocarbonyl($C_1$–$C_6$) alkylureido, (($C_1$–$C_6$)alkyl)$_2$aminocarbonyl($C_1$–$C_6$) alkylureido, acetylamino($C_1$–$C_6$)alkylureido, (acetyl) (($C_1$–$C_6$)alkyl)amino($C_1$–$C_6$)alkylureido, carboxy($C_1$–$C_6$) alkylureido, halo($C_1$–$C_6$)alkylsulfonylamino, amino ($C_1$–$C_6$)alkylsulfonylamino, ($C_1$–$C_6$)alkylamino($C_1$–$C_6$) alkylsulfonylamino, (($C_1$–$C_6$)alkyl)$_2$amino($C_1$–$C_6$) alkylsulfonylamino, acetylamino($C_1$–$C_6$) alkylsulfonylamino, (acetyl)(($C_1$–$C_6$)alkyl)amino($C_1$–$C_6$) alkylsulfonylamino, ureido($C_1$–$C_6$)alkylsulfonylamino, ($C_1$–$C_6$)alkylureido($C_1$–$C_6$)alkylsulfonylamino, (($C_1$–$C_6$) alkyl)$_2$ureido($C_1$–$C_6$)alkylsulfonylamino, ($C_1$–$C_6$) alkylsulfonylamino($C_1$–$C_6$)alkylsulfonylamino, cyanoguanidino($C_1$–$C_6$)alkylsulfonylamino ($C_1$–$C_6$) alkylcyanoguanidino($C_1$–$C_6$)alkylsulfonylamino, (($C_1$–$C_6$) alkyl)$_2$cyanoguanidino($C_1$–$C_6$)alkylsulfonylamino, aminocarbonyl($C_1$–$C_6$)alkylsulfonylamino, ($C_1$–$C_6$) alkoxycarbonylamino($C_1$–$C_6$)alkylsulfonylamino, aminosulfonylamino, ($C_1$–$C_6$)alkylaminosulfonylamino, (($C_1$–$C_6$)alkyl)$_2$aminosulfonylamino, aminocarbonyl ($C_1$–$C_6$)alkylamino($C_1$–$C_6$)alkylsulfonylamino, ($C_2$–$C_9$) heterocycloalkyloxycarbonylamino($C_1$–$C_6$) alkylsulfonylamino ($C_2$–$C_9$)heteroaryloxycarbonylamino ($C_1$–$C_6$)alkylsulfonylamino, cyanoguanidino, ($C_1$–$C_6$) alkylcyanoguanidino, (($C_1$–$C_6$)alkyl)$_2$cyanoguanidino, ($C_2$–$C_9$)heterocycloalkylcyanoguanidino, ($C_2$–$C_9$) heteroarylcyanoguanidino, ($C_2$–$C_9$)heterocycloalkyl ($C_1$–$C_6$)alkylcyanoguanidino, ($C_2$–$C_9$)heteroaryl($C_1$–$C_6$) alkylcyanoguanidino, amino($C_1$–$C_6$)alkylcyanoguanidino, ($C_1$–$C_6$)alkylamino($C_1$–$C_6$)alkylcyanoguanidino, (($C_1$–$C_6$) alkyl)$_2$amino($C_1$–$C_6$)alkylcyanoguanidino, aminocarbonyl ($C_1$–$C_6$)alkylcyanoguanidino, ($C_1$–$C_6$)alkylaminocarbonyl ($C_1$–$C_6$)alkylcyanoguanidino, (($C_1$–$C_6$)alkyl)$_2$ aminocarbonyl($C_1$–$C_6$)alkylcyanoguanidino, hydroxy ($C_1$–$C_6$)alkylamino, aminocarbonyl($C_1$–$C_6$)alkylamino, carboxy($C_1$–$C_6$)alkylamino, ($C_1$–$C_6$)alkylsulfonylamino ($C_1$–$C_6$)alkylamino, ($C_1$–$C_6$)alkoxycarbonylamino($C_1$–$C_6$) alkylamino, aminosulfonyl($C_1$–$C_6$)alkylamino, ($C_2$–$C_9$) heteroaryl($C_1$–$C_6$)alkylamino, acetylamino($C_1$–$C_6$) alkylamino, (acetyl)(($C_1$–$C_6$)alkyl)amino($C_1$–$C_6$) alkylamino, ($C_1$–$C_6$)alkylamino, (($C_1$–$C_6$)alkyl)$_2$amino, ($C_6$–$C_{10}$)arylamino, ($C_6$–$C_{10}$)aryl($C_1$–$C_6$)alkylamino, amino($C_1$–$C_6$)alkylamino, ($C_2$–$C_9$)heterocycloalkylamino, ($C_2$–$C_9$)heteroarylamino, ($C_3$–$C_{10}$)cycloalkyl($C_1$–$C_6$)alkyl amino, ($C_1$–$C_6$)alkylcarbonylamino, ($C_1$–$C_6$) alkoxycarbonylamino, ($C_2$–$C_6$)alkenylcarbonylamino, ($C_3$–$C_{10}$)cycloalkylcarbonylamino, ($C_6$–$C_{10}$) arylcarbonylamino, ($C_2$–$C_9$) heterocycloalkylcarbonylamino, halo($C_1$–$C_6$) alkylcarbonylamino, ($C_1$–$C_6$)alkoxy($C_1$–$C_6$) alkylcarbonylamino, ($C_1$–$C_6$)alkoxycarbonyl($C_1$–$C_6$) alkylcarbonylamino, (($C_1$–$C_6$)alkylcarbonyl)(($C_1$–$C_6$)alkyl) amino, (($C_1$–$C_6$)alkoxycarbonyl)(($C_1$–$C_6$)alkyl)amino, ($C_1$–$C_6$)alkylsulfonylamino, ($C_3$–$C_{10}$)cycloalkylamino, ureido, ($C_1$–$C_6$)alkylureido, ($C_6$–$C_{10}$)arylureido, (($C_6$–$C_{10}$) aryl)$_2$ureido, ($C_6$–$C_{10}$)aryl($C_1$–$C_6$)alkylureido, halo($C_1$–$C_6$) alkylureido, (($C_1$–$C_6$)alkyl)(($C_6$–$C_{10}$)aryl)ureido, (($C_1$–$C_6$) alkyl)$_2$ureido, halo($C_1$–$C_6$)alkylcarbonylureido, glycinamido, ($C_1$–$C_6$)alkylglycinamido, aminocarbonylglycinamido, ($C_1$–$C_6$)alkoxy($C_1$–$C_6$) alkylcarbonylglycinamido, (aminocarbonyl)(($C_1$–$C_6$)alkyl) glycinamido, (($C_1$–$C_6$)alkoxycarbonyl($C_1$–$C_6$) alkylcarbonyl)(($C_1$–$C_6$)alkyl)glycinamido, (($C_1$–$C_6$) alkoxycarbonylamino($C_1$–$C_6$)alkylcarbonyl)glycinamido, ($C_6$–$C_{10}$)arylcarbonylglycinamido, (($C_6$–$C_{10}$)arylcarbonyl) (($C_1$–$C_6$)alkyl)glycinamido, (($C_6$–$C_{10}$)aryl($C_1$–$C_6$) alkylaminocarbonyl)glycinamido, ($C_6$–$C_{10}$)aryl($C_1$–$C_6$) alkylaminocarbonyl)(($C_1$–$C_6$)alkyl)glycinamido, ($C_6$–$C_{10}$) arylaminocarbonylglycinamido and (($C_6$–$C_{10}$) arylaminocarbonyl)(($C_1$–$C_6$)alkyl)glycinamido.

$R^{18}$ and $R^{19}$ together with the nitrogen to which they are attached is selected from the group consisting of ($C_2$–$C_9$) heteroaryl($C_1$–$C_6$)alkylamino, ($C_2$–$C_9$)heterocycloalkyl ($C_1$–$C_6$)alkylamino, ($C_1$–$C_6$)alkylsulfonylamino, ($C_1$–$C_6$) alkylsulfonylamino($C_1$–$C_6$)alkylamino, ureido($C_1$–$C_6$) alkylamino, ($C_1$–$C_6$)alkylureido($C_1$–$C_6$)alkylamino, (($C_1$–$C_6$)alkyl)$_2$ureido($C_1$–$C_6$)alkylamino, halo($C_1$–$C_6$) alkylamino, aminosulfonyl($C_1$–$C_6$)alkylamino, ($C_1$–$C_6$) alkylaminosulfonyl($C_1$–$C_6$)alkylamino, carboxy($C_1$–$C_6$) alkylamino, ($C_1$–$C_6$)alkoxycarbonyl($C_1$–$C_6$)alkylamino, cyano($C_1$–$C_6$)alkylamino, aminocarbonyl($C_1$–$C_6$) alkylamino, acetylamino($C_1$–$C_6$)alkylamino, (acetyl) (($C_1$–$C_6$)alkyl)amino($C_1$–$C_6$)alkylamino, ($C_1$–$C_6$) alkoxycarbonylamino($C_1$–$C_6$)alkylamino, ($C_2$–$C_9$) heterocycloalkyloxycarbonylamino($C_1$–$C_6$)alkylamino, ($C_2$–$C_9$)heteroaryloxycarbonylamino($C_1$–$C_6$)alkylamino, cyanoguanidino($C_1$–$C_6$)alkylamino, ($C_1$–$C_6$) alkylcyanoguanidino($C_1$–$C_6$)alkylamino, (($C_1$–$C_6$)alkyl)$_2$ cyanoguanidino($C_1$–$C_6$)alkylamino, ($C_1$–$C_6$) alkylsulfonylamino($C_1$–$C_6$)alkylamino, ureido($C_1$–$C_6$) alkylamino, ($C_1$–$C_6$)alkylureido($C_1$–$C_6$)alkylamino, (($C_1$–$C_6$)alkyl)$_2$ureido($C_1$–$C_6$)alkylamino, aminocarbonyloxy($C_1$–$C_6$)alkylamino, acetylamino($C_1$–$C_6$) alkylcarbonylamino, (acetyl)(($C_1$–$C_6$)alkyl)amino($C_1$–$C_6$) alkylcarbonylamino, aminocarbonyl($C_1$–$C_6$) alkylcarbonylamino, ($C_1$–$C_6$)alkylaminocarbonyl($C_1$–$C_6$) alkylcarbonylamino, (($C_1$–$C_6$)alkyl)$_2$aminocarbonyl ($C_1$–$C_6$)alkylcarbonylamino, ureido($C_1$–$C_6$) alkylcarbonylamino, ($C_1$–$C_6$)alkylureido($C_1$–$C_6$) alkylcarbonylamino, (($C_1$–$C_6$)alkyl)$_2$ureido($C_1$–$C_6$) alkylcarbonylamino, ($C_1$–$C_6$)alkoxycarbonylamino($C_1$–$C_6$) alkylcarbonylamino, aminosulfonyl($C_1$–$C_6$) alkylcarbonylamino, hydroxy($C_1$–$C_6$)alkylamino($C_1$–$C_6$) alkylcarbonylamino, ($C_1$–$C_6$)alkoxy($C_1$–$C_6$)alkylamino ($C_1$–$C_6$)alkylcarbonylamino, ($C_2$–$C_9$) heterocycloalkyloxycarbonylamino, ($C_2$–$C_9$) heteroarylcarbonylamino($C_1$–$C_6$)alkylcarbonylamino, ($C_2$–$C_9$)heterocycloalkylcarbonylamino($C_1$–$C_6$) alkylcarbonylamino, cyanoguanidino($C_1$–$C_6$) alkylcarbonylamino, cyano($C_1$–$C_6$)alkylcarbonylamino, ($C_1$–$C_6$)alkylcarbonylamino($C_1$–$C_6$)alkylamino-carbonylamino, amino($C_1$–$C_6$)alkylaminocarbonylamino, ($C_1$–$C_6$)alkylamino($C_1$–$C_6$)alkylaminocarbonyl amino, (($C_1$–$C_6$)alkyl)$_2$amino($C_1$–$C_6$)alkylaminocarbonylamino, carboxy($C_1$–$C_6$)alkylaminocarbonyl amino, aminocarbonyl ($C_1$–$C_6$)alkylaminocarbonylamino, ($C_1$–$C_6$) alkylaminocarbonyl($C_1$–$C_6$)alkylaminocarbonylamino, ($C_1$–$C_6$)alkylsulfonylamino($C_1$–$C_6$) alkylaminocarbonylamino, ($C_1$–$C_6$)alkoxycarbonyl amino ($C_1$–$C_6$)alkylaminocarbonylamino, ($C_2$–$C_9$) heterocycloalkyloxycarbonyl amino($C_1$–$C_6$) alkylaminocarbonylamino, ($C_2$–$C_9$) heteroaryloxycarbonylamino($C_1$–$C_6$) alkylaminocarbonylamino, ($C_2$–$C_9$)heterocycloalkyl ($C_1$–$C_6$)alkylaminocarbonylamino, ($C_2$–$C_9$)heteroaryl ($C_1$–$C_6$)alkylaminocarbonylamino, ureido($C_1$–$C_6$) alkylureido, ($C_1$–$C_6$)alkylureido($C_1$–$C_6$)alkylureido, (($C_1$–$C_6$)alkyl)$_2$ureido($C_1$–$C_6$)alkylureido, cyanoguanidino ($C_1$–$C_6$)alkylureido, amino($C_1$–$C_6$)alkylsulfonylamino, ($C_1$–$C_6$)alkylamino($C_1$–$C_6$)alkylsulfonylamino, (($C_1$–$C_6$)

alkyl)$_2$amino(C$_1$–C$_6$)alkylsulfonylamino, acetylamino (C$_1$–C$_6$)alkylsulfonylamino, (acetyl)((C$_1$–C$_6$)alkyl)amino (C$_1$–C$_6$)alkylsulfonylamino, ureido(C$_1$–C$_6$) alkylsulfonylamino, (C$_1$–C$_6$)alkylureido(C$_1$–C$_6$) alkylsulfonylamino, ((C$_1$–C$_6$)alkyl)$_2$ureido(C$_1$–C$_6$) alkylsulfonylamino, (C$_1$–C$_6$)alkylsulfonylamino(C$_1$–C$_6$) alkylsulfonylamino, cyanoguanidino(C$_1$–C$_6$) alkylsulfonylamino, (C$_1$–C$_6$)alkyl(cyanoguanidino)(C$_1$–C$_6$) alkylsulfonylamino, ((C$_1$–C$_6$)alkyl)$_2$(cyanoguanidino) (C$_1$–C$_6$)alkylsulfonylamino, aminocarbonyl(C$_1$–C$_6$) alkylsulfonylamino, (C$_1$–C$_6$)alkoxycarbonylamino(C$_1$–C$_6$) alkylsulfonylamino, (C$_2$–C$_9$) heterocycloalkyloxycarbonylamino(C$_1$–C$_6$) alkylsulfonylamino, (C$_2$–C$_9$)heteroaryloxycarbonylamino (C$_1$–C$_6$)alkylsulfonylamino, aminosulfonylamino(C$_1$–C$_6$) alkyl, (C$_1$–C$_6$)alkylaminosulfonylamino, ((C$_1$–C$_6$)alkyl)$_2$ aminosulfonylamino(C$_1$–C$_6$)alkyl, cyanoguanidino, (C$_1$–C$_6$)alkyl(cyanoguanidino), ((C$_1$–C$_6$)alkyl)$_2$ (cyanoguanidino), (C$_2$–C$_9$)heterocycloalkyl (cyanoguanidino), (C$_2$–C$_9$)heterocycloalkyl (cyanoguanidino), (C$_2$–C$_9$)heteroaryl(cyanoguanidino), (C$_2$–C$_9$)heterocycloalkyl(C$_1$–C$_6$)alkyl(cyanoguanidino), (C$_2$–C$_9$)heteroaryl(C$_1$–C$_6$)alkyl(cyanoguanidino), amino (C$_1$–C$_6$)alkyl(cyanoguanidino), (C$_1$–C$_6$)alkylamino(C$_1$–C$_6$) alkyl(cyanoguanidino), ((C$_1$–C$_6$)alkyl)$_2$amino(C$_1$–C$_6$)alkyl (cyanoguanidino), aminocarbonyl(C$_1$–C$_6$)alkyl (cyanoguanidino), (C$_1$–C$_6$)alkylaminocarbonyl(C$_1$–C$_6$) alkyl(cyanoguanidino), ((C$_1$–C$_6$)alkyl)$_2$aminocarbonyl (C$_1$–C$_6$)alkyl(cyanoguanidino), (C$_2$–C$_9$)heterocycloalkyl, amino(C$_1$–C$_6$)alkylamino, (C$_1$–C$_6$)alkylamino(C$_1$–C$_6$) alkylamino, ((C$_1$–C$_6$)alkyl)$_2$amino(C$_1$–C$_6$)alkylamino, (C$_2$–C$_9$)heteroarylamino, ureido(C$_1$–C$_6$)alkylamino, (C$_1$–C$_6$)alkylureido(C$_1$–C$_6$)alkylamino, ((C$_1$–C$_6$)alkyl)$_2$ ureido(C$_1$–C$_6$)alkylamino, (C$_1$–C$_6$)alkylsulfonylamino (C$_1$–C$_6$)alkylamino, (C$_1$–C$_6$)alkoxycarbonylamino(C$_1$–C$_6$) alkylamino, (C$_2$–C$_9$)heterocycloalkyloxycarbonylamino (C$_1$–C$_6$)alkylamino, (C$_2$–C$_9$)heteroaryloxycarbonylamino (C$_1$–C$_6$)alkylamino, aminocarbonyl(C$_1$–C$_6$)alkylamino, cyanoguanidino(C$_1$–C$_6$)alkylamino, (C$_2$–C$_9$)heteroaryl (C$_1$–C$_6$)alkylamino, (C$_2$–C$_9$)heterocycloalkylamino, (C$_1$–C$_6$)alkylcarbonylamino, halo(C$_1$–C$_6$) alkylcarbonylamino, (C$_1$–C$_6$)alkoxycarbonylamino, ureido, (C$_1$–C$_6$)alkylureido, ((C$_1$–C$_6$)alkyl)$_2$ureido, amino, (C$_1$–C$_6$) alkylamino, (C$_3$–C$_{10}$)cycloalkylamino, ((C$_1$–C$_6$)alkyl)$_2$ amino, hydroxy(C$_1$–C$_6$)alkylamino, (C$_6$–C$_{10}$)arylamino, (C$_6$–C$_{10}$)aryl(C$_1$–C$_6$)alkylamino, (C$_1$–C$_6$) alkylcarbonylamino, (C$_6$–C$_{10}$)arylcarbonylamino, ((C$_1$–C$_6$) alkylcarbonyl)((C$_1$–C$_6$)alkyl)amino, (C$_3$–C$_{10}$)cycloalkyl (C$_1$–C$_6$)alkyl)amino, (C$_1$–C$_6$)alkoxycarbonylamino, (C$_1$–C$_6$)alkoxycarbonyl(C$_1$–C$_6$)alkylcarbonylamino, ((C$_1$–C$_6$)alkoxycarbonyl)((C$_1$–C$_6$)alkyl)amino, (C$_1$–C$_6$) alkylsulfonylamino, ((C$_1$–C$_6$)alkylsulfonyl)((C$_1$–C$_6$)alkyl) amino, (C$_6$–C$_{10}$)arylsulfonylamino, ((C$_6$–C$_{10}$)arylsulfonyl) ((C$_1$–C$_6$)alkyl)amino, (C$_2$–C$_9$)heterocycloalkylamino, (C$_2$–C$_9$)heteroarylamino, halo(C$_1$–C$_6$)alkylamino, (C$_6$–C$_{10}$) arylamino, (C$_6$–C$_{10}$)aryl(C$_1$–C$_6$)alkylamino, (aminocarbonyl(C$_1$–C$_6$)alkylamino, ((C$_1$–C$_6$) alkylaminocarbonyl(C$_1$–C$_6$)alkylamino, (carboxy(C$_1$–C$_6$) alkyl)amino, ((C$_1$–C$_6$)alkoxycarbonyl(C$_1$–C$_6$)alkylamino, (amino(C$_1$–C$_6$)alkyl)amino, (hydroxy(C$_1$–C$_6$)alkylamino, ureido, (C$_1$–C$_6$)alkylureido, ((C$_1$–C$_6$)alkyl)$_2$ureido, (C$_6$–C$_{10}$)arylureido, (C$_6$–C$_{10}$)aryl)$_2$ureido, (C$_6$–C$_{10}$)aryl (C$_1$–C$_6$)alkylureido, halo(C$_1$–C$_6$)alkylureido, (halo(C$_1$–C$_6$) alkyl)((C$_1$–C$_6$)alkyl)ureido, ((C$_1$–C$_6$)alkoxycarbonyl (C$_1$–C$_6$)alkyl)ureido, and glycinamido.

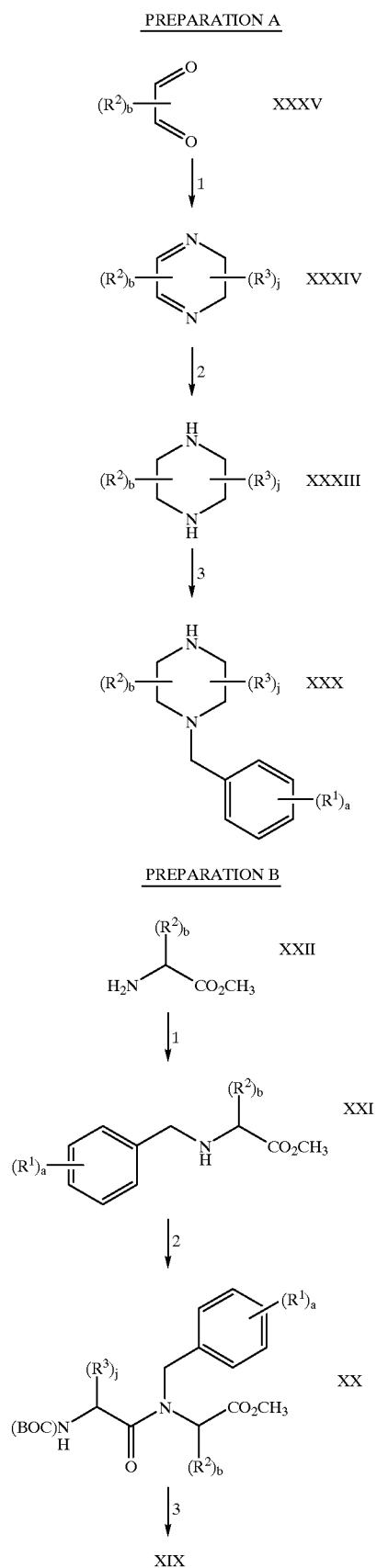

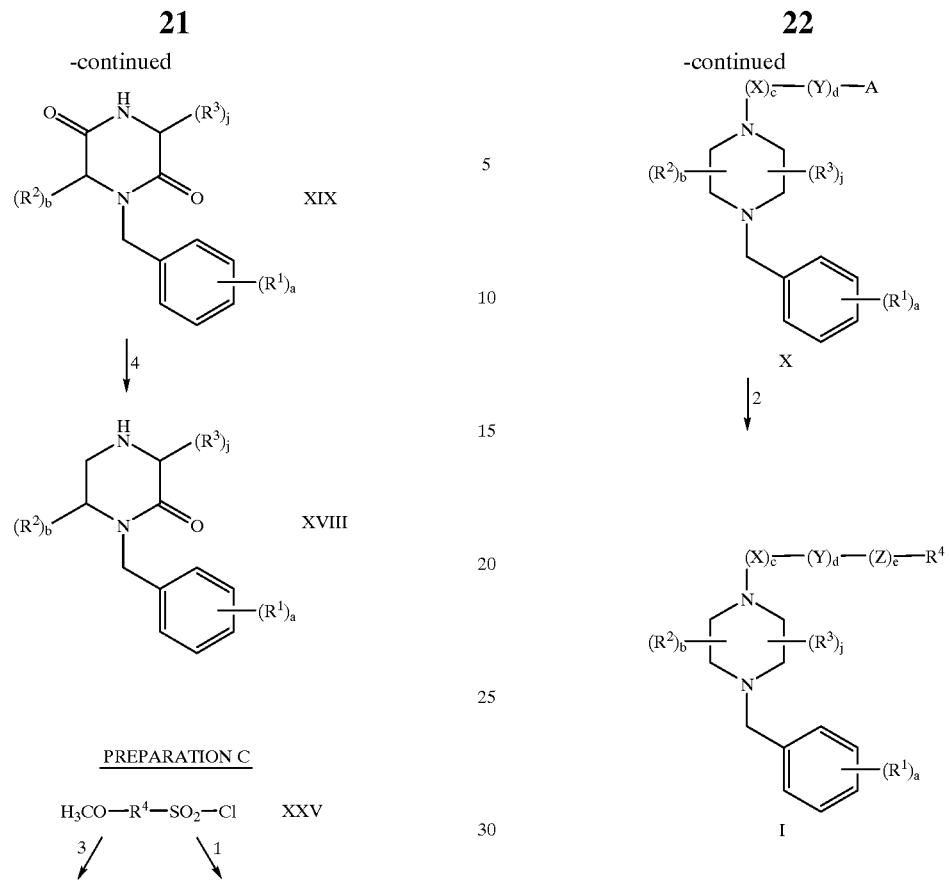
PREPARATION C
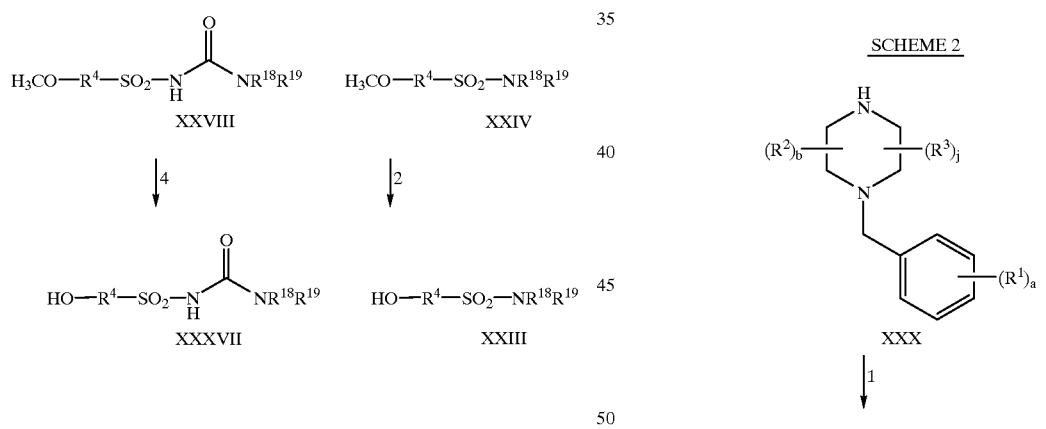
SCHEME 1
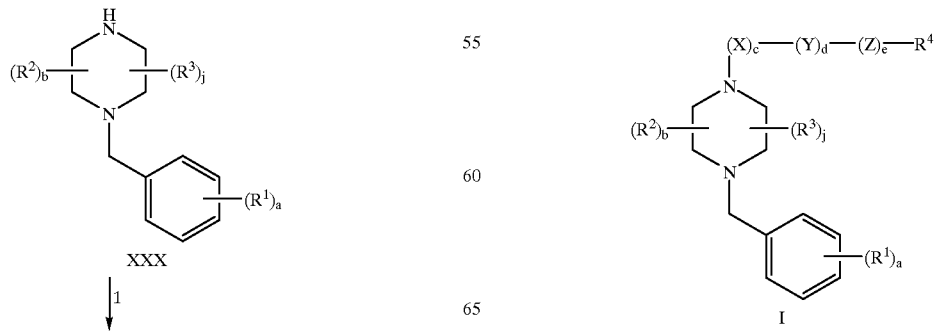

SCHEME 3
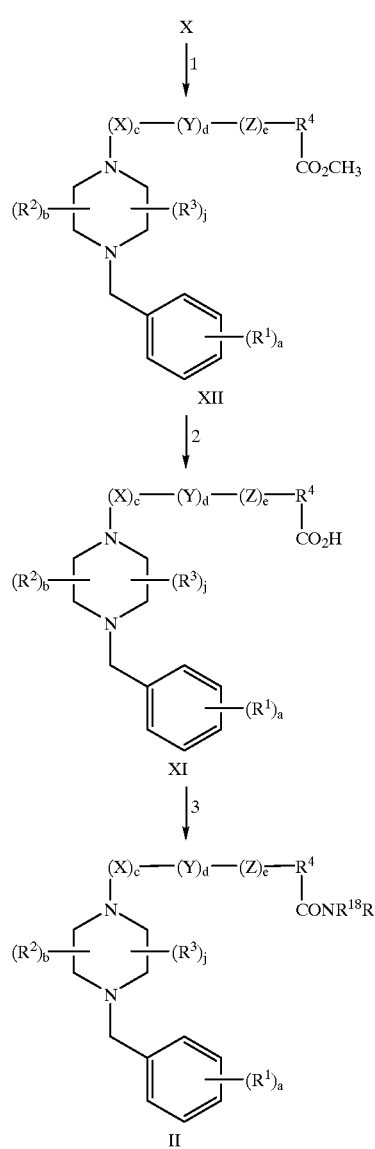
SCHEME 4
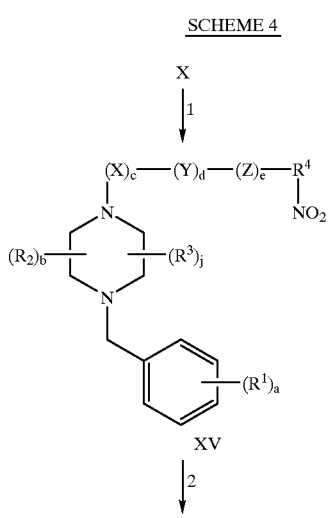
-continued
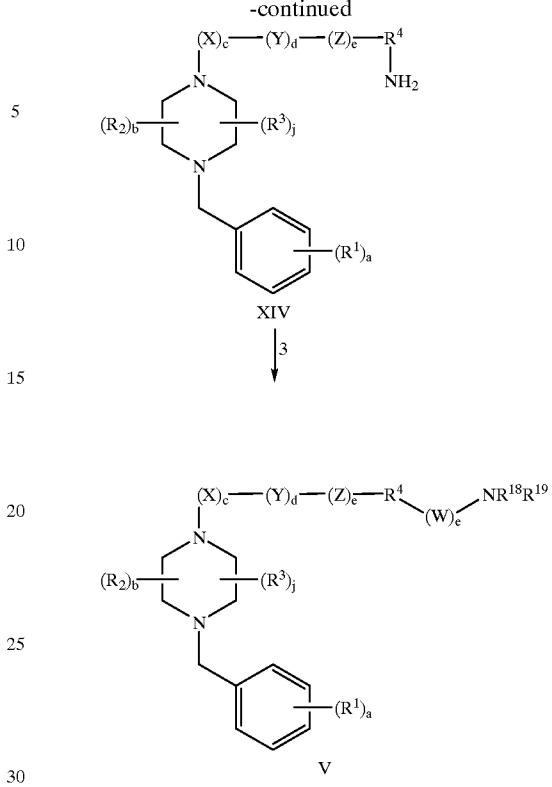
SCHEME 5
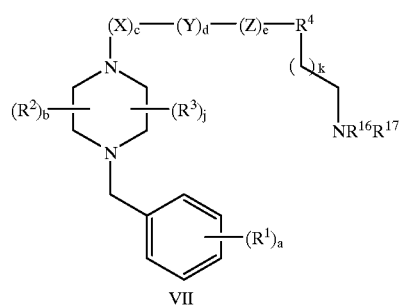

SCHEME 6

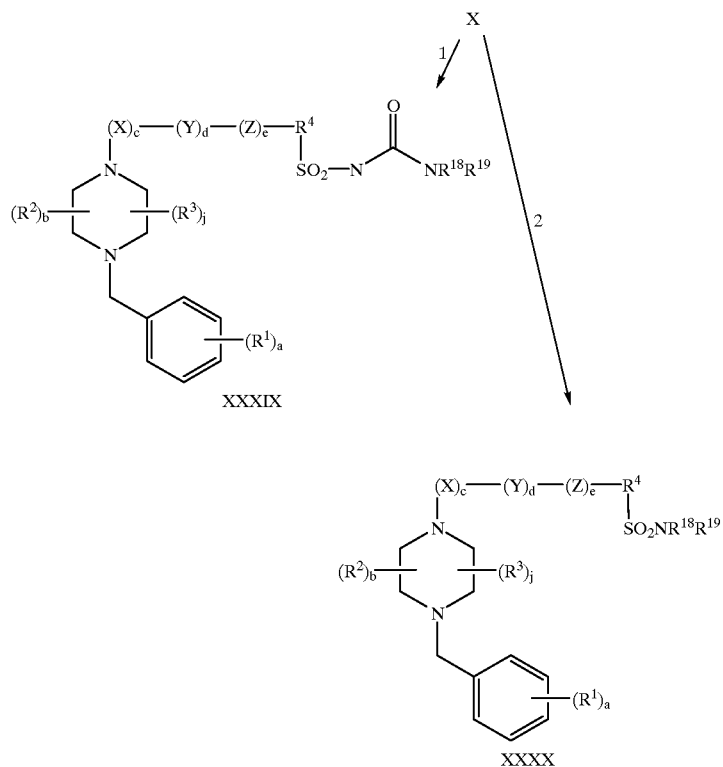

SCHEME 7

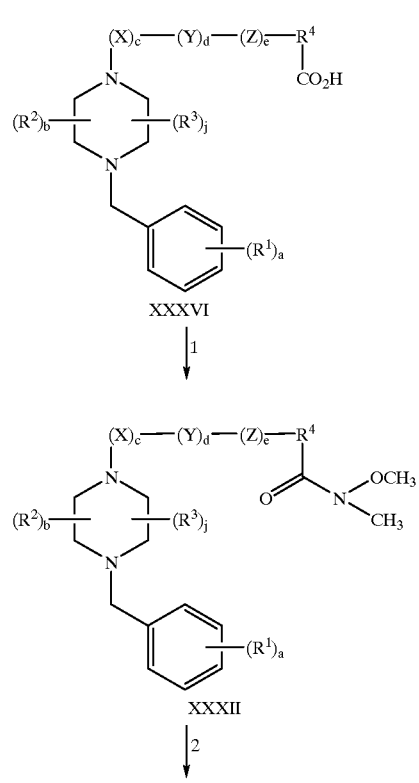

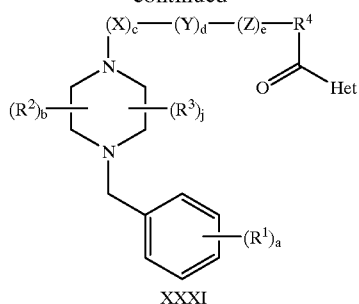

In reaction 1 of Preparation A, the compound of formula XXXV, wherein b is 0, 1 or 2, is converted to the corresponding compound of formula XXXIV by reacting XXXV with an ethyldiamine compound of the formula, $(R^3)_j$-ethyldiamine, in the presence of an aprotic solvent, such as diethylether. The reaction mixture is heated to reflux for a time period between about 1 hour to about 12 hours.

In reaction 2 of Preparation A, the compound of formula XXXIV is converted to the corresponding compound of formula XXXIII by reducing XXXIV with a reducing agent, such as sodium borohydride, in a refluxing protic solvent, such as ethanol.

In reaction 3 of Preparation A, the compound of formula XXXIII is converted to the corresponding compound of formula XXX by reacting XXXIII with a benzaldehyde compound of the formula

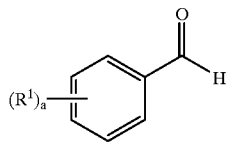

in the presence of a base, such as triethylamine, and a reducing agent, such as sodium triacetoxyborohydride, in an aprotic solvent, such as 1,2-dichloroethane. The reaction mixture is stirred at room temperature for a time period between about 1 hour to about 4 hours, preferably about 2 hours.

In reaction 1 of Preparation B, the compound of formula XXII, wherein b is 0, 1 or 2, is converted to the corresponding compound of formula XXI by reacting XXIII with a benzaldehyde compound of the formula

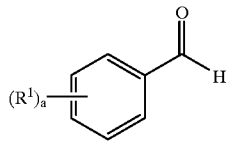

in the presence of a base, such as triethylamine, a reducing agent, such as sodium borohydride and an aprotic solvent, such as 1,2-dichloroethane. The reaction is stirred, at room temperature, for a time period between about 1 hour to about 4 hours, preferably about 2 hours.

In reaction 2 of Preparation B, the compound of formula XXI is converted to the corresponding compound of formula XX by first reacting a compound of the formula

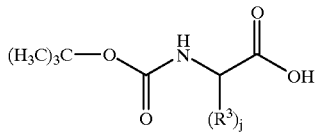

wherein j is 0, 1 or 2, with 4-methyl morpholine and isobutylchloroformate in the presence of a polar aprotic solvent, such as tetrahydrofuran, followed by reacting the intermediate so formed with the compound of formula XXI. The reaction mixture, so formed, is stirred overnight at room temperature.

In reaction 3 of Preparation B, the compound of formula XX is converted to the corresponding piperizine-2,5-dione compound of formula XIX by treating XX with trifluoroacetic acid in the presence of a polar aprotic solvent, such as methylene chloride. The reaction is stirred, at room temperature, for a time period between about 1 hour to about 4 hours, preferably about 2 hours.

In reaction 4 of Preparation B, the compound of formula XIX is converted to the corresponding compound of formula XVIII by reducing XIX with a reducing agent, such as lithium aluminum hydride. The reaction is conducted at a temperature between about −100° C. to about 10° C., preferably about 0° C., for a time period between about 10 minutes to about 90 minutes, preferably about 40 minutes.

In reaction 1 of the Preparation C, the compound of formula XXV is converted to the corresponding compound of formula XXIV by reacting XXV with an amine of the formula, $NHR^{18}R^{19}$, wherein $R^{18}$ and $R^{19}$ are each independently selected from hydrogen, a nitrogen containing $(C_2–C_9)$heterocycloalkyl or $(C_2–C_9)$heteroaryl group, or $(C_1–C_6)$alkyl optionally substituted by hydroxy, aminocarbonyl, $(C_1–C_6)$alkylaminocarbonyl, $((C_1–C_6)$alkyl$)_2$carbonyl, carboxy, $(C_1–C_6)$alkylsulfonylamino, $(C_1–C_6)$alkoxycarbonylamino, aminosulfonyl, $(C_1–C_6)$alkylaminosulfonyl, $((C_1–C_6)$alkyl$)_2$aminosulfonyl, $(C_6–C_{10})$alkoxy, $(C_2–C_9)$heteroaryl, $(C_2–C_9)$heterocycloalkyl, $(C_1–C_6)$alkylcarbonylamino, $((C_1–C_6)$alkylcarbonyl$)((C_1–C_6)$alkyl$)$amino, cyano, ureido, $(C_1–C_6)$alkylureido, $((C_1–C_6)$alkyl$)_2$ureido, cyanoguanidino, $(C_1–C_6)$alkylcyanoguanidino and $((C_1–C_6)$alkyl$)_2$cyanoguanidino, or $R^{18}$ and $R^{19}$ are taken together with the nitrogen to which they are attached to form a $(C_2–C_9)$heteroaryl or $(C_2–C_9)$heterocycloalkyl group, in the presence of a polar aprotic solvent, such as methylene chloride. The reaction mixture is stirred, at room temperature, for a time period between about 1 hour to about 24 hours, preferably about 12 hours.

In reaction 2 of Preparation C, the compound of formula XXIV is converted to the corresponding compound of formula XXIII by reacting XXIV with thiophenol in the presence of a base, such as sodium hydride, and a polar aprotic solvent, such as dimethylformamide. The reaction is heated to reflux for a time period between about 1 hour to about 10 hours, preferably about 4 hours.

In reaction 3 of Preparation C, the compound of formula XXV is converted to the corresponding compound of formula XXXVIII by reacting XXV with sodium cyanate in the presence of pyridine and a polar aprotic solvent, such as acetonitrile. The reaction is stirred, at room temperature, for a time period between about 2 hours to about 18 hours, preferably about 10 hours. An amine of the formula, $H_2N—C(O)—NR^{18}R^{19}$, is then added and the reaction mixture so formed is stirred, at room temperature, for a time period between about 2 hours to about 24 hours, preferably about 8 hours In reaction 4 of Preparation C, the compound of formula XXXVIII is converted to the corresponding compound of formula XXXVII according to the procedure described above in reaction 2 of Preparation C.

In reaction 1 of Scheme 1, the compound of formula XXX is converted to the corresponding compound of formula X by reacting XXX with a compound of the formula, $A-(X)_c-(Y)_d-A$, wherein A is chloro or bromo, in the presence of a base, such as triethylamine, and a polar aprotic solvent, such as methylene chloride. The reaction is stirred at a temperature between about −10° C. to about 10° C., for a time period between about 15 minutes to about 90 minutes, preferably about 30 minutes.

In reaction 2 of Scheme 1, the compound of formula X is converted to the corresponding compound of formula I by reacting X with a compound of the formula, $H-(Z)_e-R^4$ wherein e is 1 and Z is oxygen, in the presence of potassium carbonate, potassium iodide and an aprotic solvent, such as butanone. The reaction is heated to reflux for a time period between about 4 hours to about 8 hours, preferably about 6 hours.

In reaction 1 of Scheme 2, the compound of formula XXX is converted to the corresponding compound of formula I by reacting XXX with a compound of the formula, $A-(X)_c-(Y)_d-(Z)_e-R^4$, wherein A is chloro or bromo, in the presence of a base, such as triethylamine, and a polar aprotic solvent, such as methylene chloride. The reaction is stirred at a temperature between about −10° C. to about 10° C., for a time period between about 15 minutes to about 90 minutes, preferably about 30 minutes.

In reaction 1 of Scheme 3, the compound of formula X is converted to the corresponding compound of formula XII according to the procedure described above in reaction 2 of Scheme 1.

In reaction 2 of Scheme 3, the compound of formula XII is converted to the corresponding compound of formula XI by reacting XII with lithium hydroxide monohydrate in the presence of methanol, tetrahydrofuran and water. The reaction mixture is stirred overnight at room temperature.

In reaction 3 of Scheme 3, the compound of formula XI is converted to the corresponding compound of formula II, by reacting XI with an amine, in the presence of 4-dimethylaminopyridine, 1-(3-dimethylaminopropyl)-3-ethylcarbodiimine and a polar aprotic solvent, such as methylene chloride. The resulting reaction mixture is stirred overnight at room temperature.

In reaction 1 of Scheme 4, the compound of formula X is converted to the corresponding compound of formula XV according to the procedure described above in reaction 2 of Scheme 1.

In reaction 2 of Scheme 4, the compound of formula XV is converted to the corresponding compound of formula XIV by hydrogenating XV in the presence of a catalyst, such as platinum on carbon, and a polar protic solvent, such as ethanol. The reaction is carried out under a pressure between about 30 psi to about 40 psi, preferably about 35 psi, for a time period between about 15 minutes to about 1 hour, preferably 30 minutes.

In reaction 3 of Scheme 4, for urea formation, the compound of formula XIV is converted to the corresponding compound of formula V by first reacting XIV with 4-nitrophenyl chloroformate in the presence of a base, such as pyridine, and a polar aprotic solvent, such as methlyene chloride, followed by reacting the intermediate so formed with an amine. The reaction mixture, so formed, is allowed to stir overnight at room temperature. For sulfonamide formation, the compound of formula XIV is reacted with a sulfonyl chloride compound of the formula, $R^{16}$—Cl, in the presence of a base, such as triethylamine, and a polar aprotic solvent, such as methylene chloride. The reaction is stirred overnight at ambient temperature. For cyanoguanidine formation, the compound of formula XIV is first treated with sodium hydride in an aprotic solvent, such as tetrahydrofuran, followed by reacting, the intermediate so formed with dimethyl-N-cyanodithio iminocarbonate. The reaction mixture so formed is heated to reflux overnight. The N-cyano-S-methyl-isothiourea intermediate is then reacted with an amine in the presence of a polar protic solvent, such as methanol. For amide formation, the compound of formula XIV is reacted with an acid, such as 3-tert-butoxycarbonylaminopropionic acid in the presence of N-methylmorpholine, O-benzotriazole-1-yl-N,N,N,'N'-tetramethyluronium hexafluorophosphate and a polar aprotic solvent, such as methylene chloride.

In reaction 1 of Scheme 5, the compound of formula X is converted to the corresponding compound of formula XVI, wherein k is 0, 1, 2, 3 or 4, according to the procedure described above in reaction 2 of Scheme 1.

In reaction 2 of Scheme 5, the compound of formula XVI is converted to the corresponding compound of formula VII by reacting XVI with an amine of the formula, $R^{16} R^{17}N$, wherein $R^{16}$ and $R^{17}$ are each independently hydrogen, a nitrogen containing $(C_2-C_9)$heterocycloalkyl or $(C_2-C_9)$ heteroaryl group, or $(C_1-C_6)$alkyl optionally substituted by hydroxy, aminocarbonyl, $(C_1-C_6)$alkylaminocarbonyl, $((C_1-C_6)alkyl)_2$carbonyl, carboxy, $(C_1-C_6)$alkylsulfonylamino, $(C_1-C_6)$alkoxycarbonylamino, aminosulfonyl, $(C_1-C_6)$alkylaminosulfonyl, $((C_1-C_6)alkyl)_2$aminosulfonyl, $(C_6-C_{10})$alkoxy, $(C_2-C_9)$ heteroaryl, $(C_2-C_9)$heterocycloalkyl, $(C_1-C_6)$ alkylcarbonylamino, $((C_1-C_6)alkylcarbonyl)((C_1-C_6)alkyl)$ amino, cyano, ureido, $(C_1-C_6)$alkylureido, $((C_1-C_6)alkyl)_2$ ureido, cyanoguanidino, $(C_1-C_6)$alkylcyanoguanidino and $((C_1-C_6)alkyl)_2$cyanoguanidino, in the presence of a 10:1 ratio solution of dichloroethane/acetic acid. The reaction mixture is stirred, at room temperature, for a time period between about 30 minutes to about 2 hours, preferably about 1 hour. A reducing agent, such as sodium cyanoborohydride is than added to the mixture and the reaction is allowed to stir overnight at room temperature. When $R^{16}$ and/or $R^{17}$ is/are hydrogen, the compound of formula VII may further be reacted according to the procedure described above in reaction 3 of Scheme 4, to provide ureas, sulfonamides, cyanoguanidinos, or amides.

In reaction 1 of Scheme 6, the compound of formula X is converted to the corresponding compound of formula XXXIX according to the procedure described above in reaction 2 of Scheme 1.

In reaction 2 of Scheme 6, the compound of formula X is converted to the corresponding compound of formula XXXX according to the procedure described above in reaction 2 of Scheme 1.

In reaction 1 of Scheme 7, the acid compound of formula XXXVI is converted to the corresponding compound of formula XXXII by treating XXXVI with thionyl chloride neat or in an aprotic solvent, at room temperature, for a time period between about 1 hour to about 24 hours, preferably 1 hour. The acid chloride so formed is dissolved in a polar aprotic solvent with a compound of the formula, $(H_3CO)(H_3C)NH.HCl$, in the presence of an amine base, such as triethylamine. The reaction mixture is stirred, at room temperature, for a time period between about 1 hour to about 48 hours, preferably about 12 hours.

In reaction 2 of Scheme 7, the amide compound of formula XXXII is converted to the corresponding compound of formula XXXI by reacting XXXII with a $(C_2-C_9)$ heteroaryl lithium reagent in the presence of a polar aprotic solvent at a temperature between about $-100°$ C. to room temperature, preferably about $-78°$ C. The resulting reaction mixture is stirred for a time period between about 1 hour to about 24 hours, preferably about 12 hours, at a temperature between about $-78°$ C. to about $50°$ C., preferably about $20°$ C.

Unless indicated otherwise, the pressure of each of the above reactions is not critical. Generally, the reactions will be conducted at a pressure of about one to about three atmospheres, preferably at ambient pressure (about one atmosphere).

The compounds of the formula I which are basic in nature are capable of forming a wide variety of different salts with various inorganic and organic acids. Although such salts must be pharmaceutically acceptable for administration to animals, it is often desirable in practice to initially isolate a compound of the formula I from the reaction mixture as a pharmaceutically unacceptable salt and then simply convert the latter back to the free base compound by treatment with an alkaline reagent, and subsequently convert the free base to a pharmaceutically acceptable acid addition salt. The acid addition salts of the base compounds of this invention are readily prepared by treating the base compound with a substantially equivalent amount of the chosen mineral or organic acid in an aqueous solvent medium or in a suitable organic solvent such as methanol or ethanol. Upon careful evaporation of the solvent, the desired solid salt is obtained.

The acids which are used to prepare the pharmaceutically acceptable acid addition salts of the base compounds of this invention are those which form non-toxic acid addition salts, i.e., salts containing pharmacologically acceptable anions, such as hydrochloride, hydrobromide, hydroiodide, nitrate, sulfate or bisulfate, phosphate or acid phosphate, acetate, lactate, citrate or acid citrate, tartrate or bitartrate, succinate, maleate, fumarate, gluconate, saccharate, benzoate, methanesulfonate and pamoate [i.e., 1,1'-methylene-bis-(2-hydroxy-3-naphthoate)] salts.

Those compounds of the formula I which are also acidic in nature, are capable of forming base salts with various pharmacologically acceptable cations. Examples of such salts include the alkali metal or alkaline-earth metal salts and particularly, the sodium and potassium salts. These salts are all prepared by conventional techniques. The chemical bases which are used as reagents to prepare the pharmaceutically acceptable base salts of this invention are those which form non-toxic base salts with the herein described acidic compounds of formula I. These non-toxic base salts include those derived from such pharmacologically acceptable cations as sodium, potassium, calcium and magnesium, etc. These salts can easily be prepared by treating the corresponding acidic compounds with an aqueous solution containing the desired pharmacologically acceptable cations, and then evaporating the resulting solution to dryness, preferably under reduced pressure. Alternatively, they may also be prepared by mixing lower alkanolic solutions of the acidic compounds and the desired alkali metal alkoxide together, and then evaporating the resulting solution to dryness in the same manner as before. In either case, stoichiometric quantities of reagents are preferably employed in order to ensure completeness of reaction and maximum product yields.

Compounds of the formula I and their pharmaceutically acceptable salts (hereinafter also referred to, collectively, as "the active compounds") are potent antagonists of the CCR1 receptors. The active compounds are useful in the treatment or prevention of autoimmune diseases (such as rheumatoid arthritis, type I diabetes (recent onset), inflammatory bowel disease, optic neuritis, psoriasis, multiple sclerosis, polymyalgia rheumatica, uveitis, and vasculitis), acute and chronic inflammatory conditions (such as osteoarthritis, adult respiratory distress syndrome, Respiratory Distress Syndrome of infancy, ischemia reperfusion injury, and glomerulonephritis), allergic conditions (such as asthma and atopic dermatitis), infection associated with inflammation (such as viral inflammation (including influenza and hepatitis) and Guillian-Barre), chronic bronchitis, xenotransplantation, transplantation tissue rejection, atherosclerosis, restenosis, HIV infectivity (co-receptor usage), and granulomatous diseases (including sarcoidosis, leprosy and tuberculosis).

The activity of the compounds of the invention can be assessed according to procedures know to those of ordinary skill in the art. Examples of recognized methods for determining CCR1 induced migration can be found in Coligan, J. E., Kruisbeek, A. M., Margulies, D. H., Shevach, E. M., Strober, W. editors: *Current Protocols In Immunology,* 6.12.1–6.12.3. (John Wiley and Sons, NY, 1991). One specific example of how to determine the activity of a compound for inhibiting migration is described in detail below.

Chemotaxis Assay

The ability of compounds to inhibit the chemotaxis to various chemokines can be evaluated using standard 48 or 96 well Boyden Chambers with a 5 micron polycarbonate filter. All reagents and cells can be prepared in standard RPMI (BioWhitikker Inc.) tissue culture medium supplemented with 1 mg/ml of bovine serum albumin. Briefly, MIP-1α (Peprotech, Inc., P.O. Box 275, Rocky Hill N.J.) or other test agonists, were placed into the lower chambers of the Boyden chamber. A polycarbonate filter was then applied and the upper chamber fastened. The amount of agonist chosen is that determined to give the maximal amount of chemotaxis in this system (e.g., 1 nM for MIP-1α should be adequate).

THP-1 cells (ATCC TIB-202), primary human monocytes, or primary lymphocytes, isolated by standard techniques can then be added to the upper chambers in triplicate together with various concentrations of the test compound. Compound dilutions can be prepared using standard serological techniques and are mixed with cells prior to adding to the chamber.

After a suitable incubation period at 37 degrees centigrade (e.g. 3.5 hours for THP-1 cells, 90 minutes for primary monocytes), the chamber is removed, the cells in the upper chamber aspirated, the upper part of the filter wiped and the number of cells migrating can be determined according to the following method.

For THP-1 cells, the chamber (a 96 well variety manufactured by Neuroprobe) can be centrifuged to push cells off the lower chamber and the number of cells can be quantitated against a standard curve by a color change of the dye fluorocein diacetate.

For primary human monocytes, or lymphocytes, the filter can be stained with Dif Quik® dye (American Scientific Products) and the number of cells migrating can be determined microscopically.

The number of cells migrating in the presence of the compound are divided by the number of cells migrating in control wells (without the compound). The quotant is the % inhibition for the compound which can then be plotted using standard graphics techniques against the concentration of compound used. The 50% inhibition point is then determined using a line fit analysis for all concentrations tested. The line fit for all data points must have an coefficient of correlation (R squared) of >90% to be considered a valid assay.

All of the compounds of the invention that were tested had $IC_{50}$ of less than 25 $\mu$M, in the Chemotaxis assay.

The compositions of the present invention may be formulated in a conventional manner using one or more pharmaceutically acceptable carriers. Thus, the active compounds of the invention may be formulated for oral, buccal, intranasal, parenteral (e.g., intravenous, intramuscular or subcutaneous) or rectal administration or in a form suitable for administration by inhalation or insufflation. The active compounds of the invention may also be formulated for sustained delivery.

For oral administration, the pharmaceutical compositions may take the form of, for example, tablets or capsules prepared by conventional means with pharmaceutically acceptable excipients such as binding agents (e.g., pregelatinized maize starch, polyvinylpyrrolidone or hydroxypropyl methylcellulose); fillers (e.g., lactose, microcrystalline cellulose or calcium phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, methyl cellulose or hydrogenated edible fats); emulsifying agents (e.g., lecithin or acacia); non-aqueous vehicles (e.g., almond oil, oily esters or ethyl alcohol); and preservatives (e.g., methyl or propyl p-hydroxybenzoates or sorbic acid).

For buccal administration, the composition may take the form of tablets or lozenges formulated in conventional manner.

The active compounds of the invention may be formulated for parenteral administration by injection, including using conventional catheterization techniques or infusion. Formulations for injection may be presented in unit dosage form, e.g., in ampules or in multi-dose containers, with an added preservative. The compositions may take such forms as suspensions, solutions or emulsions in oily or aqueous vehicles, and may contain formulating agents such as suspending, stabilizing and/or dispersing agents. Alternatively, the active ingredient may be in powder form for reconstitution with a suitable vehicle, e.g., sterile pyrogen-free water, before use.

The active compounds of the invention may also be formulated in rectal compositions such as suppositories or retention enemas, e.g., containing conventional suppository bases such as cocoa butter or other glycerides.

For intranasal administration or administration by inhalation, the active compounds of the invention are conveniently delivered in the form of a solution or suspension from a pump spray container that is squeezed or pumped by the patient or as an aerosol spray presentation from a pressurized container or a nebulizer, with the use of a suitable propellant, e.g., dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. The pressurized container or nebulizer may contain a solution or suspension of the active compound. Capsules and cartridges (made, for example, from gelatin) for use in an inhaler or insufflator may be formulated containing a powder mix of a compound of the invention and a suitable powder base such as lactose or starch.

A proposed dose of the active compounds of the invention for oral, parenteral or buccal administration to the average adult human for the treatment of the conditions referred to above (e.g., rheumatoid arthritis) is 0.1 to 1000 mg of the active ingredient per unit dose which could be administered, for example, 1 to 4 times per day.

Aerosol formulations for treatment of the conditions referred to above (e.g., rheumatoid arthritis) in the average adult human are preferably arranged so that each metered dose or "puff" of aerosol contains 20 μg to 1000 μg of the compound of the invention. The overall daily dose with an aerosol will be within the range 0.1 mg to 1000 mg. Administration may be several times daily, for example 2, 3, 4 or 8 times, giving for example, 1, 2 or 3 doses each time.

The active agents can be formulated for sustained delivery according to methods well known to those of ordinary skill in the art. Examples of such formulations can be found in U.S. Pat. Nos. 3,538,214, 4,060,598, 4,173,626, 3,119,742, and 3,492,397.

The compounds of the invention can also be utilized in combination therapy with, but not limited to, other therapeutic agents such as with T-cell immunosuppressant agents such as rapamycin cyclosporin A and FK-506, with steroid sparing agents such as Cellcept®, or with classical anti-inflammatory agents (e.g. cyclooxygenase/lipoxygenase inhibitors) such as tenidap, aspirin, acetaminophen, naproxen and piroxicam.

The following Examples illustrate the preparation of the compounds of the present invention. NMR data are reported in parts per million (δ) and are referenced to the deuterium lock signal from the sample solvent (deuteriochloroform unless otherwise specified). Commercial reagents were utilized without further purification. THF refers to tetrahydrofuran. DMF refers to N,N-dimethylformamide. Chromatography refers to column chromatography performed using 32–63 mm silica gel and executed under nitrogen pressure (flash chromatography) conditions. Low Resolution Mass Spectra (LRMS) were recorded on either a Hewlett Packard 5989®, utilizing chemical ionization (ammonium), or a Fisons (or Micro Mass) Atmospheric Pressure Chemical Ionization (APCI) platform which uses a 50/50 mixture of acetonitrile/water with 0.1% formic acid as the ionizing agent. Room or ambient temperature refers to 20–25° C. All non-aqueous reactions were run under a nitrogen atmosphere for convenience and to maximize yields. The names for the compounds of the invention were created by the Autonom 2.0 PC-batch version from Beilstein Informationssysteme GmbH (ISBN 3-89536-976-4).

EXAMPLE 1

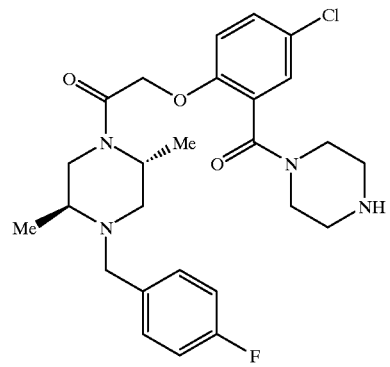

(2R,5S)-2-[4-Chloro-2-(piperazine-1-carbonyl)-phenoxy]-1-[4-(4-fluoro-benzyl)-2,5-dimethyl-piperazin-1-yl]-ethanone (R)-2-(4-Fluoro-benzylamino)-propionic acid methyl ester To a solution of (R)-2-amino-propionic acid methyl ester hydrochloride (25 g, 179 mmol) and 4-fluorobenzaldehyde (23 ml, 215 mmol) in 1,2-dichloroethane (200 ml) was added triethylamine (25 ml, 179 mmol). The resulting mixture was stirred for two hours at ambient temperature followed by addition of sodium acetoxyborohydride (57 g, 268 mmol) in four portions. The resulting mixture was stirred overnight at ambient temperature. The reaction was neutralized with dilute aqueous sodium hydroxide solution and extracted with dichloromethane (2×). The organic layers were combined, dried over magnesium sulfate, filtered and concentrated in vacuo. Chromatography on silica gel gave the title compound (34.4 g, 91% yield).

(2R,5S)-2-[(2-tert-Butoxycarbonylamino-propionyl)-(4-fluoro-benzyl)-amino]-propionic acid methyl ester To a solution of (R)-2-tert-butoxycarbonylamino-propionic acid (37 g, 195 mmol) in dry tetrahydrofuran (250 ml) at 0° C. was added 4-methyl morpholine (21.5 ml, 195 mmol) followed by isobutylchloroformate (25.3 ml, 195 mmol). The reaction was allowed to warm to ambient temperature and stirred for two hours. This was followed by the addition of (S)-2-(4-fluoro-benzylamino)-propionic acid methyl ester (34.4 g, 162 mmol). The resulting mixture was stirred overnight at ambient temperature. The reaction mixture was filtered through a pad of celite and the filter cake was washed with ethyl acetate. The filtrate was concentrated in vacuo, diluted with ethyl acetate and washed with water and brine. The organics were dried over magnesium sulfate, filtered and concentrated in vacuo. Chromatography on silica gel gave the title compound (43.2 g, 70% yield).

(2R,5S)-1-(4-Fluoro-benzyl)-3,6-dimethyl-piperazine-2,5-dione

To a solution of (2R,5S)-2-[(2-tert-butoxycarbonylamino-propionyl)-(4-fluoro-benzyl)-amino]-propionic acid methyl ester (43 g, 382 mmol) in dichloromethane (120 ml) at 0° C. was added trifluoroacetic acid (60 ml). The reaction was allowed to warm to ambient temperature and stirred for 2 hours. The reaction was cooled to 0° C. and slowly quenched by addition of 3N aqueous sodium hydroxide until basic. The resulting mixture was extracted with dichloromethane (2×). The combined organics were dried over magnesium sulfate, filtered and concentrated in vacuo to give the title compound (22 g, 78% yield).

(2R, 5S)-1-(4-Fluoro-benzyl)-2,5-dimethyl-piperazine

To a solution of (2R, 5S)-1-(4-fluoro-benzyl)-3,6-dimethyl-piperazine-2,5-dione (22 g, 87.9 mmol) in dry tetrahydrofuran (160 ml) at 0° C. was added a solution of lithium aluminum hydride (1M in tetrahydrofuran, 373 ml, 373 mmol) dropwise over 40 minutes. The reaction mixture was then refluxed for 4 hours, cooled to ambient temperature and slowly quenched with water. The resulting mixture was filtered through a pad of celite and the filter cake was washed with ethyl acetate. The filtrate was then concentrated, diluted with ethyl acetate and washed with saturated aqueous sodium hydrogen carbonate. The organic layer was separated, dried over magnesium sulfate, filtered and concentrated in vacuo to give the title compound (17.7 g, 91% yield).

(2R, 5S)-2-Chloro-1-[4-(4-fluoro-benzyl)-2,5-dimethyl-piperazin-1-yl]-ethanone

To a solution of (2R, 5S)-1-(4-fluoro-benzyl)-2,5-dimethyl-piperazine (2.5 g, 11.25 mmol) in dry dichloromethane (11 ml) at 0° C. was added triethylamine (1.57 ml, 11.2 mmol) followed by chloroacetyl chloride (0.858 ml, 11.2 mmol). The resulting reaction mixture was stirred for 30 minutes. The reaction was then filtered through a pad of celite, washed with dichloromethane and the resulting filtrate was concentrated to give a yellow oil Chromatography on silica get gave the title compound (2.84 g, 86% yield).

(2R, 5S)-5-Chloro-2-{2-[4-(4-fluoro-benzyl)-2,5-dimethyl-piperazin-1-yl]-2-oxo-ethoxy}-benzoic acid methyl ester To a solution of (2R, 5S)-2-chloro-1-[4-(4-fluoro-benzyl)-2,5-dimethyl-piperazin-1-yl]-ethanone (2.75 g, 9.2 mmol) in butanone (50 ml) was added methyl 5-chloro-2-hydroxybenzoate (1.55 g, 9.2 mmol), potassium carbonate (2.54 g, 18.4 mmol) and potassium iodide (1.52 g, 9.2 mmol). The resulting mixture was stirred at reflux for 6 hours. The reaction was then cooled, diluted with ethyl acetate, and washed with brine. The organics were dried over magnesium sulfate, filtered and concentrated in vacuo to give an orange oil. Chromatography on silica gel gave the title compound (4.1 g, 100% yield).

(2R, 5S)-5-Chloro-2-{2-[4-(4-fluoro-benzyl)-2,5-dimethyl-piperazin-1-yl]-2-oxo-ethoxy}-benzoic acid To a solution of (2R, 5S)-5-chloro-2-{2-[4-(4-fluoro-benzyl)-2,5-dimethyl-piperazin-1-yl]-2-oxo-ethoxy}-benzoic acid methyl ester (4.12 g, 9.18 mmol) in tetrahydrofuran (10 ml), methanol (10 ml) and water (4 ml) was added lithium hydroxide monohydrate (1.93 g, 45.9 mmol). The resulting mixture was stirred overnight at ambient temperature. The reaction was then concentrated, diluted with 1N hydrochloric acid and extracted with dichloromethane (2×). The organic layers were combined, dried over magnesium sulfate, filtered and concentrated to give a white foam. Triteration in dichloromethane and diethyl ether gave the title compound (1.38 g, 35% yield).

(2R, 5S)-4-(5-Chloro-2-{2-[4-(4-fluoro-benzyl)-2,5-dimethyl-piperazin-1-yl]-2-oxo-ethoxy}-benzoyl)-piperazine-1-carboxylic acid tert-butyl ester To a solution of (2R, 5S)-5-chloro-2-{2-[4-(4-fluoro-benzyl)-2,5-dimethyl-piperazin-1-yl]-2-oxo-ethoxy}-benzoic acid (0.10 g, 0.212 mmol) in dichloromethane (4 ml) was added 4-dimethylaminopyridine (0.039 g, 0.318 mmol), 1-(3-dimethylaminopropyl)-3-ethylcarbodiimide hydrochloride (0.061 g, 0.318 mmol) and tert-butyl 1-piperazinecarboxylate (0.041 g 0.222 mmol). The resulting mixture was stirred overnight at ambient temperature. It was then diluted with dichloromethane and washed with brine. The organics were dried over magnesium sulfate, filtered and concentrated to give a clear oil. Chromatography on silica gel gave the title compound (0.110 g, 85% yield).

(2R, 5S)-2-[4-Chloro-2-(piperazine-1-carbonyl)-phenoxy]-1-[4-(4-fluoro-benzyl)-2,5-dimethyl-piperazin-1-yl]-ethanone To a solution of (2R, 5S)-4-(5-chloro-2-{2-[4-(4-fluoro-benzyl)-2,5-dimethyl-piperazin-1-yl]-2-oxo-ethoxy}-benzoyl)-piperazine-1-carboxylic acid tert-butyl ester (0.110 g, 0.182 mmol) in dichloroethane (10 ml) was added trifluoroacetic acid (5 ml). The reaction was stirred for two hours at ambient temperature. The reaction was then diluted with dichloromethane and washed with 1N aqueous sodium hydroxide. The organics were dried over magnesium sulfate, filtered and concentrated to give the title compound (0.080 g, 87% yield).

The title compounds for Examples 2–12 were prepared by a method analogous to that described in Example 1.

| Example | R²⁰ | R² |
|---|---|---|
| 2 | ⸹—N\_\_/N—Me | Me |
| 3 | ⸹—N\_\_/O | Me |

-continued

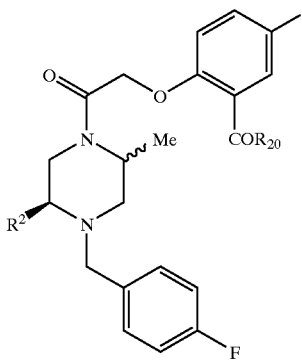

| Example | R²⁰ | R² |
|---|---|---|
| 4 |  —HN—CH₂CH₂—F | H |
| 5 |  —HN—CH₂—CF₃ | H |
| 6 |  pyridin-2-ylmethyl-NH— | H |
| 7 |  (S)-tetrahydrofuran-2-ylmethyl-NH— | H |
| 8 |  (R)-tetrahydrofuran-2-ylmethyl-NH— | H |
| 9 |  tetrahydrofuran-3-ylmethyl-NH— | H |
| 10 | —NHSO₂Me | Me |
| 11 | —NH—(CH₂)₂—NHSO₂CH₃ | CH₃ |
| 12 | —NH—(CH₂)₂—NHC(O)NH₂ | CH₃ |

EXAMPLE 13

(2R)-3-Amino-N-(5-chloro-2-{2-[4-(4-fluoro-benzyl)-2-methyl-piperazin-1-yl]2-oxo-ethoxy}-phenyl)-propionamide

[2-(5-Chloro-2-{2-[4-(4-fluoro-benzyl)-2-methyl-piperazin-1-yl]-2-oxo-ethoxy}-phenylcarbamoyl)-ethyl]-carbamic acid tert-butyl ester To a solution of 2-(2-amino-4-chloro-phenoxy)-1-[4-(4-fluoro-benzyl)-2-methyl-piperazin-1-yl]-ethanone (0.066 g, 0.17 mmol) in methylene chloride (2 mL) at ambient temperature was added N-methylmorpholine (0.025 mL, 0.23 mmol), 3-tert-butoxycarbonylamino-propionic acid (0.044 g, 0.23 mmol) and O-benzotriazole-1-yl-N,N,N', N'-tetramethyluronium hexafluorophosphate (0.076 g, 0.20 mmol). The resulting solution was stirred at ambient temperature for 60 hours, then concentrated. Radial chromatography (2 mm plate) gave the title compound (0.114 g)

(2R)-3-Amino-N-(5-chloro-2-{2-[4-(4-fluoro-benzyl)-2-methyl-piperazin-1-yl]-2-oxo-ethoxy}-phenyl)-propionamide To a solution of [2-(5-chloro-2-{2-[4-(4-fluoro-benzyl)-2-methyl-piperazin-1-yl]-2-oxo-ethoxy}-phenylcarbamoyl)-ethyl]-carbamic acid tert-butyl ester (0.110 g, 0.2 mmol) in methylene chloride (3 mL) was added trifluoroacetic acid (0.50 mL). The reaction was stirred for 2 hours at ambient temperature then diluted with saturated aqueous sodium hydrogen carbonate. The mixture was extracted with methylene chloride and the combined organics were dried over magnesium sulfate, filtered and concentrated in vacuo to give the title compound (0.069 g)

The title compounds for Examples 14–19 were prepared by a method analogous to that described in Example 13.

EXAMPLE 20

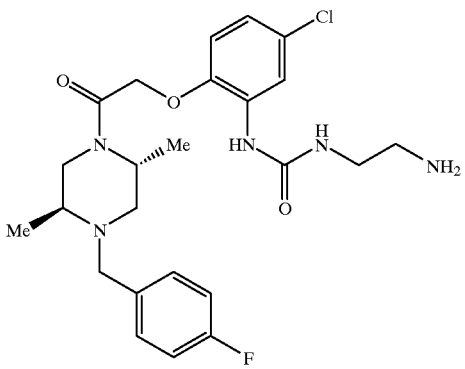

(2R, 5S)-2-(4-Chloro-2-nitro-phenoxy)-1-[4-(4-fluoro-benzyl)-2,5-dimethyl-piperazin-1-yl]-ethanone To a solution of (2R, 5S)-5-chloro-2-{2-[4-(4-fluoro-benzyl)-2,5-dimethyl-piperazin-1-yl]-2-oxo-ethoxy}-benzoic acid methyl ester (1.0 g, 3.35 mmol) in butanone (35 ml) was added 2-nitro-4-chlorophenol (0.639 g, 3.69 mmol), potassium carbonate (0.925 g, 6.7 mmol) and potassium iodide (0.556 g, 3.35 mmol). The reaction mixture was heated at reflux overnight. The reaction mixture was then cooled, diluted with water and extracted with ethyl acetate. The combined organics were dried over magnesium sulfate, filtered and concentrated to give an orange oil. Chromatography on silica gel gave the title compound (1.35 g, 93% yield).

(2R, 5S)-2-(2-Amino-4-chloro-phenoxy)-1-[4-(4-fluoro-benzyl)-2,5-dimethyl-piperazin-1-yl]-ethanone To a solution of (2R, 5S)-2-(4-chloro-2-nitro-phenoxy)-1-[4-(4-fluoro-benzyl)-2,5-dimethyl-piperazin-1-yl]-ethanone (2.2 g, 5.05 mmol) in ethanol (50 ml) in a par bottle was added 5% platinum on carbon (2.2 g). The reaction mixture was subjected to hydrogen gas (35 psi) for thirty minutes. The reaction mixture was filtered through celite and washed with ethanol. The filtrate was concentrated to give a tan foam. Chromatography on silica gel gave the title compound (1.42 g, 70% yield).

(2R, 5S)-(5-Chloro-2-{2-[4-(4-fluoro-benzyl)-2,5-dimethyl-piperazin-1-yl]-2-oxo-ethoxy}-phenyl)-carbamic acid 4-nitro-phenyl ester To a solution of (2R, 5S)-2-(2-amino-4-chloro-phenoxy)-1-[4-(4-fluoro-benzyl)-2,5-dimethyl-piperazin-1-yl]-ethanone (0.150 g, 0.37 mmol) in dichloromethane (7 ml) was added pyridine (0.066 ml, 0.82 mmol) followed by 4-nitrophenyl chloroformate (0.075 g, 0.41 mmol). The reaction was stirred at ambient temperature for 3½ hours. The reaction mixture was concentrated followed by chromatography on silica gel to give the title compound (0.153 g, 74% yield).

(2R,5S)-1-(2-Amino-ethyl)-3-(5-chloro-2-{2-[4-(4-fluoro-benzyl)-2,5-dimethyl-piperazin-1-yl]-2-oxo-ethoxy}-phenyl)-urea To a solution of (2R, 5S)-(5-chloro-2-{2-[4-(4-fluoro-benzyl)-2,5-dimethyl-piperazin-1-yl]-2-oxo-ethoxy}-

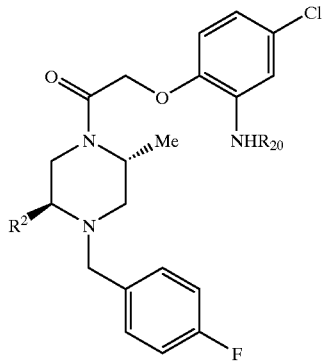

| Example | R²⁰ | R² |
|---|---|---|
| 14 | (C=O)CH₂CH₂NHAc | H |
| 15 | (C=O)CH₂NH₂ | H |
| 16 | (C=O)CH₂NHAc | H |
| 17 | (C=O)C(CH₃)₂OH | H |
| 18 | (C=O)CH₂CH₂C(=O)NH₂ | H |
| 19 | (C=O)CH₂-(2-pyridyl) | H | phenyl)-carbamic acid 4-nitro-phenyl ester (0.206 g, 0.37 mmol) in dry methanol (6 ml) was added ethyldiamine (0.05 ml, 0.814 mmol). The reaction was stirred at ambient temperature overnight. The reaction was concentrated and chromatagraphed on silica gel to give the title compound (0.115 g, 63% yield).

The title compounds for Examples 21–27 were prepared by a method analogous to that described in Example 20.

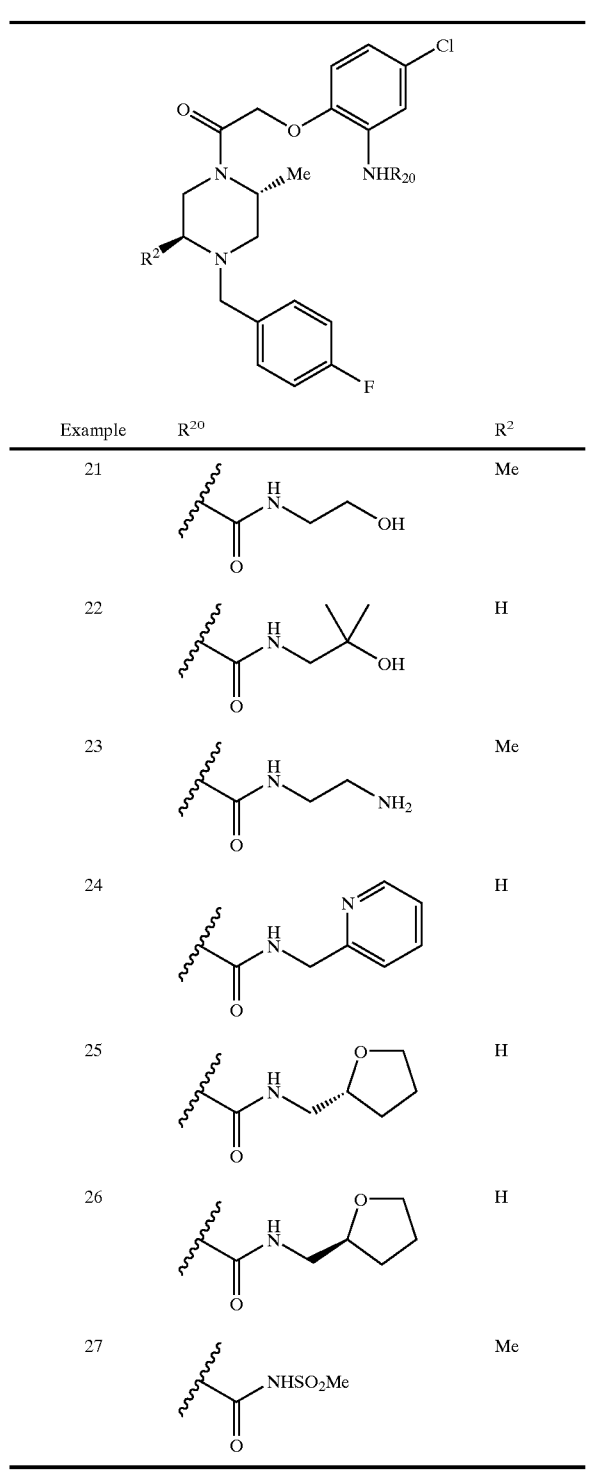

EXAMPLE 28

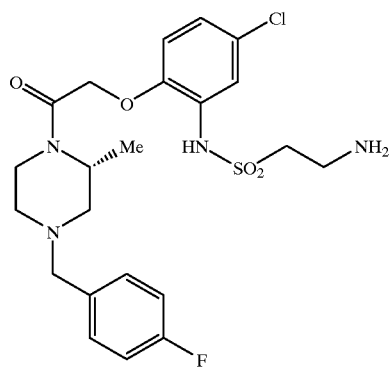

(2R)-2-Amino-ethanesulfonic acid (5-chloro-2-{2-[4-(4-fluoro-benzyl)-2-methyl-piperazin-1-yl]-2-oxo-ethoxy}-phenyl)-amide 2-(1,3-Dioxo-1,3-dihydro-isoindol-2-yl)-ethanesulfonic acid (5-chloro-2-{2-[4-(4-fluoro-benzyl)-2-methyl-piperazin-1-yl]-2-oxo-ethoxy}-phenyl)-amide To a solution of of 2-(2-amino-4-chloro-phenoxy)-1-[4-(4-fluoro-benzyl)-2-methyl-piperazin-1-yl]-ethanone (0.050 g, 0.13 mmol) in methylene chloride (1 mL) at ambient temperature was added triethylamine (0.027 mL, 0.19 mmol) and 2-(1,3-dioxo-1,3-dihydro-isoindol-2-yl)-ethanesulfonyl chloride (0.045 g, 0.17 mmol). The reaction was stirred overnight at ambient temperature. Additional triethylamine ((0.027 mL, 0.19 mmol) and 2-(1,3-dioxo-1,3-dihydro-isoindol-2-yl)-ethanesulfonyl chloride (0.045 g, 0.17 mmol) was added. The reaction was stirred one hour, then additional triethylamine (0.055 mL, 0.34 mmol) was added. The reaction was stirred and hour, then additional 2-(1,3-dioxo-1,3-dihydro-isoindol-2-yl)-ethanesulfonyl chloride (0.090 g, 0.34 mmol) was added. After stirring an additional 1 hour, the reaction was treated with saturated aqueous sodium hydrogen carbonate and extracted with methylene chloride (3×). The combined organics were dried over magnesium sulfate, filtered and concentrated in vacuo. Purification via radial chromatography (2 mm plate) gave the title compound (0.030 g).

(2R)-2-Amino-ethanesulfonic acid (5-chloro-2-{2-[4-(4-fluoro-benzyl)-2-methyl-piperazin-1-yl]-2-oxo-ethoxy}-phenyl)-amide To a solution of 2-(1,3-dioxo-1,3-dihydro-isoindol-2-yl)-ethanesulfonic acid (5-chloro-2-{2-[4-(4-fluoro-benzyl)-2-methyl-piperazin-1-yl]-2-oxo-ethoxy}-phenyl)-amide (0.030 g, 0.048 mmol) in EtOH (1 mL) at ambient temperature was added hydrazine hydrate (0.025 mL). The reaction was stirred overnight at ambient temperature then diluted with water and extracted with methylene chloride (2×). The combined organics were washed with saturated aqueous brine and dried over sodium sulfate, filtered and concentrated in vacuo. Purification via radial chromatography (2 mm plate) gave the title compound (0.014 g).

The title compounds for Examples 29–34 were prepared by a method analogous to that described in Example 28.

| Example | R²⁰ | R² |
|---|---|---|
| 29 | —SO₂CF₃ | Me |
| 30 | ⸺SO₂⸺CH₂CH₂⸺NH⸺C(O)⸺NH₂ | H |
| 31 | ⸺SO₂⸺CH₂CH₂⸺NH⸺C(=N-CN)⸺NH₂ | H |
| 32 | ⸺SO₂⸺CH₂CH₂⸺NH⸺C(O)O⸺(tetrahydrofuran-3-yl) | H |
| 33 | ⸺SO₂⸺CH₂CH₂⸺NH⸺C(O)O⸺(tetrahydrofuran-3-yl) | H |
| 34 | —SO₂N(Me)₂ | Me |

EXAMPLE 35

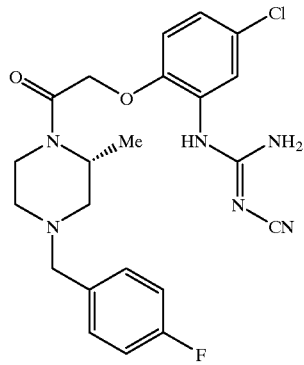

(2R)-N-(5-Chloro-2-{2-[4-(4-fluoro-benzyl)-2-methyl-piperazin-1-yl]-2-oxo-ethoxy}-phenyl)-cyanoguanidine 1-(5-Chloro-2-{2-[4-(4-fluoro-benzyl)-2-methyl-piperazin-1-yl]-2-oxo-ethoxy}-phenyl)-N-cyano-S-methyl-isothiourea To a solution of of 2-(2-amino-4-chloro-phenoxy)-1-[4-(4-fluoro-benzyl)-2-methyl-piperazin-1-yl]-ethanone (0.30 g, 0.77 mmol) in tetrahydrofuran (5 mL) at ambient temperature was added sodium hydride (0.029 g, 1.22 mmol) and the reaction was stirred for 30 minutes. To this was added S,S1-dimethyl N-cyanodithio iminocarbonate (0.168, 1.15 mmol) and the mixture was heated at reflux overnight. The reaction was cooled and quenched with saturated aqueous ammonium chloride. The mixture was extracted with EtOAc and the combined organics were dried over Na₂SO₄, filtered and concentrated in vacuo. Chromatography on silica gel gave the title compound (0.350 g)

(2R)-N-(5-Chloro-2-{2-[4-(4-fluoro-benzyl)-2-methyl-piperazin-1-yl]-2-oxo-ethoxy}-phenyl)-cyanoguanidine To a solution of 1-(5-chloro-2-{2-[4-(4-fluoro-benzyl)-2-methyl-piperazin-1-yl]-2-oxo-ethoxy}-phenyl)-N-cyano-S-methyl-isothiourea (0.045 g, 0.092 mmol) in EtOH (1 mL) was added ammonium hydroxide (0.100 mL) and the resulting solution was shaken at 60° C. overnight. The crude reaction mixture was purified directly via radial chromatography (2 mm plate) to give the title compound (0.027 g).

The title compounds for Examples 36–38 were prepared by a method analogous to that described in Example 35.

| Example | R²⁰ | R² |
|---|---|---|
| 36 | 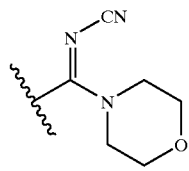 | H |

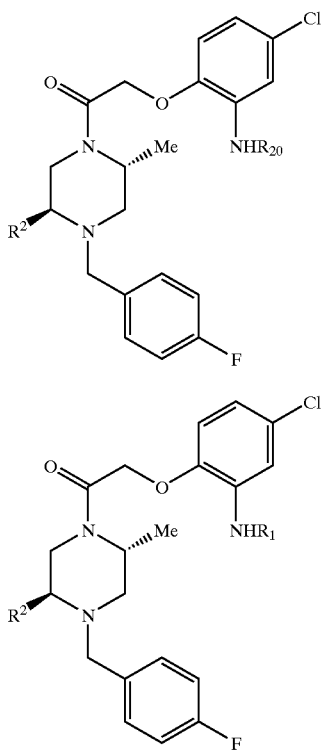

| Example | R[20] | R[2] |
|---|---|---|
| 37 | [piperazine-C(=NCN)-] | H |
| 38 | [-C(=NCN)NHCH2C(O)NH2] | H |

EXAMPLE 39

(2R,5S)-2-{4-Chloro-2-[(2-diethylamino-ethylamino)-methyl]-phenoxy}-1-[4-(4-fluoro-benzyl)-2,5-dimethyl-piperazin-1-yl]-ethanone (2R,5S)-5-Chloro-2-{2-[4-(4-fluoro-benzyl)-2,5-dimethyl-piperazin-1-yl]-2-oxo-ethoxy}-benzaldehyde To a solution of 2-chloro-1-[4-(4-fluoro-benzyl)-2,5-dimethyl-piperazin-1-yl]-ethanone (2.87 g, 9.6 mmol) in DMF (20 mL) was added 5-chlorosalicylaldehyde (1.65 g, 10.5 mmol), potassium carbonate (2.64 g, 19.2 mmol) and potassium iodide (1.59 g, 9.6 mmol). The resulting mixture was heated to 100° C. for 12 hours. The reaction was cooled, diluted with saturated aqueous brine and extracted with ethyl acetate (3×). The combined organics were dried over magnesium sulfate and filtered. The filtrate was concentrated in vacuo to give crude product. Purification via chromatography on silica gel (15% EtOAc/Hexanes) gave the title compound 3.40 g, 85% yield.)

(2R,5S)-2-{4-Chloro-2-[(2-diethylamino-ethylamino)-methyl]-phenoxy}-1-[4-(4-fluoro-benzyl)-2,5-dimethyl-piperazin-1-yl]-ethanone To a solution of (2R,5S)-5-chloro-2-{2-[4-(4-fluoro-benzyl)-2,5-dimethyl-piperazin-1-yl]-2-oxo-ethoxy}-benzaldehyde (0.100 g, 0.25 mmol) in 10:1 dichloroethane acetic acid (2.2 mL) was added (diethylamino)ethylamine (0.088 mL, 0.625 mmol) and the resulting solution was stirred for 1 hour at ambient temperature. To this was added sodium cyanoborohydride (0.0094 g, 0.15 mmol) and the reaction was stirred overnight at ambient temperature. Upon completion water was added and the mixture was basified with solid sodium bicarbonate (pH>10). The product was extracted with dichloromethane (2×) and diethyl ether (2×). The combined organics were dried over magnesium sulfate, filtered and concentrated in vacuo. Chromatography on silica gel gave the title compound (0.039 g, x 30% yield)

The title compounds for Examples 40–62 were prepared by a method analogous to that described in Example 39.

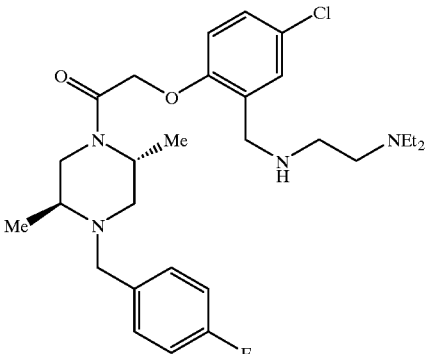

| Example | R[20] | R[2] |
|---|---|---|
| 40 | [-CH2CH2CH2-morpholinyl] | Me |
| 41 | [-CH2CH2-piperazinyl-NH] | Me |
| 42 | [-CH2CH2-pyrrolidinyl] | Me |

-continued

[Structure: piperazine with 2-Me, N1-acyl-CH2-O-(4-chloro-2-NHR20-phenyl), N4-(4-fluorobenzyl), R2 at 5-position]

| Example | R20 | R2 |
|---|---|---|
| 43 | -CH2-[(S)-tetrahydrofuran-2-yl] | Me |
| 44 | -CH2-[(R)-tetrahydrofuran-2-yl] | Me |
| 45 | -CH2CH2-(pyridin-2-yl) | Me |
| 46 | -CH2-(furan-2-yl) | Me |
| 47 | -CH2CH2-(1H-imidazol-4-yl) | Me |
| 48 | -CH2CH2-CO2H | Me |
| 49 | -CH2CH2-CN | Me |
| 50 | -CH2-CN | Me |
| 51 | -CH2CH2-C(O)NH2 | Me |

-continued

[Same structure]

| Example | R20 | R2 |
|---|---|---|
| 52 | -CH2CH2CH2-C(O)NH2 | Me |
| 53 | -CH2CH2CH2-NH2 | Me |
| 54 | -CH2CH2CH2-NHAc | Me |
| 55 | -CH2CH2CH2-NHMe | Me |
| 56 | -CH2CH2CH2CH2-NHC(O)OMe | Me |
| 57 | -CH2CH2CH2CH2-NHSO2Me | Me |
| 58 | -CH2CH2-OEt | Me |
| 59 | -CH2CH2-NHC(O)NH2 | Me |
| 60 | -CH2CH2-OH | Me |
| 61 | -CH2CH2CH2-OSO3H | Me |

-continued

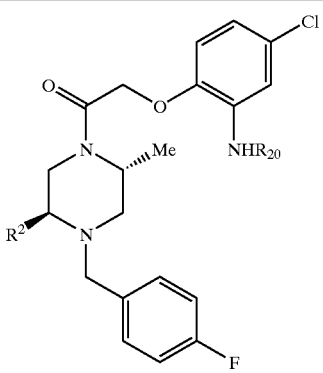

| Example | R[20] | R[2] |
|---|---|---|
| 62 | ![structure with O-C(=O)-NH2] | Me |

EXAMPLE 63

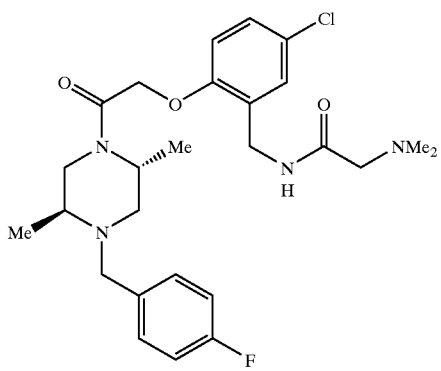

N(5-chloro-2-{2-[4-(4-fluoro-benzyl)-2,5-dimethyl-piperazin-1-yl]-2-oxo-ethoxy}-benzyl)-2-diethylamino-acetamide (2R,5S)-2-(2-Aminomethyl-4-chloro-phenoxy)-1-[4-(4-fluoro-benzyl)-2,5-dimethyl-piperazin-1-yl]-ethanone To a solution of (2R,5S)-5-chloro-2-{2-[4-(4-fluoro-benzyl)-2,5-dimethyl-piperazin-1-yl]-2-oxo-ethoxy}-benzaldehyde (1.86 g, 4.44 mmol) in MeOH (20 mL) was added ammonium acetate (3.42 g, 44 mmol) and sodium cyanoborohydride (0.195 g, 3.1 mmol). The resulting mixture was stirred overnight at ambient temperature. The reaction was quenched with concentrated hydrochloric acid and concentrated in vacuo. The residue was dissolved in water and basified with aqueous 3N NaOH (pH>10). The product was extracted with dichloromethane (2x) and ethyl acetate (2x). The combined organics were dried over magnesium sulfate, filtered and concentrated in vacuo. Chromatography on silica gel gave the title compound (1.29 g, 69% yield)

N-(5-Chloro-2-(2-[4-(4-fluoro-benzyl)-2,5-dimethyl-piperazin-1-yl]-2-oxo-ethoxy)-benzyl)-2-diethylamino-acetamide To a solution of N,N-dimethylglycine (0.014 g, 0.13 mmol) and (2R,5S)-2-(2-aminomethyl-4-chloro-phenoxy)-1-[4-(4-fluoro-benzyl)-2,5-dimethyl-piperazin-1-yl]-ethanone (0.063 g, 0.15 mmol) in dichloromethane (2 mL) was added 1-(3-dimethylaminopropyl)-3-ethylcarbodiimide (0.034 g, 0.18 mmol), 1-hydroxybenzotriazole (0.021 g, 0.15 mmol), and triethylamine (0.036 mL, 0.36 mmol). After the reaction was stirred for 48 hours, the solution was diluted with saturated aqueous sodium bicarbonate and extracted with dichloromethane (3x). The combined organics were dried over magnesium sulfate, filtered and concentrated in vacuo. Chromatography on silica gel gave the title compound (0.063 g, 80%).

The title compounds for Examples 64–85 were prepared by a method analogous to that described in Example 63.

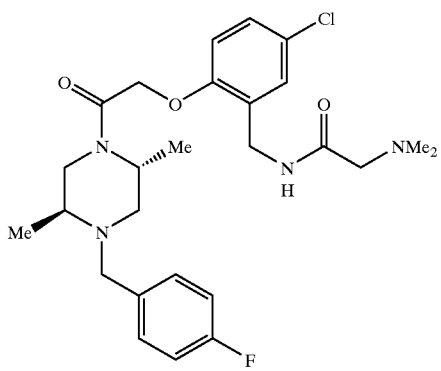

| Example | R[20] | R[2] |
|---|---|---|
| 64 | ![C(=O)CH2NHAc] | Me |
| 65 | ![C(=O)CH2CN] | Me |
| 66 | ![C(=O)CH2CH2NH2] | Me |
| 67 | ![C(=O)CH2CH2C(=O)NH2] | Me |
| 68 | ![C(=O)CH2CH2C(=O)NMe2] | Me |
| 69 | ![C(=O)CH2CH2CO2Me] | Me |

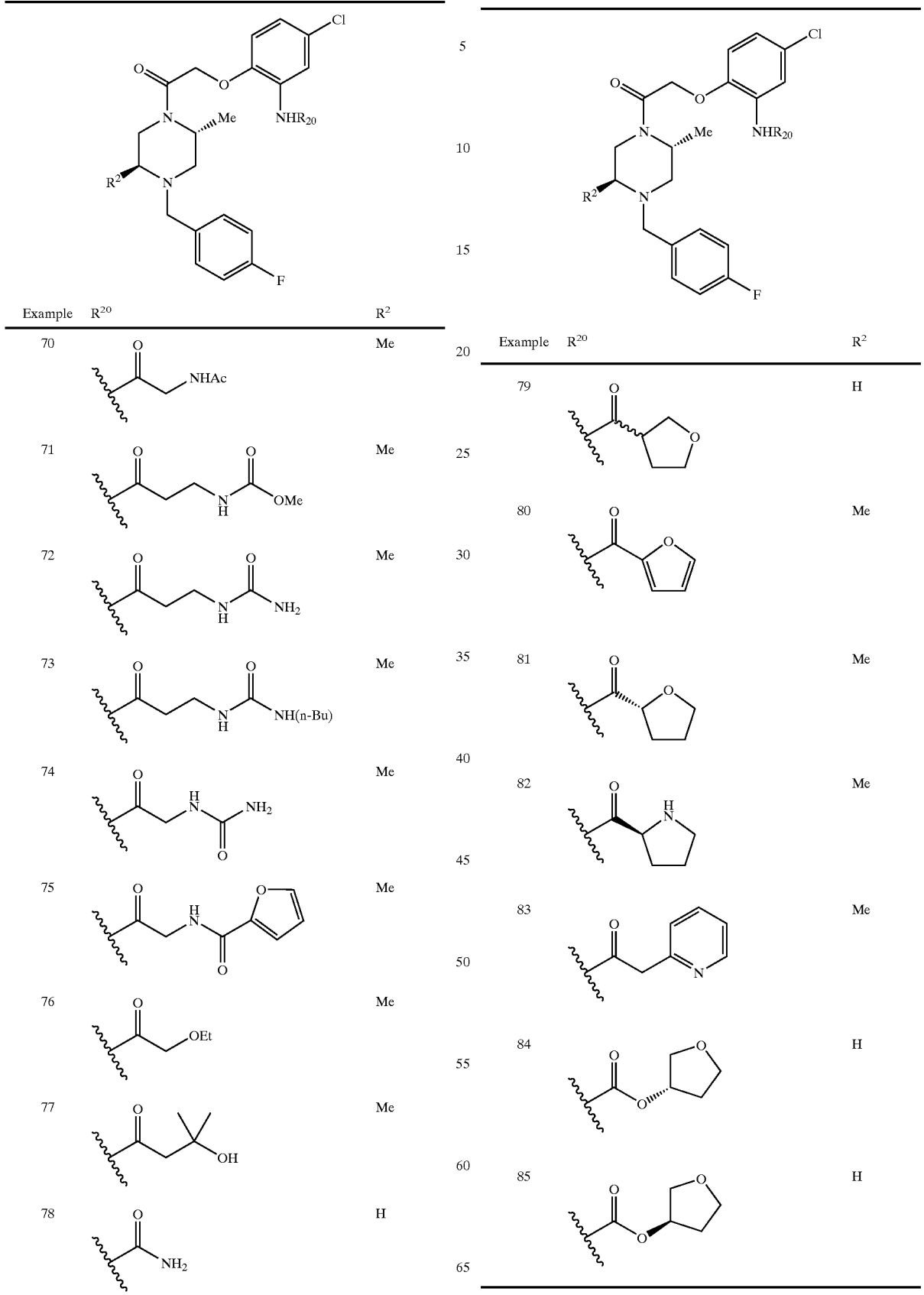

EXAMPLE 86

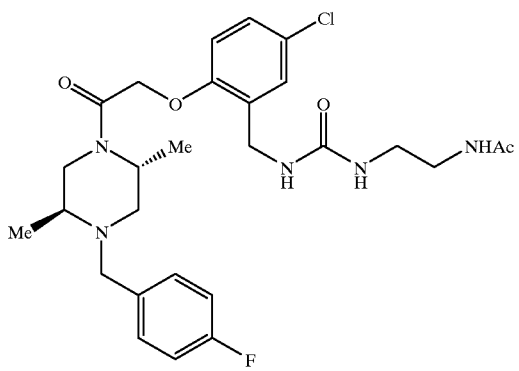

(2R,5S)-(N-{2-[3-(5-Chloro-2-{2-[4-(4-fluoro-benzyl)-2,5-dimethyl-piperazin-1-yl]-2-oxo-ethoxy}-benzyl)-ureido]-ethyl}-acetamide To a solution of (2R,5S)-5-chloro-2-{2-[4-(4-fluoro-benzyl)-2,5-dimethyl-piperazin-1-yl]-2-oxo-ethoxy}-benzylamine (0.200 g, 0.477 mmol) in methylene chloride (10 mL) was added pyridine (0.077 mL, 0.954 mmol) and 4-nitro phenyl chloroformate (0.097 g, 0.525 mmol). The resulting mixture was stirred for one hour at ambient temperature and then concentrated in vacuo. The residue (0.055 g, 0.094 mmol) was dissolved in methanol (1 mL). N-Acetylethylenediamine (0.019 mL, 0.188 mmol) was added and the reaction was stirred at room temperature overnight. The reaction was concentrated in vacuo and chromatography on silica gel gave the title compound (0.019 g, 27%).

The title compounds for Examples 87–90 were prepared by a method analogous to that described in Example 86.

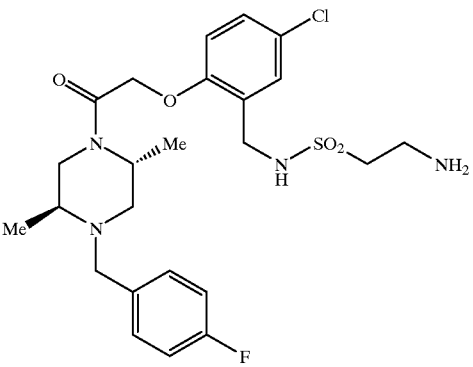

| Example | R[20] | R[2] |
|---|---|---|
| 87 | NH2) | Me |
| 88 | | Me |
| 89 | | Me |
| 90 | | Me |

EXAMPLE 91

(2R,5S)-2-Amino-ethanesulfonic acid 5-chloro-2-{2-[4-(4-fluoro-benzyl)-2,5-dimethyl-piperazin-1-yl]-2-oxo-ethoxy}-benzylamide
(2R,5S)-2-(1,3-Dioxo-1,3-dihydro-isoindol-2-yl)-ethanesulfonic acid 5-chloro-2-{2-[4-(4-fluoro-benzyl)-2,5-dimethyl-piperazin-1-yl]-2-oxo-ethoxy}-benzylamide To a solution of (2R,5S)-5-chloro-2-{2-[4-(4-fluoro-benzyl)-2,5-dimethyl-piperazin-1-yl]-2-oxo-ethoxy}-benzyl amine (0.060 g, 0.143 mmol) in methylene chloride (3 mL) was added 2-(1,3-dioxo-1,3-dihydro-isoindol-2-yl)-ethanesulfonyl chloride (0.043 g, 0.150 mmol) and triethylamine (0.060 mL, 0.43 mmol) and the solution was stirred 1 hr at ambient temperature. The reaction was diluted with saturated aqueous sodium hydrogen carbonate and extracted with methylene chloride. The combined organics were dried over magnesium sulfate, filtered and concentrated in vacuo. Chromatography on silica gel gave the title compound (0.073 g, 77%).

(2R,5S)-2-Amino-ethanesulfonic acid 5-chloro-2-{2-[4-(4-fluoro-benzyl)-2,5-dimethyl-piperazin-1-yl]-2-oxo-ethoxy}-benzylamide To a solution of (2R,5S)-2-(1,3-Dioxo-1,3-dihydro-isoindol-2-yl)-ethanesulfonic acid 5-chloro-2-{2-[4-(4-fluoro-benzyl)-2,5-dimethyl-piperazin-1-yl]-2-oxo-ethoxy}-benzylamide (0.073 g, 0.111 mmol) in EtOH (1 mL) was added hydrazine (35% aq. 0.25 mL, 2.73 mmol) and the solution was stirred overnight at ambient temperature. The reaction was filtered through a glass frit and washed with EtOH. The filtrate was concentrated in vacuo to give the title compound (0.056 g, 96%)

The title compounds for Examples 92–93 were prepared by a method analogous to that described in Example 91.

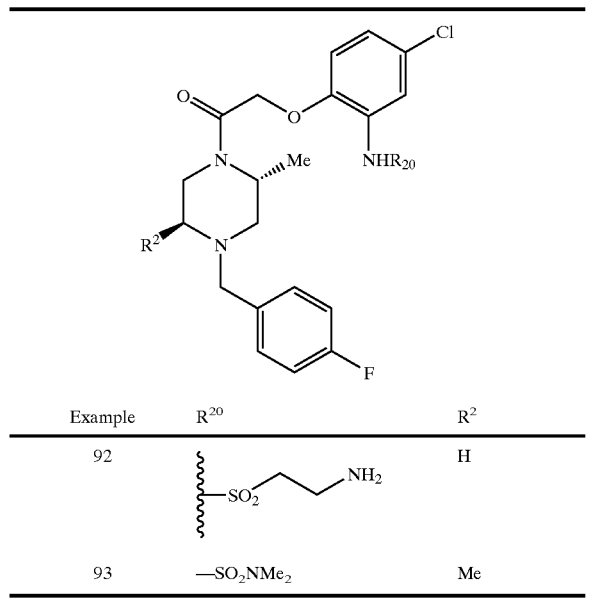

| Example | $R^{20}$ | $R^2$ |
|---|---|---|
| 92 | —SO$_2$CH$_2$CH$_2$NH$_2$ | H |
| 93 | —SO$_2$NMe$_2$ | Me |

EXAMPLE 94

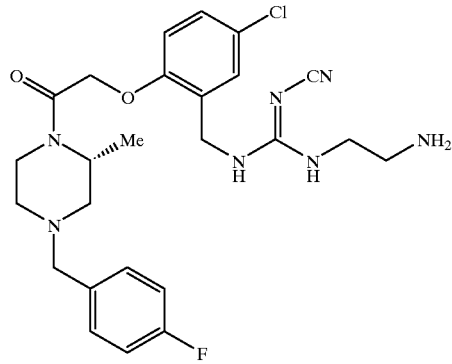

(2R)-N-(2-Amino-ethyl)-N'-(5-chloro-2-{2-[4-(4-fluoro-benzyl)-2-methyl-piperazin-1-yl]-2-oxo-ethoxy}-benzyl)-cyanoguanidine A solution of 2-(2-aminomethyl-4-chloro-phenoxy)-1-[4-(4-fluoro-benzyl)-2-methyl-piperazin-1-yl]-ethanone (0.025 g, 0.062 mmol) and diphenyl cyanocarbonimidate (0.016 g, 0.068 mmol) in ethanol (1 mL) was heated on a shaker plate at 60° C. After 22 h, ethylenediamine (0.008 mL, 0.123 mmol) was added and the resulting solution was heated on a shaker plate at 60° C. for an additional 21 h. The solution was cooled to ambient temperature, concentrated and purified using radial chromatography to yield the title compound (0.021 g, 67%). The title compounds for Examples 95–96 were prepared by a method analogous to that described in Example 94.

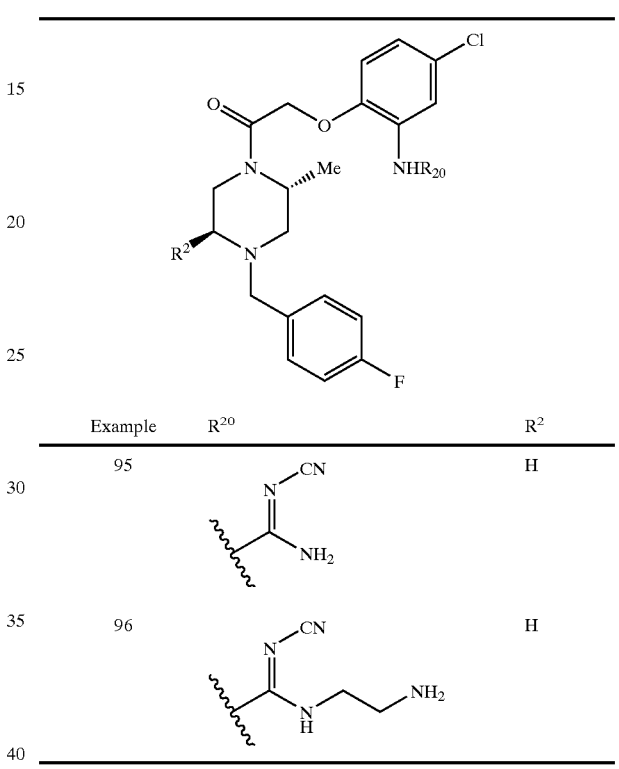

| Example | $R^{20}$ | $R^2$ |
|---|---|---|
| 95 | —C(=N-CN)NH$_2$ | H |
| 96 | —C(=N-CN)NH-CH$_2$CH$_2$NH$_2$ | H |

EXAMPLE 97

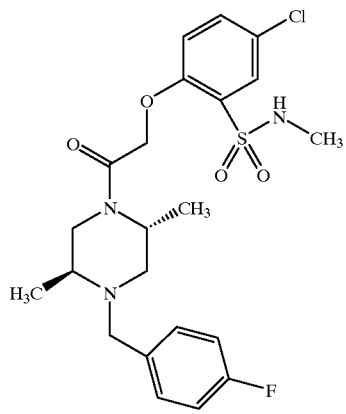

(2R,5S)-5-Chloro-2-{2-[4-(4-fluoro-benzyl)-2,5-dimethyl-piperazin-1-yl]-2-oxo-ethoxy}-N-methyl-benzenesulfonamide 5-Chloro-2-methoxy-N-methyl-benzenesulfonamide To a solution of 5-Chloro-2-methoxy-benzenesulfonyl chloride (1.0 g, 4.15 mmol) in tetrahydrofuran (8 ml) was bubbled methylamine gas until saturated. The reaction mixture was sealed with a septa and stirred overnight at ambient temperature. The reaction mixture was then concentrated, triterated in dichloromethane and ether, filtered and dried yielding the above titled compound 1.05 g (>100%) white solid.

5-Chloro-2-hydroxy-N-methyl-benzenesulfonamide

To a solution of sodium hydride (60% in mineral oil, 90.24 mg, 2.25 mmol) in dry dimethyl formamide was added thiophenol (0.225 ml, 2.25 mmol) dropwise. To this was then added 5-Chloro-2-methoxy-N-methyl-benzenesulfonamide (531 mg, 2.25 mmol) followed by refluxing for 4 hours. The reaction mixture was cooled, diluted with ethyl acetate and washed with a 1N sulfuric acid solution. The organic layer was separated, dried over magnesium sulfate, filtered and concentrated in vacuo. Chromatography on silica gel yielded the above titled compound (320 mg, 53% yield).

(2R, 5S)-5-Chloro-2-{2-[4-(4-fluoro-benzyl)-2,5-dimethyl-piperazin-1-yl]-2-oxo-ethoxy}-N-methyl-benzenesulfonamide To a solution of (2R, 5S)-2-Chloro-1-[4-(4-fluoro-benzyl)-2,5-dimethyl-piperazin-1-yl]-ethanone (375 mg, 1.26 mmol) in butanone (12 ml) was added 5-Chloro-2-hydroxy-N-methyl-benzenesulfonamide (280 mg, 1.26 mmol), potassium carbonate (348 mg, 2.52 mmol) and potassium iodide (209 mg, 1.26 mmol). The resulting reaction mixture was refluxed for 4 hours. It was allowed to cool, diluted with ethyl acetate and washed with brine. The organic layer was separated, dried over magnesium sulfate, filtered and concentrated in vacuo. Chromatography on silica gel gave the above titled compound (320 mg, 53% yield).

The title compounds for Examples 98–100 were prepared by a method analogous to that described in Example 97.

| Example | $R^{20}$ | $R^2$ |
|---|---|---|
| 98 | —$NH_2$ | Me |
| 99 | ⁓—N◯NH | Me |
| 100 | ⁓—N◯O | Me |

What is claimed is:

1. A compound of the formula

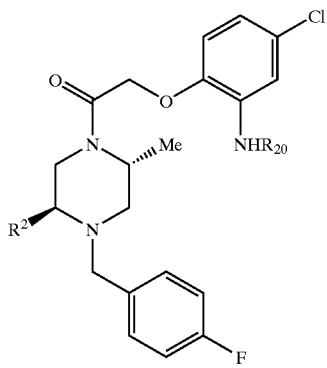

or the pharmaceutically acceptable salt thereof; wherein $R^{20}$ and $R^2$ are as defined below:

| $R^{20}$ | $R^2$ |
|---|---|
| ⁓—S(O$_2$)—CH$_2$CH$_2$—NH$_2$ | H |
| ⁓—SO$_2$—CH$_2$CH$_2$—NH—C(O)—NH$_2$ | Me |
| ⁓—SO$_2$—CH$_2$CH$_2$—NH—C(=N—CN)—NH$_2$ | H |
| ⁓—SO$_2$—NH—C(O)—O—(3R)-tetrahydrofuran | H |
| ⁓—SO$_2$—NH—C(O)—O—(3S)-tetrahydrofuran | H |
| —SO$_2$N(Me)$_2$ | Me. |

2. A compound of the formula
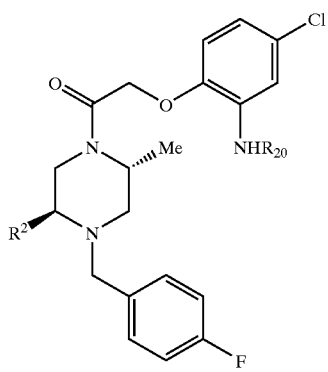
or the pharmaceutically acceptable salt thereof; wherein $R^{20}$ and $R^2$ are as defined below:
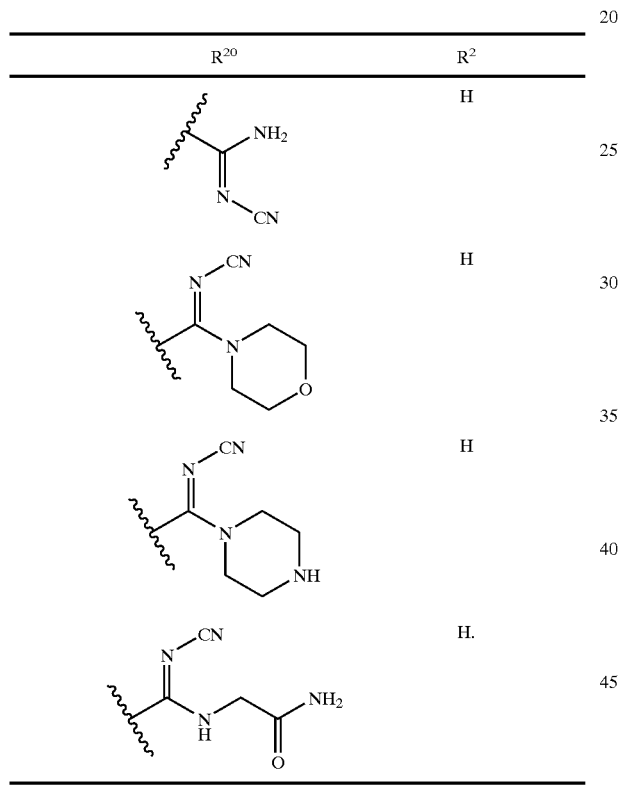
3. A compound of the formula
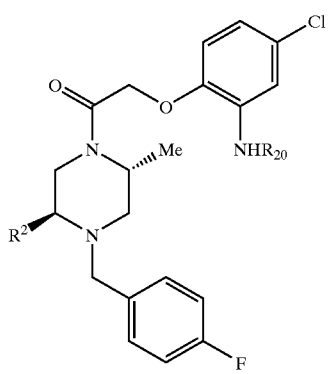
or the pharmaceutically acceptable salt thereof; wherein $R^{20}$ and $R^2$ are as defined below:
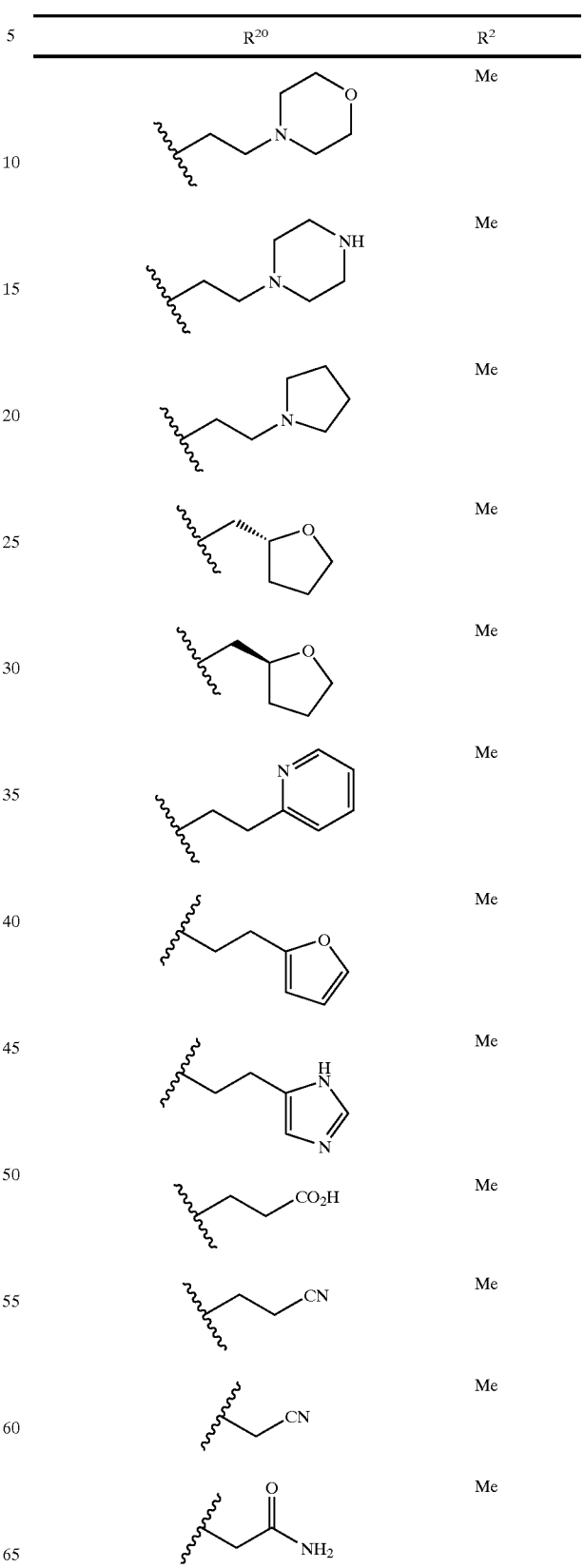

-continued
| R²⁰ | R² |
|---|---|
| 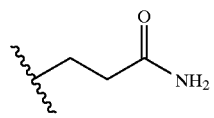 | Me |
| 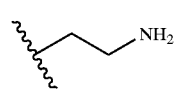 | Me |
| 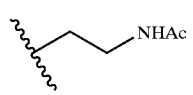 | Me |
| 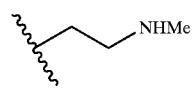 | Me |
| 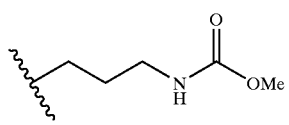 | Me |
| 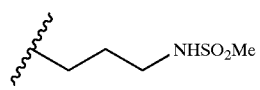 | Me |
| 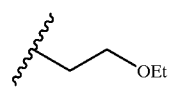 | Me |
| 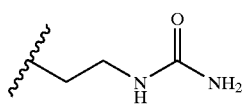 | Me |
| 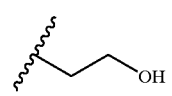 | Me |
| 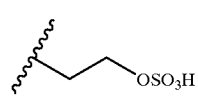 | Me |
| 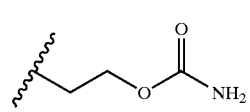 | Me. |
4. A compound of the formula
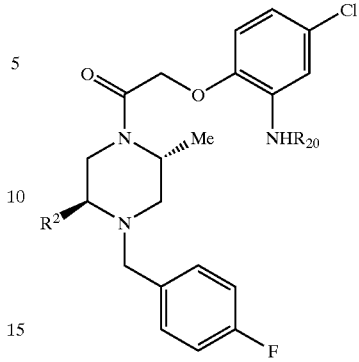
or the pharmaceutically acceptable salt thereof; wherein $R^{20}$ and $R^2$ are as defined below:
| R²⁰ | R² |
|---|---|
| 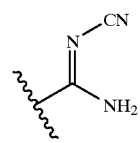 | H |
| —SO₂NMe₂ | Me. |
5. A compound of the formula
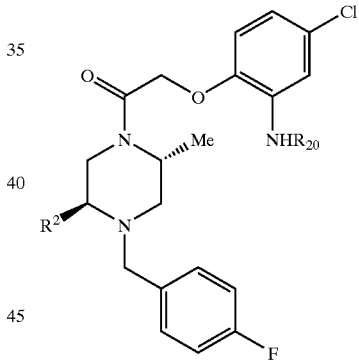
or the pharmaceutically acceptable salt thereof; wherein $R^2$ is H and $R^{20}$ is
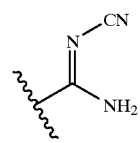
or
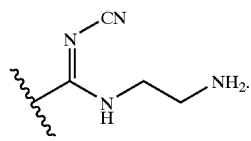

6. A pharmaceutical composition for treating or preventing a disorder or condition that can be treated or prevented by inhibiting chemokine binding to the receptor CCR1 in a mammal, comprising an amount of a compound according to any of claims, 1, 2, 3, 4, 5, or a pharmaceutically acceptable salt thereof, effective in treating or preventing such disorder or condition and a pharmaceutically acceptable carrier.

* * * * *